US011243215B2

(12) United States Patent
John et al.

(10) Patent No.: US 11,243,215 B2
(45) Date of Patent: Feb. 8, 2022

(54) 3D-EXOQUANT METHOD FOR THE ANALYSIS OF SURFACE MOLECULES AND QUANTIFICATION OF TISSUE-SPECIFIC EXOSOMES IN BIOLOGICAL FLUIDS

(71) Applicant: The Regents of the University of California, Oakland, CA (US)

(72) Inventors: Varghese John, Los Angeles, CA (US); Jesus Campagna, Playa Del Rey, CA (US); Tina Bilousova, Santa Monica, CA (US); Patricia R. Spilman, Mill Valley, CA (US); Peter James Heinzelman, Los Angeles, CA (US); Asa Hatami, Los Angeles, CA (US); Mohammad Parvez Alam, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 568 days.

(21) Appl. No.: 16/070,249

(22) PCT Filed: Jan. 13, 2017

(86) PCT No.: PCT/US2017/013510
§ 371 (c)(1),
(2) Date: Jul. 13, 2018

(87) PCT Pub. No.: WO2017/124000
PCT Pub. Date: Jul. 20, 2017

(65) Prior Publication Data
US 2019/0025330 A1    Jan. 24, 2019

Related U.S. Application Data
(60) Provisional application No. 62/317,241, filed on Apr. 1, 2016, provisional application No. 62/278,851, filed on Jan. 14, 2016.

(51) Int. Cl.
| | |
|---|---|
| G01N 33/543 | (2006.01) |
| G01N 33/68 | (2006.01) |
| G01N 33/542 | (2006.01) |
| C07D 207/46 | (2006.01) |
| G01N 33/567 | (2006.01) |
| G01N 33/574 | (2006.01) |

(52) U.S. Cl.
CPC ....... *G01N 33/6896* (2013.01); *C07D 207/46* (2013.01); *G01N 33/542* (2013.01); *G01N 33/54313* (2013.01); *G01N 33/54326* (2013.01); *G01N 33/54353* (2013.01); *G01N 33/567* (2013.01); *G01N 33/57484* (2013.01); *G01N 2570/00* (2013.01); *G01N 2800/285* (2013.01); *G01N 2800/2821* (2013.01); *G01N 2800/2835* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2007/0002543 A1 | 11/2007 | Abrignani et al. | |
| 2007/0298118 A1 | 12/2007 | Lotvall et al. | |
| 2009/0148460 A1 | 6/2009 | Delcayre et al. | |
| 2010/0151480 A1 | 6/2010 | Taylor et al. | |
| 2010/0184046 A1* | 7/2010 | Klass ................ | C12Q 1/6811 435/7.1 |
| 2010/0298151 A1 | 11/2010 | Taylor et al. | |
| 2011/0177054 A1 | 7/2011 | Gibbings et al. | |
| 2012/0183575 A1 | 7/2012 | Gabrielsson | |

(Continued)

FOREIGN PATENT DOCUMENTS

| | | | |
|---|---|---|---|
| CN | 105074468 A | 11/2015 | |
| GB | WO2009097470 A1 * | 8/2009 | ............. G01N 33/53 |

OTHER PUBLICATIONS

PCT International Search Report and Written Opinion dated May 25, 2017 issued in PCT/US2017/013510.
PCT International Preliminary Report on Patentability dated Jul. 17, 2018 issued in PCT/US2017/013510.
Catalog No. 10608D, Jun. 2, 2013, "Exosome—Streptavidin for Isolation/Detection—Protocol for use in Flow Cytometry" *Invitrogen by life technologies*, Publication No. MAN0007668, [3 pages], Retrieved from the Internet—www.lifetechnologies.com: URL: https://tools.thermofisher.com/content/sfs/manuals/exosometstreptavidin_fc.pdf.

(Continued)

*Primary Examiner* — Gary Counts
(74) *Attorney, Agent, or Firm* — Tom Hunter; Weaver Austin Villeneuve & Sampson LLP

(57) ABSTRACT

In various embodiments methods are provided for identifying and/or quantifying one or more antigens of interest (biomarkers) on the surface of cell- or tissue-specific exosomes. In an illustrative embodiments the methods comprise: i) incubating a population of exosomes with one or more tissue-specific antibodies that bind an antigen specific to a tissue or cell type of interest that produces exosomes, where the tissue specific antibodies are attached to acceptor bead or magnetic beads so the antibodies bind exosomes displaying the antigen; ii) obtaining a purified population of exosomes bound by the tissue specific antibodies with and/or without photocleavable linker based technology; iii) incubating a test subset of the isolated tissue-specific exosomes with acceptor beads attached to test antibodies that bind an antigen of interest thereby binding exosomes that display the antigen of interest and a control subset with negative control acceptor beads; v) incubating the test subset of isolated exosomes and the control subset of exosomes with a donor-bearing antibody that binds an exosome specific antigen; and vi) detecting a signal produced upon illumination of the control subset and/or the test; and vii) detecting the antigen(s) of interest.

16 Claims, 23 Drawing Sheets

(56) References Cited

U.S. PATENT DOCUMENTS

| | | |
|---|---|---|
| 2012/0238467 A1 | 9/2012 | Taylor et al. |
| 2013/0028895 A1 | 1/2013 | Wulf et al. |
| 2013/0078658 A1 | 3/2013 | Park et al. |
| 2013/0156801 A1 | 6/2013 | Bond et al. |
| 2013/0157300 A1 | 6/2013 | Park et al. |
| 2013/0172208 A1 | 7/2013 | Mitsuhashi. |
| 2013/0196355 A1 | 8/2013 | Fais et al. |
| 2013/0273544 A1 | 10/2013 | Vlassov et al. |
| 2014/0004181 A1 | 1/2014 | Bond et al. |
| 2014/0120156 A2 | 5/2014 | Bond et al. |
| 2014/0134606 A1 | 5/2014 | Newman et al. |
| 2014/0178888 A1 | 6/2014 | Vlassov et al. |
| 2014/0323553 A1 | 10/2014 | Croce et al. |
| 2015/0017660 A1 | 1/2015 | Ochiya et al. |
| 2015/0093433 A1 | 4/2015 | Leonard et al. |
| 2015/0104801 A1 | 4/2015 | Vlassov et al. |
| 2015/0168400 A1 | 6/2015 | Ichiki et al. |
| 2015/0216899 A1 | 8/2015 | Pusic et al. |
| 2015/0275301 A1 | 10/2015 | Mitsuhashi et al. |
| 2015/0290343 A1 | 10/2015 | Lötvall et al. |

OTHER PUBLICATIONS

Fiandaca et al. (2014) "Identification of preclinical Alzheimer's disease by a profile of pathogenic proteins in neurally derived blood exosomes: A case-control study" *Alzheimer's & Dementia* 1-8.el [10 pages].

Heinzelman et al. (2016) "Nanoscale Extracellular Vesicle Analysis in Alzheimer's Disease Diagnosis and Therapy" *International Journal of Alzheimer's Disease*, vol. 2016, Article ID 8053139 [10 pages] http://dx.doi.org/10.1155/2016/8053139.

Yoshioka et al. (2014) "Ultra-sensitive liquid biopsy of circulating extracellular vesicles using ExoScreen" Nature Communications 5:3591 [8 pages].

\* cited by examiner

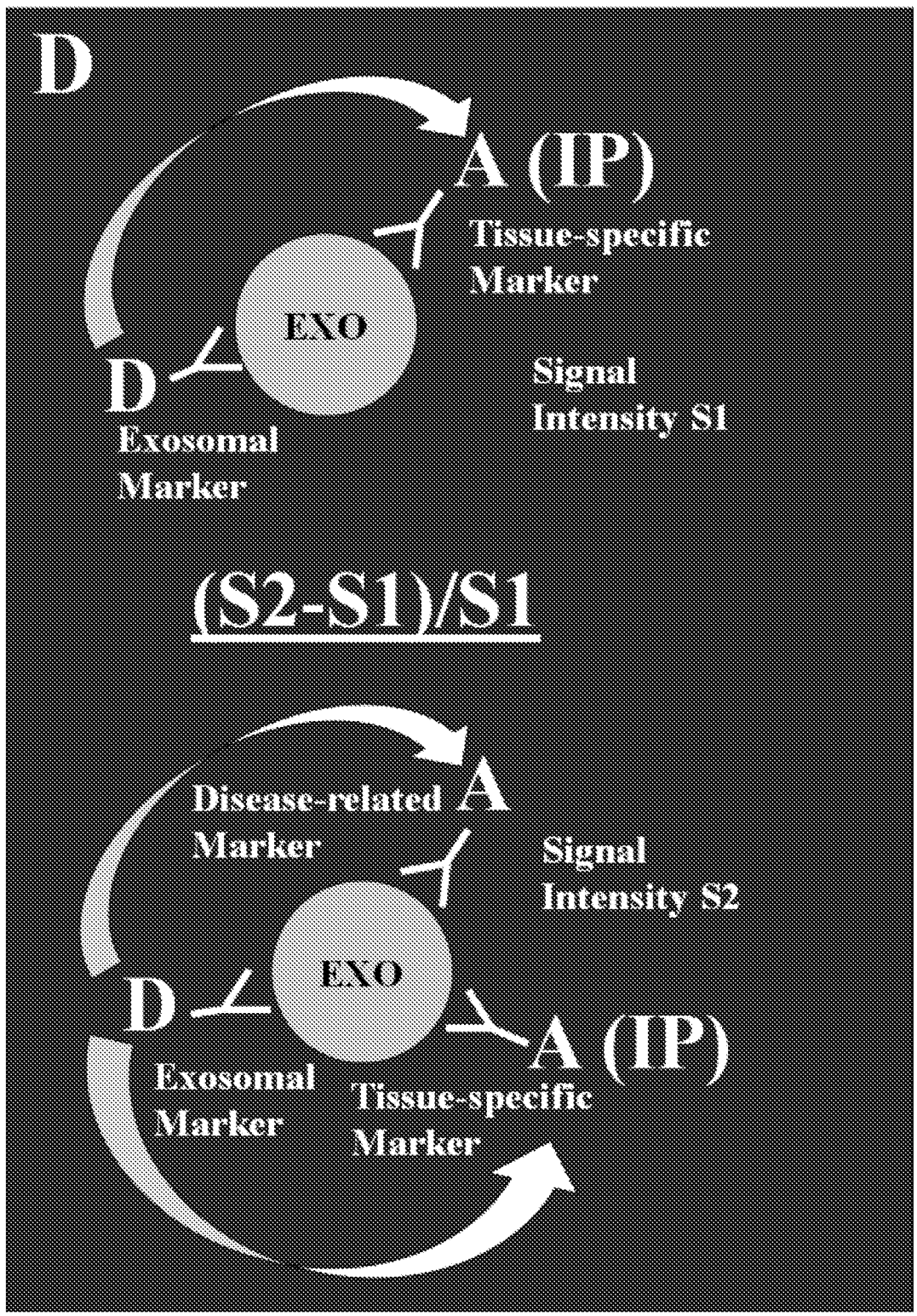
Fig. 2, cont'd.

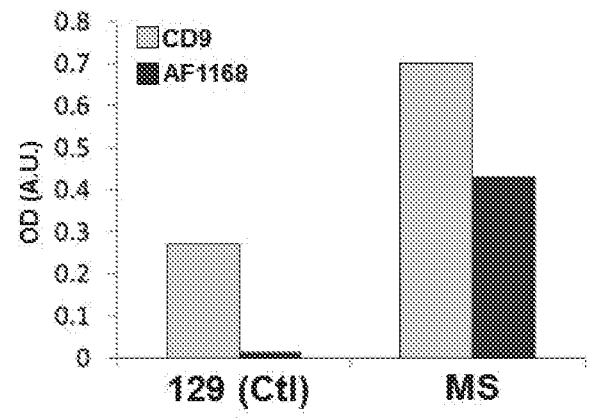
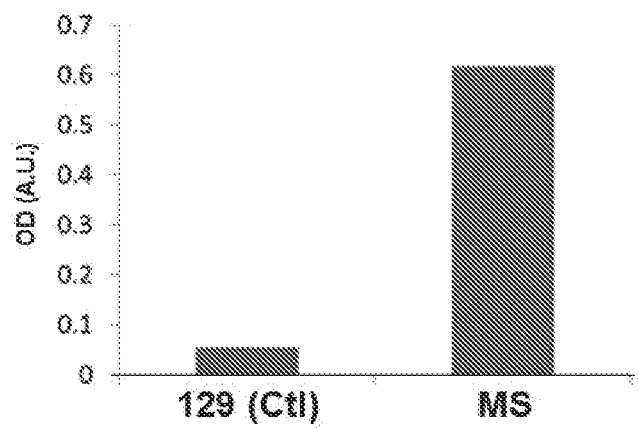
Fig. 27

3D-EXOQUANT METHOD FOR THE ANALYSIS OF SURFACE MOLECULES AND QUANTIFICATION OF TISSUE-SPECIFIC EXOSOMES IN BIOLOGICAL FLUIDS

CROSS-REFERENCE TO RELATED APPLICATIONS

This application is a 371 US National Phase of PCT/US2017/013510, filed on Jan. 13, 2017, which claims priority to and benefit of U.S. Ser. No. 62/278,851, filed on Jan. 14, 2016 and U.S. Ser. No. 62/317,241, filed on Apr. 1, 2016, all of which are incorporated herein by reference in their entirety for all purposes.

STATEMENT OF GOVERNMENTAL SUPPORT

This invention was made with government support under Grant No. AG051386 awarded by the National Institutes of Health. The Government has certain rights in this invention.

BACKGROUND

Extracellular vesicles (EVs) are small membranous vesicles that differ in their cellular origin, abundance and biogenesis (Raposo and Stoorvogel (2013) *J. Cell Biol.* 200: 373-383), and are naturally secreted by almost all cell types to transport bioactive molecules intercellularly. EVs are positive for tetraspanin family proteins, such as CD63, CD81 and CD9 (Mathivanan and Simpson (2009) *Proteomics* 9: 4997-5000 (2009); Bobrie et al. (2012) *Cancer Res.* 72: 4920-4930; Yoshioka et al. (2013) *J. Extracell. Vesicles,* 2: doi:10.3402/jev.v2i0.20424), and contain cell surface proteins as well as both mRNA and microRNA (Valadi et al. (2007) *Nat. Cell Biol.* 9: 654-659).

Macrovesicles called ectosomes (100-1000 nm), apoptotic bodies (>1000 nm), and exosomes together form this pool of EVs which comprises a mixture of multiple subpopulations derived from different tissues and cell types. Detection of specific types of extracellular vesicles, such as exosomes, in a complex mixture, such as blood, is a challenge. Assessment of a tissue-specific subpopulation of exosomes has proven even more difficult.

Blood borne neuron-derived (neuronal) nanoscale extracellular vesicles (nsEVs) have shown substantial potential as "windows into the brain" that enlighten central nervous system (CNS) disorder-associated changes in brain biochemistry and intercellular communication (see, e.g., Federoff et al. (2015) *Alzheimers Dement.* 11: 600-607; Goetzl et al. (2015) *Neurology,* 85(1): 40-47; Goetzl et al. (2015) *Ann. Clin. Transl. Neurol.* 2: 769-773; Kapogiannis et al. (2015) *FASEB J.* 29(2): 589-596; Shi et al. (2014) *Acta Neuropathol.* 128: 639-650; Cheng et al. (2015) *Mol. Psychiatry,* 20: 1188-1196; Lugli et al. (2015) *PLoS One,* 10(10): e0139233).

Conventional methods of analyzing EVs generally require large quantities of EVs to be concentrated and processed via time-consuming immunoblotting or enzyme-linked immunosorbent assay (ELISA) assays. These methods are impractical in most clinical settings.

Moreover an important limitation of the use of extracellular vesicles in diagnostic and/or prognostic methods has been that detection methods have required the presence for disease-related markers that are specific or highly enriched in certain tissue or tumor types.

SUMMARY

Various embodiments contemplated herein may include, but need not be limited to, one or more of the following:

Embodiment 1: A method of identifying and/or quantifying one or more antigens of interest (biomarkers) on the surface of cell- or tissue-specific exosomes, said method comprising:
  i) incubating a population of exosomes obtained from a biological fluid with a one or more tissue-specific antibodies that bind an antigen specific to a tissue or cell type of interest that produces exosomes, where said tissue specific antibodies are attached to acceptor beads and said incubating is under conditions where said tissue-specific antibodies bind exosomes displaying said antigen;
  ii) isolating exosomes bound by said tissue specific antibodies to produce isolated tissue-specific exosomes;
  iii) incubating a test subset of said isolated tissue-specific exosomes with acceptor beads attached to test antibodies that bind an antigen of interest under conditions where said antibodies that bind an antigen of interest bind to exosomes that display said antigen of interest;
  iv) incubating a control subset of said isolated tissue-specific exosomes with negative control acceptor beads under the same conditions as in step iii where the concentration of control acceptor beads is about the same as the concentration of the acceptor beads attached to an antibody that bind a marker of interest;
  v) incubating said test subset of isolated exosomes and said control subset of said exosomes with an antibody that binds an exosome specific antigen where said antibody is attached to a donor that produces singlet oxygen when illuminated;
  vi) detecting a signal produced upon illumination of said control subset and said test subset where said signal is produced by reaction of the negative control acceptor beads and/or the acceptor beads attached to test antibodies; and
  vii) identifying the presence or quantifying said antigen(s) of interest, wherein said identifying or quantifying comprises determining the difference in signal produced upon illumination of said test subset and said control subset.

Embodiment 2: The method of embodiment 1, wherein said method further comprises normalizing said difference to the signal level produced by the control subset.

Embodiment 3: The method according to any one of embodiments 1-2, wherein said biofluid comprises a biofluid selected from the group consisting of blood or blood plasma, lymph, cerebrospinal fluid, vitreous humor, sweat, breast milk, semen, tears, saliva, and urine.

Embodiment 4: The method according to any one of embodiments 1-3, wherein said isolating exosomes bound by said tissue specific antibodies to produce isolated tissue-specific exosomes comprises isolation by centrifugation.

Embodiment 5: The method according to any one of embodiments 1-4, wherein said exosomes are obtained from a biological fluid diluted with blocking buffer containing protease and phosphatase inhibitors and no detergent.

Embodiment 6: The method according to any one of embodiments 1-5, wherein said incubation in step (i) is performed for a period of time ranging from about 0.5 or from about 1 hour, or from about 2 hours up to about 48 ours, or up to about 36 hours, or up to about 24 hours, or up to about 12 hours, or up to about 8 hours.

Embodiment 7: The method according to any one of embodiments 1-6, wherein step (i) is performed at a temperature of about 4° C.

Embodiment 8: The method according to any one of embodiments 1-7, wherein said tissue specific antibodies comprise antibodies that bind an antigen specific to a cell type or tissue selected from the group consisting of neural tissue and/or brain tissue, heart, lung, liver, stomach, kidney, pancreas, prostate, large intestine, small intestine, eye, spleen, pituitary gland, colon, and bladder.

Embodiment 9: The method of embodiment 8, wherein said tissue specific antibodies comprise antibodies that bind an antigen specific to brain and/or neural tissue.

Embodiment 10: The method of embodiment 9, wherein said tissue specific antibodies comprise antibodies that bind to an antigen selected from the group consisting of NCAM, nestin, and musashi-1.

Embodiment 11: The method according to any one of embodiments 1-10, wherein said acceptor beads attached to test antibodies comprise acceptor beads attached to an antibody that binds a marker of Alzheimer's disease.

Embodiment 12: The method of embodiment 11, wherein said acceptor beads are attached to an antibody that binds a marker selected from the group consisting of P-S396-tau, P-T181-tau, Aβ, Aβ1-42, and sAPPα.

Embodiment 13: The method according to any one of embodiments 1-10, wherein said acceptor beads attached to test antibodies comprise acceptor beads attached to an antibody that binds a marker of Parkinson's disease.

Embodiment 14: The method of embodiment 13, wherein said acceptor beads attached to test antibodies comprise acceptor beads attached to an antibody that binds to α-synuclein.

Embodiment 15: The method according to any one of embodiments 1-10, wherein said acceptor beads attached to test antibodies comprise acceptor beads attached to an antibody that binds a marker for multiple sclerosis.

Embodiment 16: The method of embodiment 15, wherein said acceptor beads are attached to an antibody that binds myelin basic protein (MBP).

Embodiment 17: The method according to any one of embodiments 1-10, wherein said acceptor beads attached to test antibodies comprise acceptor beads attached to an antibody that binds a marker for a sleep disorder.

Embodiment 18: The method of embodiment 17, wherein said acceptor beads are attached to an antibody that binds orexin.

Embodiment 19: The method according to any one of embodiments 1-10, wherein said acceptor beads attached to test antibodies comprise acceptor beads attached to an antibody that binds to a cancer marker.

Embodiment 20: The method of embodiment 19, wherein said acceptor beads attached to test antibodies comprise acceptor beads attached to an antibody that binds to a cancer marker selected from the group consisting of Caveolin-1, EpCAM, FasL, TRAIL, Galectine3, CD151, Tetraspanin 8, EGFR, RPN2, CD44, CD47, CA15-3, CA27.29, CA19-9, CA-125, carcinoembryonic antigen (CEA), CD20, chromogranin A (CgA), cytokeratin fragments 21-1, HER4, HER2/neu, and TGF-13.

Embodiment 21: The method of embodiment 19, wherein said acceptor beads attached to test antibodies comprise acceptor beads attached to an antibody that binds to a marker for glioma.

Embodiment 22: The method of embodiment 21, wherein said acceptor beads attached to test antibodies comprise acceptor beads attached to an antibody that binds to a marker selected from the group consisting of epidermal growth factor receptor type III variant (EGFRvIII), and isocitrate dehydrogenase 1 (IDH1) Arg132 mutant.

Embodiment 23: The method according to any one of embodiments 1-22, wherein said negative control acceptor beads comprise acceptor beads without an antibody attached thereto.

Embodiment 24: The method according to any one of embodiments 1-22, wherein said negative control acceptor beads comprise acceptor beads attached to a non-specific antibody or to an antibody specific for a target that is not present in the assay system.

Embodiment 25: The method according to any one of embodiments 1-24, wherein the antibody that binds an exosome specific antigen comprise an antibody that binds an exosome-specific antigen selected from the group consisting of CD63, CD9, CD81, hsp70, CD37, CD53, CD82, CD13, CD11, CD86, ICAM-1, Rab5, Annexin V, and LAMP1. CD-31, HLA-G, and Rab5bT.

Embodiment 26: The method according to any one of embodiments 1-25, wherein the donor is attached to antibody before contacting to the exosome.

Embodiment 27: The method according to any one of embodiments 1-25, wherein the antibody that binds the exosome-specific antigen is biotinylated and antibody is first contacted to exosome and then avidin or streptavidin conjugated donor beads are added to the reaction.

Embodiment 28: The method according to any one of embodiments 1-27, wherein biotinylated isotype control antibodies are used to control for non-specific binding.

Embodiment 29: The method according to any one of embodiments 1-28, wherein said method is performed in a multiwell plate and said identifying the presence or quantifying said antigens of interest comprising reading a signal using a plate reader.

Embodiment 30: The method according to any one of embodiments 1-29, wherein said acceptor beads (e.g., AlphaLISA acceptor beads) emit a fluorescent or luminescent signal in response to the present of singlet oxygen.

Embodiment 31: The method of embodiment 30, wherein said acceptor beads comprise a thioxene derivative that derivative that reacts with singlet oxygen to generate a chemiluminescence reaction that transfers energy to fluorophores within the same bead and generate an emission signal.

Embodiment 32: The method according to any one of embodiments in 30-31, wherein said emission signal ranges from about 520 to about 620 nm or is about 615 nm.

Embodiment 33: The method according to any one of embodiments 1-32, wherein said donor beads comprise an alphalisa alpha donor.

Embodiment 34: The method of embodiment 33, wherein said donor comprises a phthalocyanine that excites ambient oxygen to a singlet state when illuminated.

Embodiment 35: The method according to any one of embodiments 1-34, wherein said incubating and isolating comprise a method of purifying a population of exosomes according to any one of embodiments 93-107.

Embodiment 36: A method of identifying and/or quantifying one or more biomarkers on the surface of nanoscale extracellular vesicles (nsEVs), said method comprising:

i) incubating a biological sample comprising a population of nanoscale extracellular vesicles with a first antibody that binds said vesicles or a marker on said vesicles under conditions where said antibody binds said vesicles, where said first antibody is attached to a magnetic particle thereby providing a magnetic particle/vesicle immunocomplex;

ii) isolating said complex from said biological sample;

iii) washing said complex under high stringency wash conditions to remove non-nsEV entities in the biofluid;

iv) incubating said complex with a second antibody that binds to a marker of interest on the nsEV, where said second antibody is attached to a detectable label or is bound by a third antibody attached to a detectable label; and v) detecting the detectable label to indicate the presence or absence or quantity of said biomarker(s) on the surface of said nanoscale extracellular vesicles.

Embodiment 37: The method of embodiment 36, wherein said nanoscale extracellular vesicles comprise ectosomes.

Embodiment 38: The method of embodiment 36, wherein said nanoscale extracellular vesicles comprise exosomes.

Embodiment 39: The method according to any one of embodiments 36-38, wherein said biofluid comprises a biofluid selected from the group consisting of blood or blood plasma, lymph, cerebrospinal fluid, vitreous humor, sweat, breast milk, semen, tears, saliva, and urine.

Embodiment 40: The method according to any one of embodiments 36-39, wherein said a biological fluid is diluted with a blocking buffer containing protease and phosphatase inhibitors and no detergent.

Embodiment 41: The method according to any one of embodiments 36-40, wherein said incubation in step (i) is performed for a period of time ranging from about 0.5 or from about 1 hour, or from about 2 hours up to about 48 hours, or up to about 36 hours, or up to about 24 hours, or up to about 12 hours, or up to about 8 hours.

Embodiment 42: The method according to any one of embodiments 36-41 wherein step (i) is performed at a temperature of about 4° C.

Embodiment 43: The method according to any one of embodiments 36-42, wherein said isolating comprises centrifuging said biological sample and removing said magnetic particles from said sample.

Embodiment 44: The method according to any one of embodiments 36-43, wherein said high stringency conditions comprises a pH ranging from about pH 3 up to about pH 6, or from about pH 4 up to about pH 5.

Embodiment 45: The method of embodiment 44, wherein said high stringency conditions comprises a pH of about pH 5.

Embodiment 46: The method according to any one of embodiments 36-45, wherein said washing comprises filtering said complex.

Embodiment 47: The method of embodiment 46, wherein said filtering comprises filtering said complex through a filter with a pore size of about 0.2 μm.

Embodiment 48: The method according to any one of embodiments 36-47, wherein said first antibody is an antibodies that binds to a cell type or tissue selected from the group consisting of neural tissue and/or brain tissue, heart, lung, liver, stomach, kidney, pancreas, prostate, large intestine, small intestine, eye, spleen, pituitary gland, colon, and bladder.

Embodiment 49: The method of embodiment 48, wherein first antibody comprises an antibody that binds an antigen specific to brain and/or neural tissue.

Embodiment 50: The method of embodiment 49, wherein said first antibody comprises an antibody that binds to an antigen selected from the group consisting of NCAM, nestin, and musashi-1.

Embodiment 51: The method according to any one of embodiments 36-50, wherein said first antibody is an antibody that binds an exosome specific antigen.

Embodiment 52: The method of embodiment 51, wherein said first antibody comprises an antibody that binds an exosome-specific antigen selected from the group consisting of CD63, CD9, CD81, hsp70, CD37, CD53, CD82, CD13, CD11, CD86, ICAM-1, Rab5, Annexin V, and LAMP1, CD-31, HLA-G, and Rab5bT.

Embodiment 53: The method according to any one of embodiments 36-52, wherein said second antibody is an antibody that binds a marker of Alzheimer's disease.

Embodiment 54: The method of embodiment 53, wherein said second antibody binds a marker selected from the group consisting of P-S396-tau, P-T181-tau, Aβ, Aβ1-42, APP, sAPPβ and sAPPα.

Embodiment 55: The method according to any one of embodiments 36-52, wherein said second antibody is an antibody that binds a marker of Parkinson's disease.

Embodiment 56: The method of embodiment 55, wherein second antibody binds to α-synuclein.

Embodiment 57: The method according to any one of embodiments 36-52, wherein said second antibody is an antibody that binds a marker for multiple sclerosis.

Embodiment 58: The method of embodiment 57, wherein second antibody antibody binds myelin basic protein (MBP).

Embodiment 59: The method according to any one of embodiments 36-52, wherein said second antibody is an antibody that binds a marker for a sleep disorder.

Embodiment 60: The method of embodiment 59, wherein said second antibody binds orexin.

Embodiment 61: The method according to any one of embodiments 36-52, wherein said second antibody comprises an antibody that binds to a cancer marker.

Embodiment 62: The method of embodiment 61, wherein said second antibody binds to a cancer marker selected from the group consisting of Caveolin-1, EpCAM, FasL, TRAIL, Galectine3, CD151, Tetraspanin 8, EGFR, RPN2, CD44, CD47, CA15-3, CA27.29, CA19-9, CA-125, carcinoembryonic antigen (CEA), CD20, chromogranin A (CgA), cytokeratin fragments 21-1, HER4, HER2/neu, and TGF-13.

Embodiment 63: The method according to any one of embodiments 36-52, wherein said second antibody binds to a marker for glioma.

Embodiment 64: The method of embodiment 63, wherein second antibody binds to a marker selected from the group consisting of epidermal growth factor receptor type III variant (EGFRvIII), and isocitrate dehydrogenase 1 (IDH1) Arg132 mutant.

Embodiment 65: The method according to any one of embodiments 36-64, wherein said detecting comprises detecting enzyme activity in a multiwell format.

Embodiment 66: The method of embodiment 65, wherein said detecting is performed using a plate reader.

Embodiment 67: The method according to any one of embodiments 36-64, wherein said detecting is performed using surface plasmon resonance detector.

Embodiment 68: The method of embodiment 67, wherein said surface plasmon resonance device comprises a smartphone-based surface plasmon resonance device.

Embodiment 69: The method according to any one of embodiments 36-68, wherein said incubating and isolating comprise a method of purifying a population of exosomes according to any one of embodiments 93-107.

Embodiment 70: A triorthogonal linker said linker comprising:

a first coupling group that before reaction with a functionalized magnetic particle, comprises an alkyne or an azide;

a second coupling group that, before reaction with a biomolecule, comprises a biotin or an NHS-ester (N-hydroxysuccinimide ester) capable of reacting with a free amine in a biomolecule; and a photocleavable core disposed between said first group and said second group.

Embodiment 71: The triorthogonal linker of embodiment 70, wherein said first coupling group comprises an alkyne.

Embodiment 72: The triorthogonal linker of embodiment 70, wherein said first coupling group comprises an azide.

Embodiment 73: The triorthogonal linker according to any one of embodiments 70-72, wherein said second group comprises an NHS-ester.

Embodiment 74: The triorthogonal linker according to any one of embodiments 70-73, wherein said photocleavable core comprises a moiety selected from the group consisting of nitrobenzyl, a nitrophenethyl compound, and their dimethoxy derivatives (e.g., nitroveratryl).

Embodiment 75: The triorthogonal linker of embodiment 70, wherein said linker comprises the structure

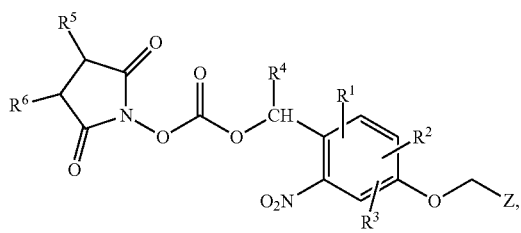

wherein:
$R^1$ is selected from the group consisting of H, —OCH$_3$, CH$_3$, a C$_1$ to C$_5$ alkyl, and a halogen;
$R^2$ is selected from the group consisting of H, —OCH$_3$, CH$_3$, and a halogen;
$R^3$ is selected from the group consisting of H, CH$_3$, a halogen, and a C$_1$ to C$_5$ alkyl;
$R^4$ is selected from the group consisting of H, CH$_3$, a halogen, a C$_1$ to C$_5$ alkyl, and phenyl;
$R^5$ is H or sulfo;
$R^6$ is H or sulfo; and
Z is alkyne or azide.

Embodiment 76: The triorthogonal linker of embodiment 75, wherein $R^4$ is selected from the group consisting of H, CH$_3$, a halogen, and a C$_1$ to C$_5$ alkyl.

Embodiment 77: The triorthogonal linker according to any one of embodiments 75-76, wherein $R^1$ is OCH$_3$.

Embodiment 78: The triorthogonal linker according to any one of embodiments 75-77, wherein $R^2$ is OCH$_3$.

Embodiment 79: The triorthogonal linker according to any one of embodiments 75-78, wherein $R^4$ is CH$_3$.

Embodiment 80: The triorthogonal linker according to any one of embodiments 75-79, wherein $R^4$ is phenyl.

Embodiment 81. The triorthogonal linker of embodiment 75, wherein said linker comprises a structure according to the formula:

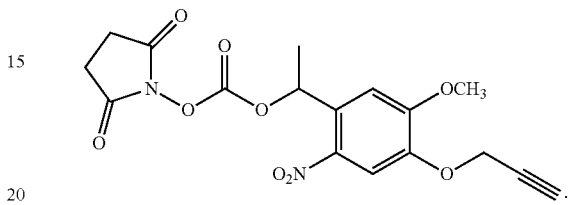

Embodiment 82: The triorthogonal linker of embodiment 75, wherein said linker comprises a structure according to the formula:

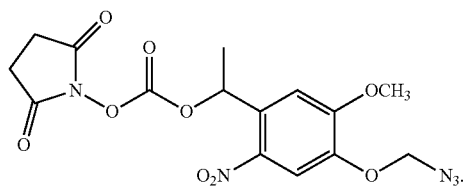 [SMILES: COc1cc(C(C)OC(=O)ON2C(=O)CCC2=O)c([N+](=O)[O-])cc1OCN=[N+]=[N-]]

Embodiment 83: The triorthogonal linker according to any one of embodiments 70-72, wherein said second group comprises a biotin.

Embodiment 84: The triorthogonal linker of embodiment 83, wherein said linker comprises a compound according to the formula:

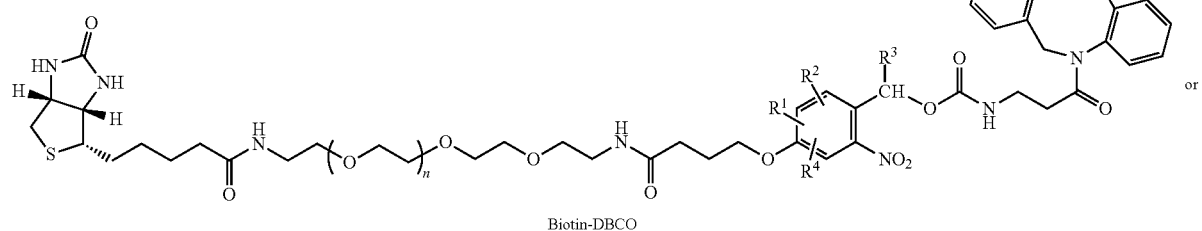

Biotin-DBCO

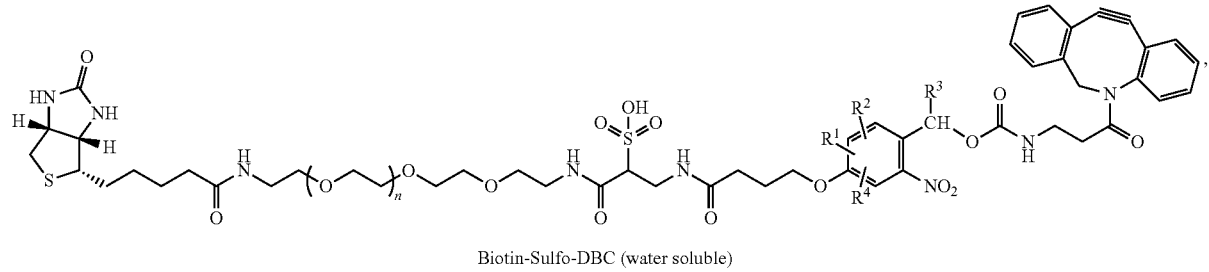

Biotin-Sulfo-DBC (water soluble)

wherein:

n is 1, 2, 3, 4, 5, 6, 7, 8, 9, or 10;

$R^1$ is selected from the group consisting of H, —OCH$_3$, CH$_3$, a C1 to C5 alkyl, and a halogen;

$R^2$ is selected from the group consisting of H, —OCH$_3$, CH$_3$, and a halogen; $R^3$ is selected from the group consisting of H, CH$_3$, a halogen, and a C1 to C5 alkyl;

and $R^4$ is selected from the group consisting of H, CH$_3$, a halogen, and a C1 to C5 alkyl.

Embodiment 85: The triorthogonal linker according to any one of claims 70-84, wherein said linker is bound via reaction of said first coupling group to a functionalized magnetic particle.

Embodiment 86: The triorthogonal linker according to any one of claims 70-85, wherein said linker is bound via reaction of said second coupling group to an antibody.

Embodiment 87: The triorthogonal linker of embodiment 86, wherein said linker is bound to said antibody via reaction of said NHS-ester to an amine on said antibody.

Embodiment 88: The triorthogonal linker of embodiment 86, wherein said linker is bound to said antibody via reaction of said biotin to a streptavidin attached to said antibody.

Embodiment 89: The triorthogonal linker according to any one of embodiments 86-88, wherein said antibody is an antibody that binds an exosome specific antigen.

Embodiment 90: The triorthogonal linker of embodiment 89, wherein said antibody binds an exosome-specific antigen selected from the group consisting of CD63, CD9, CD81, hsp70, CD37, CD53, CD82, CD13, CD11, CD86, ICAM-1, Rab5, Annexin V, and LAMP1, CD-31, HLA-G, and Rab5bT.

Embodiment 91: The triorthogonal linker of embodiment 90, wherein said antibody is an anti-CD9 antibody.

Embodiment 92: The triorthogonal linker of embodiment 90, wherein said antibody is an anti-CD63 antibody.

Embodiment 93: A method of purifying a population of nanoscale extracellular vesicles (nsEVs), said method comprising:

i) providing a triorthogonal linker comprising an antibody that is attached by said linker to a magnetic bead where said linker comprise a photocleavable core disposed between the antibody and the magnetic bead and where said antibody is an antibody that binds a marker displayed on an nsEV;

ii) contacting a biological sample comprising nsEVs with said triorthogonal linker under conditions where said antibody binds to an nsEV in said sample to form a complex comprising a magnetic bead attached by said linker to an nsEV;

iii) utilizing a magnet/magnetic field to isolate said complex from other components in said sample;

iv) exposing said complex to light to cleave said photocleavable core and separate the magnetic bead from the antibody-bound nsEV; and v) utilizing a magnet/magnetic field to separate said magnetic bead from the antibody-bound nsEV to provide a substantially purified population of antibody-bound nsEvs.

Embodiment 94: The method of embodiment 93, wherein said nanoscale extracellular vesicles comprise ectosomes and said substantially purified population is a substantially purified population of ectosomes.

Embodiment 95: The method of embodiment 93, wherein said nanoscale extracellular vesicles comprise exosomes and said substantially purified population is a substantially purified population of exosomes.

Embodiment 96: The method according to any one of embodiments 93-95, wherein said biological sample comprises a biofluid selected from the group consisting of blood or blood plasma, lymph, cerebrospinal fluid, vitreous humor, sweat, breast milk, semen, tears, saliva, and urine.

Embodiment 97: The method according to any one of embodiments 93-96, wherein said a biological sample is diluted with a blocking buffer containing protease and phosphatase inhibitors and no detergent.

Embodiment 98: The method according to any one of embodiments 93-97, wherein said light comprises UV light.

Embodiment 99: The method according to any one of embodiments 93-98, wherein said triorthogonal linker comprises a linker selected from the group consisting of L1, L1a, L2, L3, L4, or L5 shown in FIG. 16 without attached antibody or magnetic bead.

Embodiment 100: The method according to any one of embodiments 93-98, wherein said providing comprises:

providing a triorthogonal linker according to any one of embodiments 70-84;

reacting said linker with a functionalized magnetic particle to couple said magnetic particle to said linker through reaction with said first coupling group; and reacting said linker with an antibody to couple said linker to said antibody through reaction with said second coupling group.

Embodiment 101: The method of embodiment 100, wherein said first coupling group is an alkyne and said magnetic particle is functionalized with an azide and said magnetic particle is linked to said linker by reaction of said alkyne with said azide.

Embodiment 102: The method of embodiment 100, wherein said first coupling group is an azide and said magnetic particle is functionalized with an alkyne and said magnetic particle is linked to said linker by reaction of said azide with said alkyne.

Embodiment 103: The method according to any one of embodiments 100-102, wherein said second coupling group comprises an NHS ester and said linker is bound to said antibody via reaction of said NHS-ester to an amine on said antibody.

Embodiment 104: The method according to any one of embodiments 100-102, wherein said second coupling group comprises a biotin and said linker is bound to said antibody via reaction of said biotin to a streptavidin attached to said antibody.

Embodiment 105: The method according to any one of embodiments 93-104, wherein antibody is an antibody that binds to a cell type or tissue selected from the group consisting of neural tissue and/or brain tissue, heart, lung, liver, stomach, kidney, pancreas, prostate, large intestine, small intestine, eye, spleen, pituitary gland, colon, and bladder.

Embodiment 106: The method of embodiment 104, wherein first antibody comprises an antibody that binds an antigen specific to brain and/or neural tissue.

Embodiment 107: The method of embodiment 105, wherein said first antibody comprises an antibody that binds to an antigen selected from the group consisting of NCAM, nestin, and musashi-1.

Embodiment 108: The method according to any one of embodiments 93-107, wherein said antibody is an antibody that binds an exosome specific antigen.

Embodiment 109: The method of embodiment 108, wherein said first antibody comprises an antibody that binds an exosome-specific antigen selected from the group consisting of CD63, CD9, CD81, hsp70, CD37, CD53, CD82, CD13, CD11, CD86, ICAM-1, Rab5, Annexin V, and LAMP1, CD-31, HLA-G, and Rab5bT.

Embodiment 110: The method of embodiment 109, wherein said antibody is an anti-CD9 antibody.

Embodiment 111: The method of embodiment 109, wherein said antibody is an anti-CD63 antibody.

Embodiment 112: The method according to any one of embodiments 93-111 further comprising:
vi) incubating said antibody-bound nsEVs with a second antibody that binds to a marker of interest on the nsEV, where said second antibody is attached to a detectable label or is bound by a third antibody attached to a detectable label; and
vii) detecting the detectable label to indicate the presence or absence or quantity of said biomarker(s) on the surface of said nanoscale extracellular vesicles.

Embodiment 113: The method of embodiment 112, wherein said detectable label is selected from the group consisting of a colorimetric label, a fluorescent label, a radioactive label, an enzymatic label, and an alphalisa donor or acceptor bead.

Embodiment 114: The method according to any one of embodiments 112-113, wherein said incubation in step (vi) is performed for a period of time ranging from about 0.5 or from about 1 hour, or from about 2 hours up to about 48 hours, or up to about 36 hours, or up to about 24 hours, or up to about 12 hours, or up to about 8 hours.

Embodiment 115: The method according to any one of embodiments 112-114, wherein said second antibody is an antibody that binds a marker of Alzheimer's disease.

Embodiment 116: The method of embodiment 115, wherein said second antibody binds a marker selected from the group consisting of P-S396-tau, P-T181-tau, Aβ, Aβ1-42, APP, sAPPβ and sAPPα.

Embodiment 117: The method of embodiment 115, wherein said second antibody binds Aβ.

Embodiment 118: The method according to any one of embodiments 112-114, wherein said second antibody is an antibody that binds a marker of Parkinson's disease.

Embodiment 119: The method of embodiment 118, wherein second antibody binds to α-synuclein.

Embodiment 120: The method according to any one of embodiments 112-114, wherein said second antibody is an antibody that binds a marker for multiple sclerosis.

Embodiment 121: The method of embodiment 120, wherein second antibody binds myelin basic protein (MBP).

Embodiment 122: The method according to any one of embodiments 112-114, wherein said second antibody is an antibody that binds a marker for a sleep disorder.

Embodiment 123: The method of embodiment 122, wherein said second antibody binds orexin.

Embodiment 124: The method according to any one of embodiments 112-114, wherein said second antibody comprises an antibody that binds to a cancer marker.

Embodiment 125: The method of embodiment 124, wherein said second antibody binds to a cancer marker selected from the group consisting of Caveolin-1, EpCAM, FasL, TRAIL, Galectine3, CD151, Tetraspanin 8, EGFR, RPN2, CD44, CD47, CA15-3, CA27.29, CA19-9, CA-125, carcinoembryonic antigen (CEA), CD20, chromogranin A (CgA), cytokeratin fragments 21-1, HER4, HER2/neu, and TGF-13.

Embodiment 126: The method according to any one of embodiments 112-114, wherein said second antibody binds to a marker for glioma.

Embodiment 127: The method of embodiment 126, wherein second antibody binds to a marker selected from the group consisting of epidermal growth factor receptor type III variant (EGFRvIII), and isocitrate dehydrogenase 1 (IDH1) Arg132 mutant.

Embodiment 128: The method according to any one of embodiments 112-127, wherein said detecting comprises detecting a signal in a multiwell format.

Embodiment 129: The method of embodiment 128, wherein said detecting is performed using a plate reader.

Embodiment 130: The method according to any one of embodiments 112-127, wherein said detecting is performed using surface plasmon resonance detector.

Embodiment 131: The method of embodiment 130, wherein said surface plasmon resonance device comprises a smartphone-based surface plasmon resonance device.

Embodiment 132: The method according to any one of embodiments 112-127, wherein said detectable label comprises an AlphaLisa acceptor bead.

Embodiment 133: The method of embodiment 132, wherein said method comprises providing an AlphaLisa donor bead and detecting the signal produced by interaction of the acceptor bead and the donor bead.

Embodiment 134: The method according to any one of embodiments 132-133, wherein said method is performed in a multiwell plate and said identifying the presence or quantifying said antigens of interest comprising reading a signal using a plate reader.

Definitions

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

Antibodies exist as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region thereby converting the $(Fab')_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Certain preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fvs (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons. The important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405 and 4,956,778). Particularly preferred antibodies should include all that have been displayed on phage (e.g., scFv, Fv, Fab and disulfide linked Fv) (Reiter et al. (1995) *Protein Eng.* 8: 1323-1331).

The term "specifically binds", as used herein, when referring to a biomolecule (e.g., protein, nucleic acid, antibody, etc.), refers to a binding reaction that is determinative of the presence of biomolecule in a heterogeneous population of molecules (e.g., proteins and other biologics). Thus, under designated conditions (e.g., immunoassay conditions in the case of an antibody or stringent hybridization conditions in the case of a nucleic acid), the specified ligand or antibody binds to its particular "target" molecule and does not bind in a significant amount to other molecules present in the sample.

The terms "antigen" or "marker" are used interchangeably to refer to a biomolecule or biomolecule complex, such as proteins, carbohydrates, glycoproteins, and the like present on the surface of a cell or exosome and that can be bound by an antibody specific for that antigen or marker.

A "tissue-specific antibody" is an antibody that binds (e.g., specifically binds) an antigen characteristically present on a specific tissue or cell type (e.g., characteristically present on a tissue such as neural tissue and/or brain tissue, heart, lung, liver, stomach, kidney, pancreas, prostate, large intestine, small intestine, colon, bladder, eye, pituitary, thyroid, spleen, and the like).

A negative control acceptor bead is an acceptor bead lacking an antibody, or an acceptor bead attached to a non-specific antibody, or an acceptor bead attached to an antibody specific to an antigen that is not present in the assay system.

An "exosome-specific antibody" is an antibody that specifically binds an exosome-specific antigen, e.g., CD63, CD9, CD81, hsp70, CD37, CD53, CD82, CD13, CD11, CD86, ICAM-1, Rab5, Annexin V, LAMP1, CD-31, HLA-G, and Rab5bT.

The terms "acceptor" or "acceptor beads" as used herein refer to a moiety (e.g., a bead) comprising one or more compounds that emit a signal in response to the presence of single oxygen, e.g., singlet oxygen generated by the excitation of an excitation label. AlphaLisa acceptor beads typically contain a thioxene derivative that reacts with the singlet oxygen molecule to generate a chemiluminescence reaction. This energy is transferred to fluorophores within the same bead, shifting the emission wavelength, e.g., to 520-620 nm in the case of the AlphaScreen beads and 615 nm with AlphaLISA beads.

An "avidin/biotin" reaction refers to the binding reaction between avidin and biotin. The term also encompasses binding reactions between biotin and avidin variants including, but not limited to streptavidin, neutravidin, CaptAvidin, and the like.

The term "donor" or donor beads, as used herein refer to a moiety (e.g., a bead that comprises one or more reagents that produce singlet oxygen when the reagent(s) are illuminated).

BRIEF DESCRIPTION OF THE DRAWINGS

CD56 (green) is a neuronal surface marker protein. Left panel histograms correspond to analysis of microspheres incubated with phosphate buffer rather than plasma; these histograms show that fluorescent anti-CD9 antibody has little or no propensity to nonspecifically bind antibody-loaded magnetic microspheres. Right panel histograms show that nsEVs in plasma do not nonspecifically bind to negative control antibody-loaded magnetic microspheres. It should be noted that the results depicted in this figure correspond to an experiment that predates our use of Epoxy Dynabeads. The Dynabeads streptavidin M-270 product was used in these studies; magnetic microspheres were loaded with biotinylated antibodies per the manufacturer's instructions. Labeling of Dynabeads-nsEV complexes was performed using phycoerythrin-conjugated anti-CD9 antibody. FIG. 5 presents similar flow cytometry results for immunoprecipitation of salivary nsEVs captured using antibody-loaded Epoxy Dynabeads.

FIG. 27 shows an application of the Exosense technology to detect amyloid precursor protein (APP) on the surface of neuronal exosomes and distinguish multiple sclerosis patient plasma (sample MS) from control plasma (sample 129). Here we used Dynabead-conjugated CD171 antibody as the IP antibody and an antibody against the nsEV marker CD9 or an antibody against APP (AF1168) as the detection antibody. We normalized the AF1168 signal to the CD9 signal. We observe that MS patient plasma results in a much higher AF1168/CD9 signal ratio.

DETAILED DESCRIPTION

In various embodiments methods are provide for the analysis of potential disease-related biomarkers and/or other molecules of interest on the surface of tissue-specific exosomes in blood and other biological fluids. Exosomes are small (from 30 to 130 nm in diameter) extracellular vesicles derived from the endosomal system. In all cell types, late endosomes and multi-vesicular bodies (MVBs) can fuse with the plasma membrane and release intraluminal vesicles (exosomes) to the extracellular space. Exosomes play a role in cell-cell communication and carry information about the biochemical state of their cell of origin. Some exosomes are released from tissues to the bloodstream/other biological fluids (e.g., saliva, cerebrospinal fluid, etc.).

Macrovesicles called ectosomes (100-1000 nm), apoptotic bodies (>1000 nm), and exosomes together form a pool of extracellular vesicles (EVs) comprising a mixture of multiple subpopulations derived from different tissues and cell types. Detection of a specific type of extracellular vesicle, such as exosomes, in a complex mixture, such as blood, is a challenge. Assessment of a tissue-specific subpopulation of exosomes is even more difficult, but this information is extremely useful for obtaining important information about the function of the tissue of the exosomal origin and any disease-related pathology.

The exosomal surface contains multiple membrane-associated proteins, glycosaminoglycans, and lipids, some of which are specific to the cell type of origin. Thus, these molecules can serve as markers for the tissue-specific exosomal subpopulations.

An important limitation of typical AlphaLisa assay methods is that only the disease-related markers, that are specific or highly enriched in certain tissue or tumor types, can be accurately analyzed. Many potential disease-related biomarkers and/or molecules of interest are expressed in more than one cell type/tissue and as a result are present on a variety of exosomal subpopulations. Thus in many cases only selective assessment of the biomarker levels on the pertinent exosomal subpopulation may provide important information about biochemical alterations at the disease site.

AlphaLisa-Based ExoQuant Detection of Markers on Tissue-Specific Exosome Subpopulations.

Figure 1:
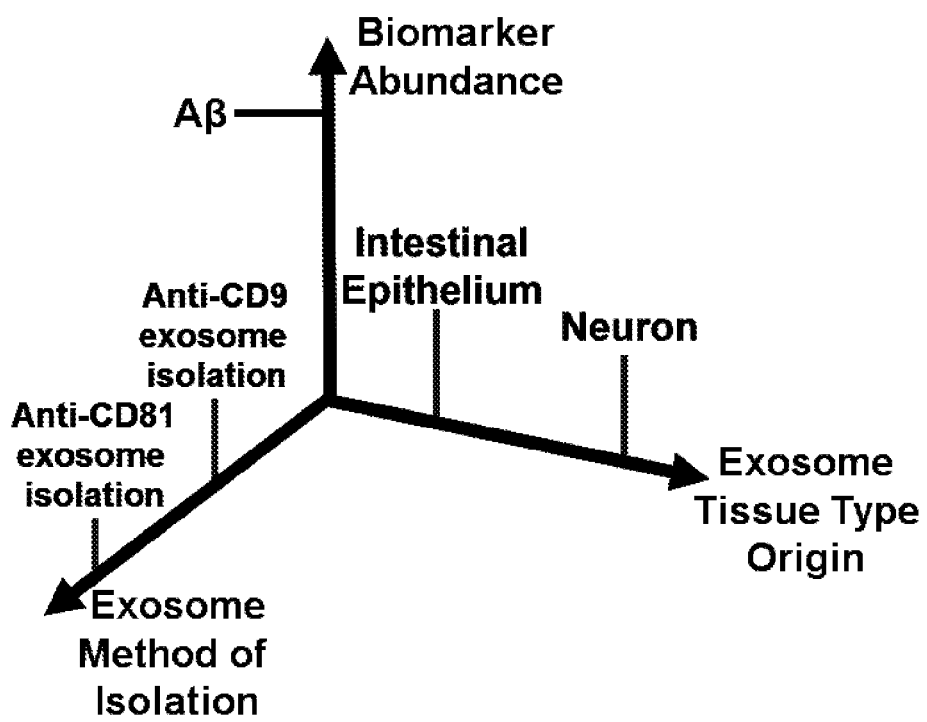
FIG. 1 shows coordinate system illustrating three axes of ExoQuant analysis described herein.

To achieve this high level of specificity, we developed the AlphaLISA-based approach that provides a novel 3-Dimensional (3D) detection method that we call ExoQuant and that allows for determination of disease-related markers on an almost pure tissue-specific exosomal subpopulation. As illustrated in FIG. 1, the method is a "3D" method in which each exosomal analysis dimension axis features multiple points that can define a particular exosomal characterization experiment. For example, the choice of exosomal enrichment method, i.e., size exclusion chromatography (SEC), ultracentrifugation (UC), chemical precipitation (CP), determines the method of isolation axis coordinate. Similarly, as described herein, the specificity of an antibody attached to an acceptor permits the selection of exosomes that derive from a tissue type (cell type) of interest (e.g., neurons) which defines a cell-type axis coordinate. The third exosome analysis dimension, biomarker abundance, differs from the other two dimensions in that biomarker abundance, and thus position on the biomarker abundance axis, is determined by the exosome composition. The researcher chooses which biomarker(s) to quantify and thus defines the biomarker abundance axis label(s). Regardless of whether the researcher quantifies just a few biomarkers, as in validation studies, or quantifies hundreds of candidate biomarkers in omics analyses, the number of exosome phenotype coordinate systems will match the number of quantified biomarker species.

As an example, we implemented the 3D-method for analysis of amyloid beta (Aβ) peptide levels on the surface of brain-specific exosomes from plasma of control subjects and Alzheimer's Disease (AD) patients and found it to correlate with disease diagnosis. The methods described herein open up wide possibilities for the creation of early, non-invasive tests for neurological and other disorders, for diagnosis, and for monitoring of drug treatment effects in biofluids such as blood. Furthermore, the tissue-specific exosomal population can be analyzed for identification of novel targets leading to new therapeutic approaches such as in AD.

Basic Analysis Method.

In one illustrative, but non-limiting embodiment, the Perkin Elmer AlphaLISA protocol was modified to detect and evaluate levels of markers of interest on the surface of tissue-specific exosomes from biological fluids. AlphaLISA technology is based on the detection of the signal coming from acceptor beads (A) if energy is transferred to them from donor beads (D) by singlet oxygen upon excitation of the donor beads with a certain wavelength of light. This occurs when D and A come to close proximity, for example, by binding to the same analyte or by binding different analytes present on a common substrate (e.g., a common exosome). In our new 3D method the analyte is the exosomes.

It will be noted that while the method is described with respect to the ALPHALISA® system, the same method can be used with various fluorescent resonance energy transfer (FRET) systems. FRET systems exploit distance-dependent interactions between the electronic excited states of two dye molecules in which excitation is transferred from a donor molecule to an acceptor molecule without emission of a photon. The absorption spectrum of the acceptor typically overlaps the fluorescence emission spectrum of the donor to produce the FRET interaction. Numerous suitable FRET pairs are known to those of skill in the art (see, e.g., Table 1). It will be recognized that in certain embodiments the FRET donors and/or acceptors can be attached to antibodies or in certain embodiments can be incorporated into/on beads attached to antibodies.

TABLE 1

Illustrative donor/acceptor pairs for FRET.

| Donor | Acceptor |
|---|---|
| 7-Methoxycoumarm | DABCYL |
| Amino Methyl Coumarin | DABCYL, QSY-35 |
| Blue Fluorescent Protein | Ds Red Fluorescent Protein |
| BODIPY-FL$^{2-}$ | DABCYL, QSY-7, QSY-9, BHQ-1 |
| B-Phycoerythrin | Cy5 |
| Carboxyfluorescein Succinimidyl Ester | Texas Red |
| Cascade Blue | DABCYL |
| Coumarin | DABCYL |
| Cy3 | Cy5, QSY-7, QSY-9, BHQ-2 |
| Cy5 | Cy5.5, QSY-35, BHQ-2 |
| Dansyl | FITC |
| Dansyl | Octadecylrhodamine |
| Dialkylaminocoumarin | DABCYL, QSY-35 |
| EDANS | DABCYL |
| FITC | Eosin Thiosemicarbazide |
| Fluorescein | Tetramethylrhodamine |
| Green Fluorescent Protein | Yellow Fluorescent Protein |
| IAEDANS | DDPM |
| Marina Blue | DABCYL, QSY-35 |
| Pacific Blue | DABCYL, QSY-35 |
| Rhodamine 6G | Malachite Green |
| Tryptophan | Dansyl |

Figure 2:
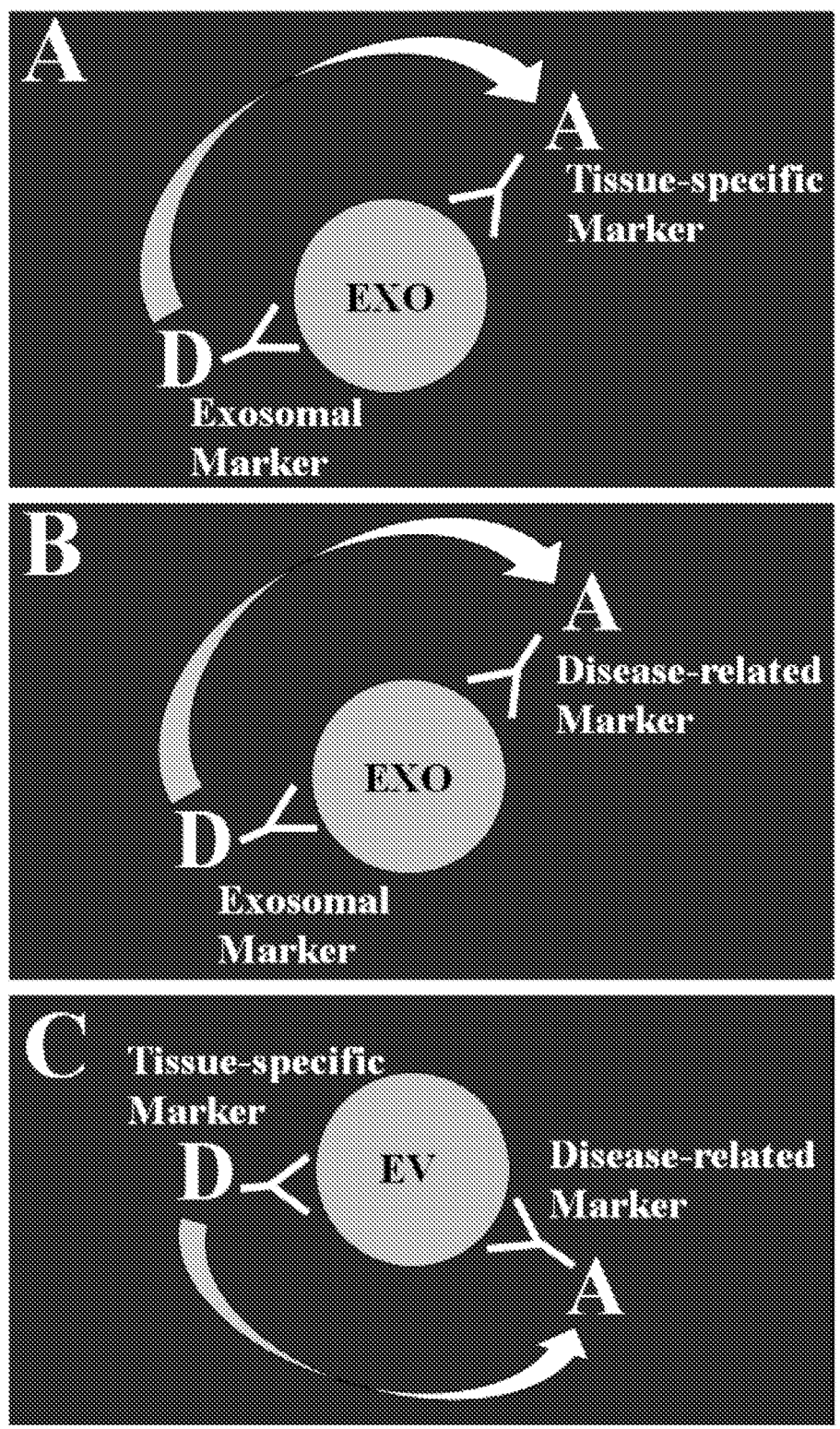
FIG. 2, panels A-C, illustrate typical AlphaLisa assays, and FIG. 2, panel D illustrates the 3D ExoQuant method for exosome analysis.

FIG. 2 illustrates limitations of typical AlphaLisa assays (FIG. 2, panels A-C) in comparison to one embodiment of the new methods described herein (FIG. 2, panel D). Specifically as illustrated in FIG. 2, panels A-C, previous AlphaLisa analyses allow for the detection of a maximum of only two different markers on, for example, an exosome surface (see, e.g., Yoshioka et al. (2014) Nat. Commun. 5: 3591), which leads to either a lack of ability to detect many possible non-cell type-specific markers of interest (FIG. 2, panel A) or a lack of specificity for the exosome tissue origin (FIG. 2, panel B) and the EV type (exosomes vs ectosomes vs apoptotic bodies, FIG. 2, panel C).

A classical approach to address this problem would be the addition of an immunoprecipitation (IP) step, followed by elution of exosomes from the IP beads and 2D-detection. However we found that it is impossible to preserve the integrity of the exosomes and conformations of their surface antigens (both of which are important for the subsequent AlphaLISA exosome detection) during elution.

It was discovered that using AlphaLISA beads conjugated to antibodies against a tissue-specific marker for an isolate (immunoprecipitation) step allows us to overcome these difficulties. We avoid the elution step and isolate the signal from the marker of interest on the specific subset of exosomes by comparison of signal intensity from the pure tissue-specific exosomal population (S1) and intensity of the cumulative signal (S2) from tissue-specific marker and marker of interest bound to acceptor beads, driven by donor beads bound to an exosomal marker (FIG. 2, panel D).

The basic protocol for 3-D ExoQuant assay using AlphaLisa can be divided into five consecutive steps as described below.

Step 1: Isolation of tissue/cell type-specific EVs from biological fluid:

The biological fluid of interest can be diluted in blocking buffer with protease and phosphatase inhibitors. To preserve the integrity of the exosomes the buffer preferably does not contain detergents. Acceptor beads with conjugated tissue-specific antibodies are added to the diluted biological fluid and incubated, e.g., from about 0.5 or from about 1 hour, or from about 2 hours up to about 48 hours, or up to about 36 hours, or up to about 24 hours, or up to about 12 hours, or up to about 8 hours. In certain embodiments the incubation is from a couple of hours to overnight at 4° C. This step can be performed either in the AlphaLISA plate or in separate depending upon the volume of biological fluid required to achieve a detectable signal from the tissue-specific exosomal population. In addition to the isolation of tissue-specific exosomes, this step helps to decrease the profound matrix effect noticed in some biofluids, for example blood plasma.

Since different exosomes of the same origin can express different cell-specific markers, to collect a whole spectrum of the tissue-derived exosomes a pan-tissue specific mixture of antibodies conjugated to acceptor beads can be used. This approach increases sensitivity, especially if a low level of tissue-specific markers is present on exosomes of a particular origin. However, this typically involves careful estimation and equilibration of the amount of acceptor beads since it may create steric problems for binding of the other antibodies in steps 2 and 3 described below. Thus, in certain embodiments pan-tissue specific markers are avoided.

Buffer composition, sample dilution ratio, and incubation time can vary for different biological fluids and different exosomal subpopulations. Detailed conditions for brain-specific exosome isolation from plasma samples are described in Example 1 below.

AlphaLISA beads with immobilized material are pulled out from the solution, for example, by centrifugation at 16,000×g for 15 min, washed 3 times with blocking buffer and diluted in a small amount blocking buffer to achieve a desirable concentration of acceptor beads for step 2.

Step 2: Recognition of biomarkers of interest on the surface of tissue-specific EVs.

This step can be performed in the AlphaLISA plate, preferentially a low-binding plate. 3D-analysis involves separate detection of the exosomal tissue-specific signal (reaction 1) and the cumulative signal from a tissue-specific marker and a marker of interest (reaction 2). Equal amounts of AlphaLISA acceptor beads with immobilized tissue-specific EVs from step 1 are incubated with negative control acceptor beads (reaction 1) (e.g., beads with no antibody, or beads with a non-specific antibody, or beads with an antibody specific for an antigen not present in the analysis system), or with an equal amount of acceptor beads conjugated with antibodies against a marker of interest (reaction 2). Typically the total concentration of acceptor beads is the same in both reactions and, in certain embodiments, does not exceed 15 µg/ml final concentration to avoid a non-specific signal.

Step 3: Recognition of exosomal markers on the surface of tissue-specific EVs.

Equal amounts of biotinylated antibodies against exosomal markers (e.g., CD63, CD9, CD81, hsp70, CD37, CD53, CD82, CD13, CD11, CD86, ICAM-1, Rab5, Annexin V, LAMP1, CD-31, HLA-G, Rab5bT, or others) are added to reaction 1 and reaction 2 and incubated to permit binding of the antibodies to the exosomal markers (e.g., for 1 hour at room temperature). In certain embodiments the final concentration of biotinylated antibodies can vary from 1-5 nM according to the manufacturer's recommendations.

Step 4: Biotin-Streptavidin reaction

Equal amounts streptavidin coated donor beads are added to reaction 1 and reaction 2 to achieve a final donor bead concentration of, for example, about 40 µg/ml and incubated to permit binding of the donor beads to the biotinylated antibodies (e.g., for 30 minutes).

Step 5: Detection of 3D signal

Signals from reaction 1 (S1) and reaction 2 (S2) can be detected using a plate reader (e.g., Perkin Elmer's Enspire Plate Reader or another comparable plate reader) and the relative amount of the molecule of interest on the surface of tissue-specific exosomes can be determined by the difference in signal between S2 and S1. In certain embodiments the value is normalized to the S1 signal using, for example, the formula: (S2-S1)/S1.

In certain embodiments steps 3 and 4, above, can be combined into one step if the exosome-specific antibodies are directly conjugated to the AlphaLISA donor beads. Moreover, the order of surface marker recognition can be changed, but the proposed order helps to maximize yield of tissue-specific exosomes and minimize steric issues. For simplicity only antibodies were mentioned as specific binders in the basic protocol, but in addition to the conventional antibodies other types of binders can be used, for example single chain antibody fragments, designed ankyrin repeat proteins, aptamers, lectins, etc.

These methods are illustrative and not limiting. Using the teachings provided herein, especially in the examples, numerous variations of the basic protocol will be available to one of skill in the art.

Biological Sample.

In this regard, it is noted for example, that there is no particular limitation on the biological sample, and examples thereof include, but are not limited to, blood or blood plasma, lymph, cerebrospinal fluid, vitreous humor, sweat, breast milk, semen, tears, saliva, and urine. Examples of blood samples include whole blood, blood serum, and blood plasma. Among them, in certain embodiments, blood serum is particularly useful.

In various embodiments the sample is a liquid specimen because the liquid specimen is easy to obtain and handle. With respect to the sample, for example, a specimen that has not been diluted can be used directly as a liquid specimen or a diluent obtained by suspending, dispersing, or dissolving a specimen in a solvent can be used as a liquid specimen.

There is no particular limitation on the buffer solutions, and examples thereof include conventionally known buffer solutions used in the isolation of exosomes. In certain embodiments the buffer/diluent solutions are blocking buffers containing protease and phosphatase inhibitors and no detergent.

There is no particular limitation on the amount of the sample to be used.

Defining Features of Exosomes.

Exosomes are manufactured within multivesicular bodies (MVBs), cytoplasmic vesicles that have diameters in the 250-1,000 nm range (Nagashima et al. (2014) *J. Gen. Virol.* 95: 2166-2175; Von Bartheld and Altick (2011) *Prog Neurobiol.* 93: 313-340), and are formed by inward budding of late endosomes (Urbanelli et al. (2013) *Genes* (Basel). 4: 152-170). Exosome diameters typically range from 50-200 nm (Cocucci and Meldolesi (2015) *Trends Cell Biol.* 25:364-372) and their surfaces may be enriched in tetraspanin marker proteins CD9, CD63, and CD81, as well as heat shock proteins such as Hsp70 (Multhoff and Hightower (2011) *Cell Stress Chaperones.* 16:251-255; Ghosh et al. (2014). *PLoS One.* 9(10): e110443). Exosomes can carry high interior levels of Tsg101 and Alix, two proteins comprising the Endosomal Sorting Complexes Required for Transport (ESCRT) machinery involved in intracellular vesicle formation processes (Cocucci and Meldolesi (2015) *Trends Cell Biol.* 25:364-372).

Conversely, ectosomes are vesicles with diameters ranging from 100 nm to 1 micron that bud off from cell plasma membranes. Others have categorized ectosomes into a number of somewhat ambiguous subclasses: shedding vesicles, microvesicles, exosome-like vesicles, nanoparticles, microparticles, and oncosomes (Id.). Although it had been believed that tetraspanin proteins were exosome-specific surface markers more recent analyses have revealed that tetraspanins appear on the surfaces of both exosomes and ectosomes (Andreu and Yáñez-Mó (2014) *Front Immunol.* 5: 442).

Apoptotic bodies, vesicles with diameters of 1-5 microns, are secreted from dying cells during the execution of programmed death mechanisms (Hristov et al. (2004) *Blood*, 104: 2761-2766). Apoptotic bodies differ from extracellular vesicles in that they are not known to migrate from the central nervous system (CNS) into the bloodstream (Shi et al. (2014) *Acta Neuropathol.* 128: 639-650).

Methods of isolating exosomes are known to those of skill in the art (see, e.g., U.S. Patent Pub. Nos: 2015/0290343, 2015/0275301, 2015/0168400, 2015/0104801, 2015/0017660, 2014/0178888, 2013/0273544, and the like).

Tissue-Specific Antibodies Attached to Acceptor Beads.

In various embodiments tissue specific exosomes are obtained by incubating the exosomes with tissue-specific antibodies attached to acceptor beads and then isolating the bound exosomes (e.g., via centrifugation).

The tissue-specific antibodies attached to acceptor beads can comprise antibodies chemically conjugated to acceptor beads or can comprise antibodies attached to acceptor beads using an avidin (streptavidin)/biotin interaction. In certain embodiments the antibody is bound to the acceptor bead before contacting the exosome. In certain embodiments a biotin- or avidin-bearing antibody is contacted to the exosome and the corresponding biotin or avidin acceptor bead is then added and then attaches to the exosome-bound antibody.

In various embodiments the tissue-specific antibodies comprise antibodies that bind to antigens specific to (or preferentially expressed by) a cell type or tissue selected from the group consisting of neural tissue and/or brain tissue, heart, lung, liver, stomach, kidney, pancreas, prostate, large intestine, small intestine, colon, eye, spleen, pituitary gland, thyroid and bladder.

In certain embodiments the tissue-specific antibodies comprise antibodies that bind an antigen specific to brain and/or neural tissue. Brain and/or neural tissue-specific (or preferential) antigens include, but are not limited to NCAM, nestin, musashi-1, accessory protein (AcPb) expressed only in neurons (see, e.g., Lu et al. (2008) *Mol. Immunol.* 45(5): 1374-13 84.), and the like.

Test Antibodies Attached to Acceptor Beads.

In various embodiments the methods described herein involve incubating a test subset of isolated tissue-specific exosomes with acceptor beads attached to test antibodies that bind an antigen of interest (biomarker) under conditions where the antibodies bind to the antigen of interest if it is present on the exosome(s).

There is no particular limit to the antigen of interest. Desirably the antigen of interest is one that is expected to be present on the isolated tissue-specific exosomes.

For example, antigens of interest on exosomes derived from brain and/or neural tissue include, but are not limited to antigens associated with amyloidogenic pathologies (e.g., Alzheimer's disease), antigens associated with Parkinson's disease, and the like. Antigens of interest associated with amyloidogenic pathologies include, but are not limited to P-S396-tau, P-T181-tau, Aβ, Aβ1-42, sAPPα, and the like.

Other antigens associated with various amyloidogenic pathologies include but are not limited to islet amyloid protein (amylin) (IAPP), alpha-synuclein (SNCA), prion (PrP), huntingtin (HTT), calcitonin (Cal), atrial natriuretic factor (ANF), apolipoprotein A1 (ApoA1), serum amyloid a (AA), medin (Med), prolactin (Pro), transthyretin (TTR), lysozyme (Lys), beta 2 microglobulin (β2M), gelsolin (Gel), keratoepithelin (Ker), cystatin (Cys), immunoglobulin light chain AL (AL), S-IBM, cerebrovascular amyloid (CVA), and the like.

In certain embodiments the antigen of interest associated with Parkinson's disease is α-synuclein, although there are other antigens of interest in Parkinson's disease. Antigens for multiple sclerosis include myelin basic protein (MBP). Antigens for sleep disorders include orexin. Antigens for glioma include epidermal growth factor receptor type III variant (EGFRvIII) and isocitrate dehydrogenase 1 (IDH1) Arg132 mutant.

In certain embodiments the antigens of interest comprise antigens associated with a cancer. Such antigens include but are not limited to Caveolin-1, EpCAM, FasL, TRAIL, Galectine3, CD151, Tetraspanin 8, EGFR, RPN2, CD44, CD47, CA15-3, CA27.29, CA19-9, CA-125, carcinoembryonic antigen (CEA), CD20, chromogranin A (CgA), cytokeratin fragments 21-1, HER4, HER2/neu, TGF-13, and the like.

In certain embodiments the test acceptor beads are conjugated to the antibodies that bind the antigen(s) of interest prior to contacting them to the isolated tissue-specific exosomes.

In various embodiments the antibodies are attached to biotin. The antibodies are contacted with the exosomes where they bind the corresponding biomarkers and then acceptor beads conjugated to avidin (e.g., streptavidin) are added to the reaction mix where the beads then bind to the bound antibodies.

Control Acceptor Beads

In various embodiments the methods described herein involve incubating a test subset of isolated tissue-specific exosomes with control (e.g., negative control) acceptor beads. In certain embodiments the control acceptor beads comprise acceptor beads lacking any antibody. In certain embodiments the control acceptor beads comprise acceptor beads attached to a non-specific antibody. In certain embodiments the control acceptor beads comprise acceptor beads attached to an antibody that is specific for an antigen that is not present in the assay system.

Donor Beads.

In various embodiments the methods described herein involve incubating the test subset of isolated tissue-specific exosomes and the control subset of isolated tissue-specific exosomes with an antibody that binds an exosome-specific antigen where the antibody is attached to a donor (e.g., an Alphalisa alpha donor) that produces singlet oxygen when illuminated. In certain embodiments the antibody that binds an exosome-specific antigen comprises an antibody that binds an antigen such as CD63, CD9, CD81, hsp70, CD37, CD53, CD82, CD13, CD11, CD86, ICAM-1, Rab5, Annexin V, LAMP1, CD-31, HLA-G, Rab5bT, and the like.

In certain embodiments the donor beads are conjugated to the antibodies that bind the exosome-specific antigen prior to contacting them to the isolated tissue-specific exosomes.

In various embodiments the antibodies are attached to biotin. The antibodies are contacted with the exosomes where they bind the exosome-specific antigen and then acceptor beads conjugated to avidin (e.g., streptavidin) are added to the reaction mix where the beads then bind to the bound antibodies.

Reading the Signal.

The signal produced by the reactions described herein can be read by methods known to those of skill in the art. In certain embodiments the assay reactions are performed in a multiwall plate and the reaction signal(s) are read using a plate reader (e.g., Perkin Elmer's Enspire plate reader, or other suitable plate reader).

In various embodiments in the ExoQuant method described above, nsEVs (e.g., exosomes) can be isolated/purified using the Exo-Tip methods described below.

ExoSense—High Sensitivity Detection of Extracellular Vesicle Biomarkers in Plasma and Other Biofluids In certain embodiments methods are described herein that employ antibody-coupled magnetic microspheres, for quantifying disease-associated surface marker proteins, or other exosome surface entities such as carbohydrates, on exosomes or other nanoscale extracellular vesicles (nsEVs), particularly ectosomes, isolated from plasma, saliva, cerebrospinal fluid or other biofluids. In various illustrative, but non-limiting embodiments, marker proteins may be quantified using a colorimetric readout, luminescence readout or fluorescent readout.

These methods, designated as "ExoSense" have immediate utility in research applications, e.g., verifying disease-associated biomarkers in the context of disease mechanism or other basic science studies. Modification and also automation of the ExoSense method can lead to diagnostic assay protocols and corresponding hardware that find utility in clinical diagnostics applications as well as possibly in-home diagnostics; the latter would be enabled by smartphone-type devices (see, e.g., Ozcan (2014) *Lab Chip.* 14: 3187-3194; Ludwig et al. (2015) *PLoS One.* 10(8):e0134360; Zhu et al. (2013) *Lab Chip.* 13:1282-1288; Liu et al. (2105) *Sci. Rep.* 5: 12864; Laksanasopin et al. (2015) *Sci. Transl. Med.* (273):273). Although ExoSense studies described herein focus on central nervous system (CNS) disorders, this methodology can be applied to diagnosis and drug efficacy monitoring in the context of cancer, cardiovascular disease and other health conditions.

ExoSense improves upon various methods of quantifying nsEV-associated disease biomarkers in various ways. First, the use of high-stringency wash conditions after the magnetic microsphere-based nsEV immunocapture step ensures that non-nsEV entities in the biofluid of interest, e.g., cell debris, lipoprotein complexes or immunoglobulins, are not enriched along with the desired nsEV population. Additionally, in certain embodiments, as opposed to quantifying nsEV biomarker abundance using flow cytometry, ExoSense can use an ELISA-type multiwell microplate readout format.

Use of this ELISA-type format allows one to employ enzyme-conjugated antibodies, such as horseradish peroxidase, for biomarker detection. Use of such enzyme conjugates provides biomarker abundance signal amplification that cannot be achieved with fluorescent labeling approaches typically described for flow cytometric quantification of nsEV surface proteins. The ExoSense approach does not require prior enrichment, using methods such as chemical precipitation, of nsEVs from the biofluid of interest. To the contrary, satisfactory outcomes with ExoSense have been obtained absent any upstream nsEV enrichment procedures. nsEVs can be immunoprecipitated from plasma, saliva or other biofluids using magnetic particles after, for example, centrifuging the biofluid and, in certain embodiments, passing the supernatant through a 0.2 micron filter. An illustrative, but non-limiting embodiment of this procedure is described below.

Figure 4:
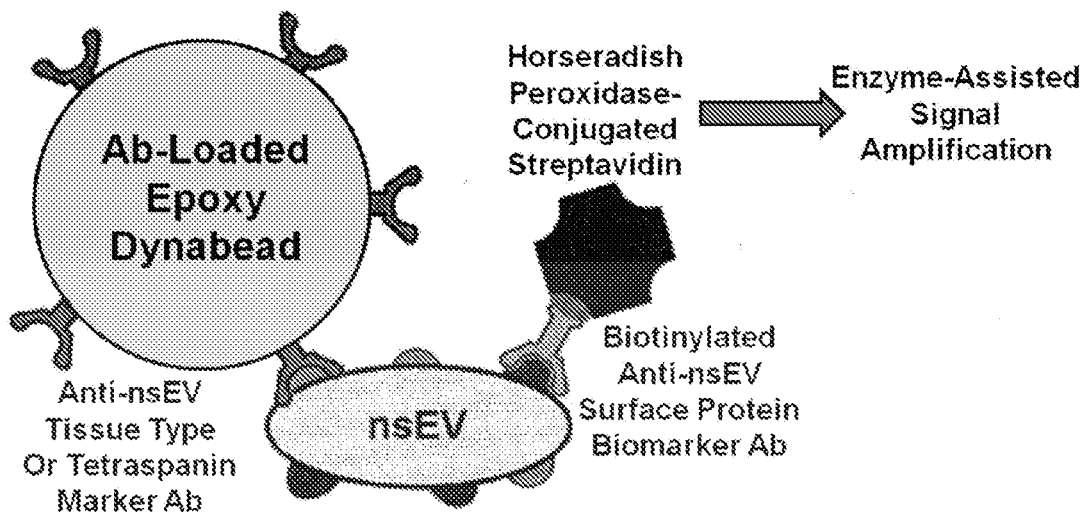
FIG. 4. ExoSense nsEV magnetic microsphere (we have typically used Dynabeads from Life Technologies) capture and detection schematic. User is free to couple whatever antibody might be desired onto magnetic particle and also has flexibility in choosing the detection antibody. nsEV surface marker proteins are quantified using either colorimetric, luminescent or fluorescent horseradish peroxidase (HRP) substrates. It is also possible to use lanthanide-conjugated streptavidin to facilitate the use of time-resolved fluorescence in a microwell plate format for nsEV surface marker quantification.

An illustration of the ELISA-type antibody sandwich approach utilized in the ExoSense assay for quantification of nsEV surface markers appears in FIG. 4. Although it might be possible to use other magnetic microspheres for nsEV capture, satisfactory results were obtained using the Dynabeads epoxy magnetic microsphere product from Life Technologies (Grand Island, N.Y.). This product allows the user to covalently couple any desired antibody to the surface of the Dynabeads magnetic microspheres via an overnight incubation.

We have generally prepared antibody-coupled Dynabeads in 5 mg batches per a slightly modified version of the manufacturer's protocol. With respect to this modification, we have preceded the manufacturer's recommended washing steps with a ten-minute incubation, with tumbling on a lab mixer, of Dynabeads in low pH (pH less than 3) buffer such as glycine-HCl or Pierce's IgG elution buffer.

For carrying out ExoSense with plasma specimens, 500 µL of phosphate buffered saline were added to each ml of plasma specimen after a rapid thaw of frozen plasma in a 37° C. water bath. The diluted plasma was then centrifuged at 13,000 rcf for twenty minutes and the resulting supernatant filtered through a 0.2 micron polyethersulfone (PES) membrane (Pall Life Sciences, Washington, N.Y.) using a disposable plastic syringe.

Seven µL of resuspended Dynabeads magnetic microspheres were then added to 700 µL of filtered, diluted plasma and nsEV immunoprecipitation was allowed to proceed overnight at 4° C. with rotation on a lab mixer. The above procedure can be performed exactly as written in seeking to quantify biomarkers on nsEVs in saliva, cerebrospinal fluid, cell culture media, and presumably other biofluids such as urine.

Immunoprecipitation was followed by four washes: one minute in PBS with 0.1% bovine serum albumin (BSA), ten minutes with rotation on a lab mixer in the low pH buffer noted above, a repeat of this low pH wash step, and final one-minute wash in PBS/0.1% BSA. Between each wash step magnetic microspheres are drawn to the side of the 1.5 ml microcentrifuge tubes in which all incubations are carried out using a Dynamag and the wash supernatant is removed by pipetting. Five-hundred µL of wash buffer are used for each wash step. For saliva, we observed that washing in pH 3 buffer removed all nsEVs from the Dynabeads; carrying out the ten-minute washes in 25 mM phosphate-citrate buffer, pH 5.0, provides a desirable balance between satisfactory nsEV capture and low nonspecific adsorption of nsEVs to Dynabead surfaces (see, e.g., FIG. 5).

Labeling of magnetic microsphere-nsEV complexes can be carried out in 500 µL of PBS/2.5% BSA. Biotinylated antibody concentration can be adjusted depending on the biotinylated antibody being used as some antibodies are more prone to nonspecific binding to Dynabeads than are others. We have found that 0.5 micrograms of antibody per 500 µL of labeling buffer is a good starting point and typically results in acceptably low background signals after incubation of antibody with negative control antibody-coupled Dynabeads and subsequent quantification of nsEV surface marker proteins.

In one illustrative, but non-limiting embodiment, antibody labeling proceeds on a lab rotator for two hours at room temperature and can be followed by three one minute wash steps: PBS/1% BSA, PBS/0.1% BSA and a repeat of the second-step. After the first wash step and resuspension in PBS/0.1% BSA Dynabeads can be transferred to a new microfuge tube to minimize carryover of unbound biotinylated antibody; such carryover can increase background signal upon quantifying nsEV surface marker proteins.

Secondary Dynabeads-nsEV complex labeling can be performed using, e.g., a 1:2000 dilution of 1 mg/ml stock horseradish peroxidase-conjugated streptavidin; the dilution buffer is PBS/2.5% BSA. After 30 minutes of rotation in the dark at room temperature, Dynabeads are washed using the three wash, single microfuge tube transfer process described above. Care is taken to completely remove all of the wash buffer after the final wash step.

Washing of the post-secondary label magnetic microspheres can be followed by resuspension of the Dynabeads in 65 µL of PBS. Duplicate nsEV surface protein measurements can be made for each immunoprecipitation. In one illustrative embodiment, for each measurement, 20 µL of the resuspended Dynabeads are diluted with 20 µL of PBS in a new microfuge tube and then 100 µL of Ultra TMB ELISA Substrate (Pierce, Grant Island, N.Y.) are added to each of these tubes. Tubes are vortexed 2-4 times at intervals throughout a 15-minute substrate development period during which the substrate goes from being transparent to taking on a blue color. After 15 minutes of substrate development, 140 µL of 2N sulfuric acid are added to each microfuge tube to halt the color development.

Tubes are subsequently centrifuged, e.g., at 13,000 rcf for two minutes to pellet Dynabeads and 200 µL of supernatant are transferred to a clear 96-well plate. Absorbances for each well at 450 nm, which are proportional to the amount of ELISA substrate that has been converted by horseradish peroxidase, can be subsequently measured using a microplate reader. Absorbance values (typically around 0.05 absorbance units) for a blank well containing 200 ul of a 2.5:1 (v/v) mixture of ELISA substrate and PBS are subtracted from the absorbance values for each nsEV immunoprecipitation substrate development reaction supernatant and the data analyzed to determine the relative amounts of nsEV biomarker that has been captured in each immunoprecipitation.

Figure 5:
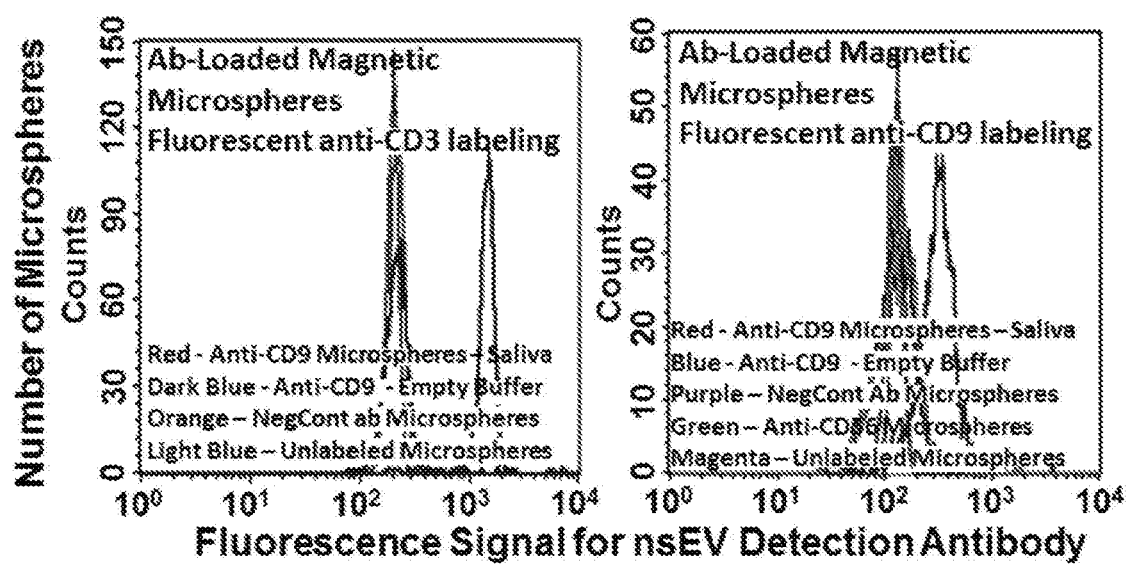
FIG. 5 shows flow cytometry histograms demonstrating the ability to specifically enrich nsEVs from saliva via antibody-loaded magnetic microsphere (Dynabeads Epoxy) immunoprecipitation. After incubation of magnetic microspheres in saliva, antibody-loaded magnetic microsphere-nsEV complexes were labeled with fluorescent anti-CD63 (left panel) or anti-CD9 (right panel) Abs for flow cytometric analysis. Y-axis denotes number of microsphere events counted by cytometer. X-axis denotes anti-nsEV tetraspanin marker antibody fluorescence. Legends in lower left corner of histograms denote antibodies loaded onto magnetic microspheres. Anti-CD9 Ab-loaded microspheres were incubated with both saliva and empty buffer with the latter incubation serving as a negative control for fluorescent anti-tetraspanin antibody labeling.
Figure 6:
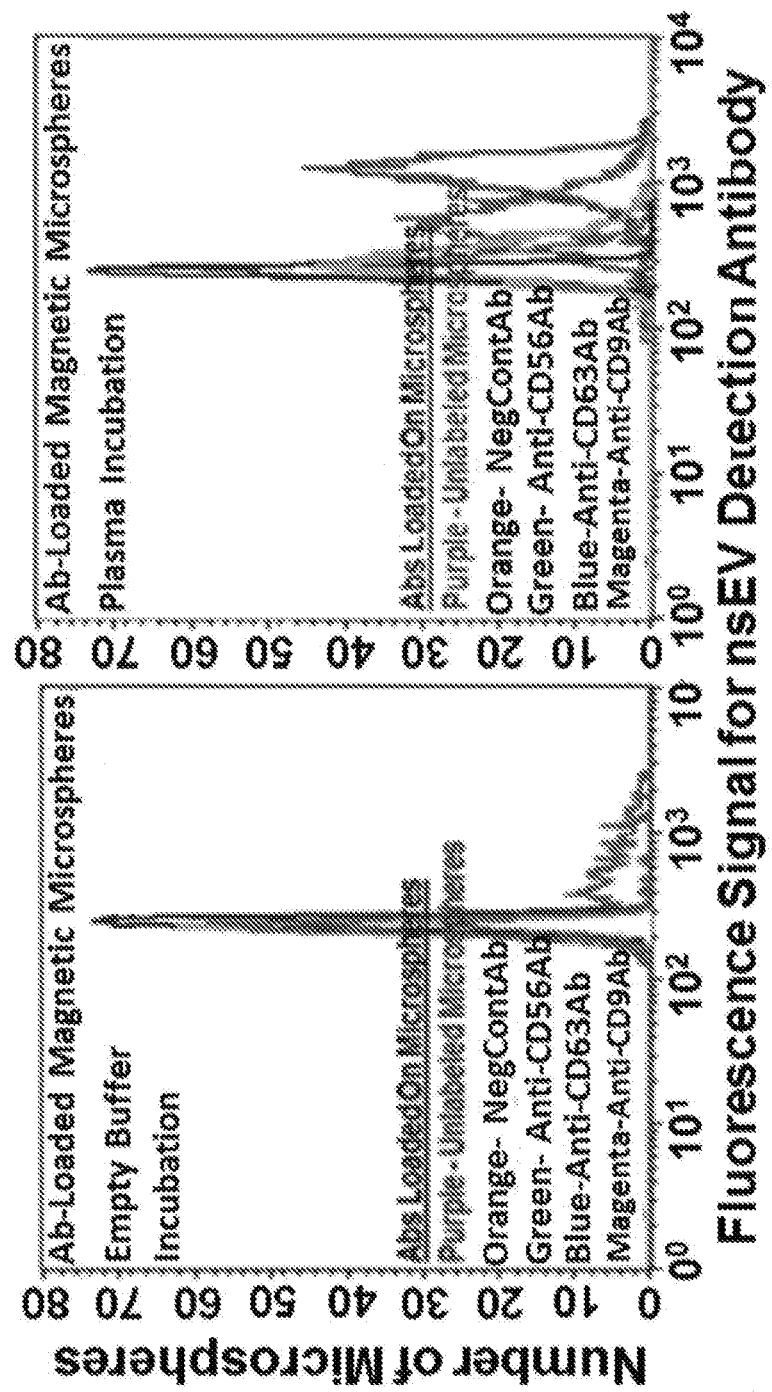
FIG. 6 provides flow cytometry histograms showing ability to specifically enrich nsEVs from plasma via antibody loaded magnetic microsphere immunoprecipitation. After incubation of microspheres in plasma, antibody-loaded magnetic microsphere-nsEV complexes were labeled with fluorescent anti-CD9 (nsEV marker) antibody for flow cytometric analysis. Y-axis denotes number of magnetic particle events counted by cytometer. X-axis denotes anti-CD9 antibody fluorescence. Legends in lower left corner of histograms denote antibodies loaded onto magnetic microspheres. CD63 (blue) is a tetraspanin nsEV marker protein.
Figure 7:
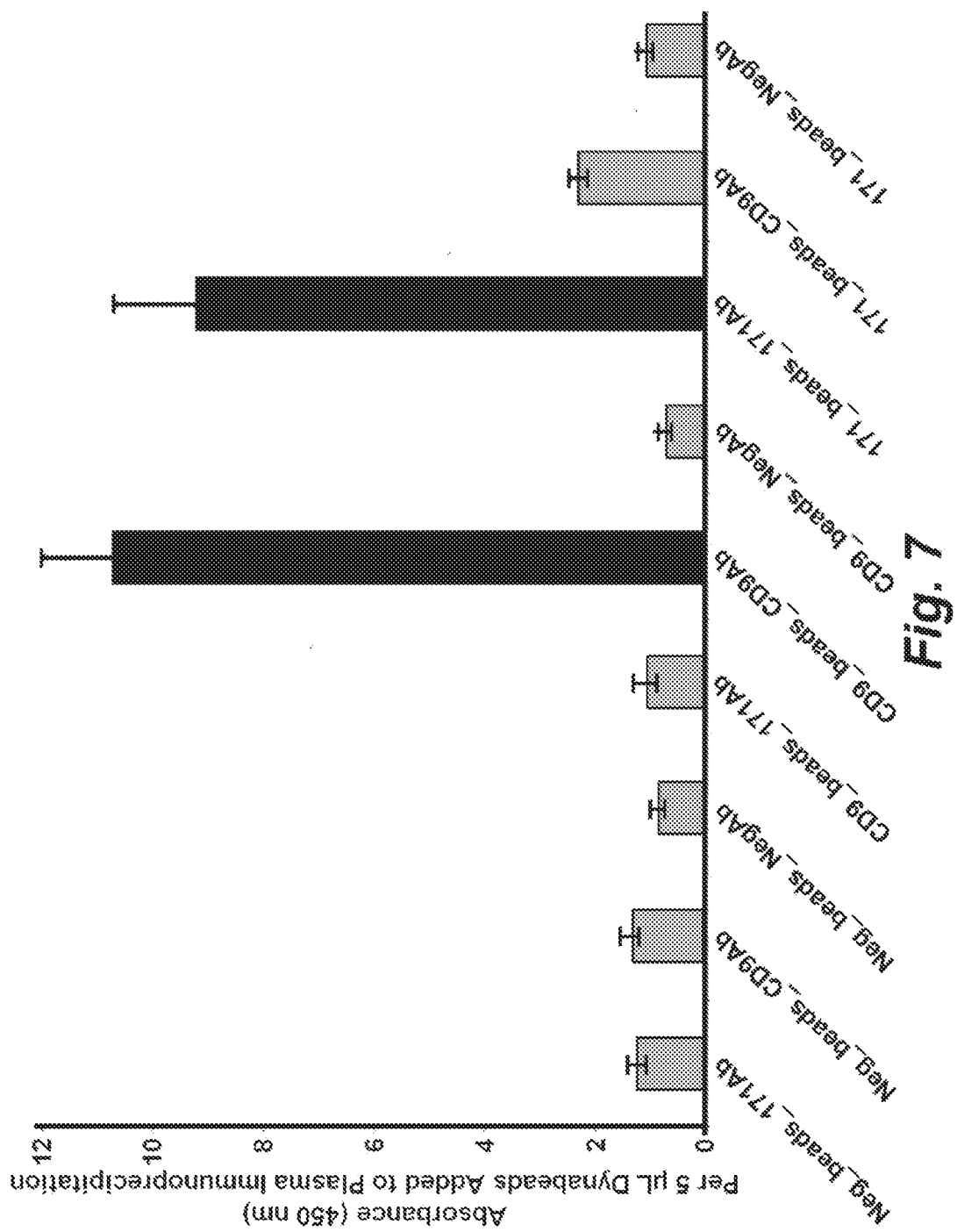
FIG. 7 shows ExoSense nsEV surface marker protein quantification assay colorimetric ELISA substrate absorbance data for various antibody-loaded magnetic microsphere/detection antibody combinations incubated with plasma. Results demonstrate that ExoSense enables quantification of both bulk and tissue-typed nsEV populations in biofluids. Respective Epoxy Dynabeads used were covalently coupled with anti-CD171 antibody (neuronal nsEV surface marker), anti-CD9 antibody (generic tetraspanin nsEV surface marker) or negative control antibody. Respective biotinylated detection antibodies (listed after the word 'Beads' in chart labels) were anti-CD171, anti-CD9 or negative isotype control. Absorbance values (cyan bar) for CD171 Dynabeads/CD9 detection illustrate that anti-CD171 antibody-loaded Dynabeads isolate nsEVs from plasma. Error bars denote standard deviations for two replicates.
Figure 8:
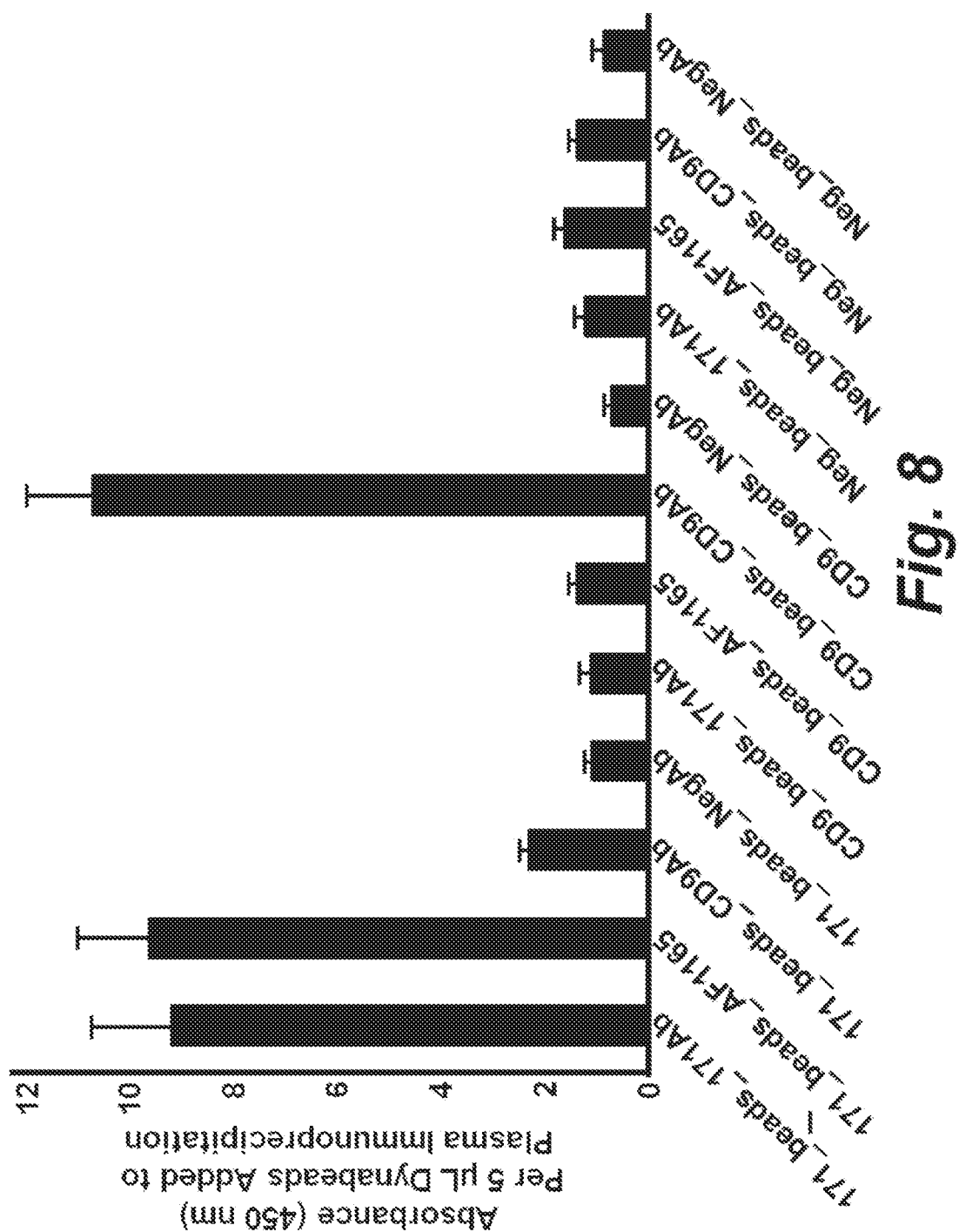
FIG. 8 shows ExoSense nsEV surface marker protein quantification assay colorimetric ELISA substrate absorbance data for various antibody-loaded magnetic microsphere/detection antibody combinations incubated with plasma. The figure illustrates the utility of ExoSense in quantifying levels of candidate disease-associated biomarkers, e.g., amyloid precursor protein (Feng et al. (2010) *Traffic*, 11(5): 675-687; Kanninen et al. (2015) *Biochim. Biophys Acta*. S09: 292-296; Caradec et al. (2014) *Clin. Biochem*. 47: 1286-1292), present on nsEV surfaces. Respective Epoxy Dynabeads used were covalently coupled with anti-CD171 antibody (neuronal nsEV surface marker), anti-CD9 antibody (generic tetraspanin nsEV surface marker) or negative control antibody. Respective biotinylated detection antibodies (listed after the word 'Beads' in chart labels) were anti-CD171, anti-amyloid precursor protein (AF1168 antibody), anti-CD9 or negative isotype control. Whereas the other three detection antibodies are monoclonal, AF1168 is a polyclonal antibody; the multiple epitope binding to amyloid precursor protein by this polyclonal antibody likely explains the high absorbance values observed. Error bars denote standard deviations for two replicates.

The flow cytometry histograms of FIGS. 5 and 6 illustrate the effectiveness of low pH washing in reducing or eliminating nonspecific binding of nsEVs to Dynabeads magnetic microsphere surfaces. The bar charts of FIGS. 7 and 8 show the effectiveness of the ExoSense assay in detecting generic nsEV surface protein markers, e.g., tetraspanins, nsEV tissue type surface markers, e.g., CD171 for neurons, and disease-associated biomarkers such as amyloid precursor protein.

Thus, in certain embodiments, a method of identifying and/or quantifying one or more biomarkers on the surface of nanoscale extracellular vesicles (nsEVs), where the method comprises:

i) incubating a biological sample comprising a population of nanoscale extracellular vesicles with a first antibody that binds said vesicles or a marker on said vesicles under conditions where said antibody binds said vesicles, where said first antibody is attached to a magnetic particle thereby providing a magnetic particle/vesicle immunocomplex;

ii) isolating said complex from said biological sample;

iii) washing said complex under high stringency wash conditions to remove non-nsEV entities in the biofluid;

iv) incubating said complex with a second antibody that binds to a marker of interest on the nsEV, where said second antibody is attached to a detectable label or is bound by a third antibody attached to a detectable label; and v) detecting the detectable label to indicate the presence or absence or quantity of said biomarker(s) on the surface of said nanoscale extracellular vesicles.

Figure 9:
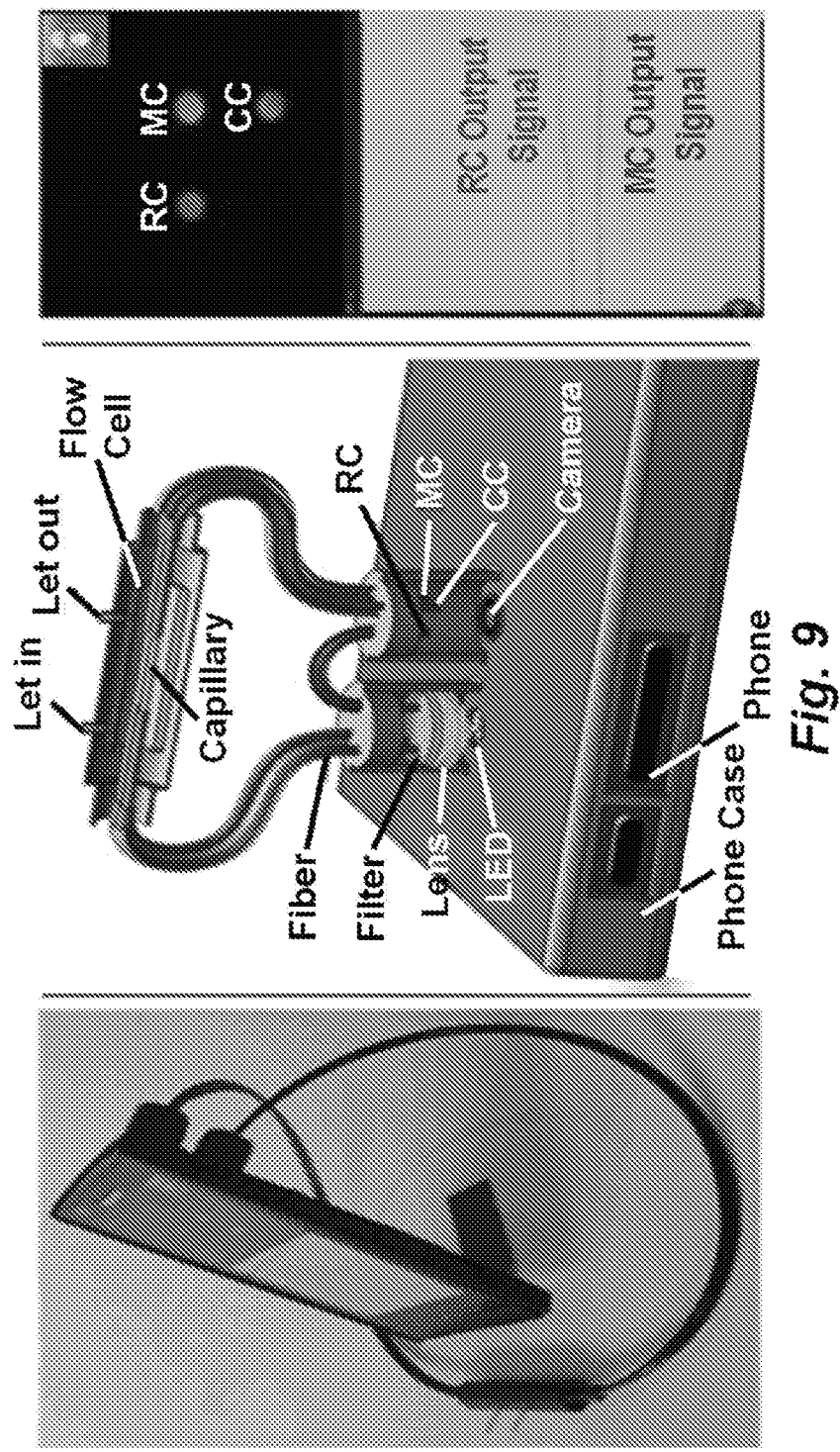
FIG. 9 illustrates a smartphone-based surface plasmon resonance device (Liu et al. (2105) *Sci. Rep*. 5: 12864) for point-of-need protein abundance measurement. Left panel: photograph of the SPR sensor installed on Android-based smartphone. Center panel: Schematic of smartphone with sensor attachment that enables SPR measurement. RC denotes SPR signal reference channel, MC denotes SPR signal measurement channel, CC denotes control channel used to enhance signal stability. Right panel: Data readout appearing on smartphone user interface. Upper panel shows intensity of LED signals in each of the above channels, lower panel shows SPR sensorgram that plots channel intensities as functions of time. Depicted MC output is undergoing sharp increase as analyte for detection enters flow cell.

Taken together, the data contained in the figures below show that the ExoSense method has immediate term utility in nsEV biomarker quantification research applications. As alluded to above, this method could also be adapted for compatibility with automated benchtop ELISA-reader instruments (see, e.g., www.bertholdds.com/crocodile-5-elisa-miniworkstation_10.html) or smartphone-type portable biomolecule quantification devices such as the cellphone-based surface plasmon resonance apparatus depicted in FIG. 9.

Detection.

The second antibody that binds to the marker of interest can be either directly labeled, or detected indirectly by addition, after washing off of excess second antibody, of a molar excess of a third, labeled antibody directed against the second antibody, e.g., directed against the IgG of the animal species of the second antibody. In the latter, indirect assay, labeled antisera against the second antibody can be added to the sample so as to produce the labeled antibody in situ.

The label used for either the second or third antibody can be any detectable functionality that does not interfere with the binding of the second antibody to the marker of interest on the nsEV. Examples of suitable labels are those numerous labels known for use in immunoassay, including moieties that may be detected directly, such as fluorochrome, chemiluminescent, and radioactive labels, as well as moieties, such as enzymes, that must be reacted or derivatized to be detected. Examples of such labels include, but are not limited to, the radioisotopes $^{32}P$, $^{14}C$, $^{125}I$, $^3H$, $^{131}I$, and the like, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, biotin/streptavidin, biotin/Streptavidin-.beta.-galactosidase with MUG, spin labels, bacteriophage labels, stable free radicals, and the like. As noted above, in certain embodiments, a multiwell ELISA format is utilized.

Conventional methods are available to bind these labels covalently to antibodies. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels (see, e.g., U.S. Pat. No. 3,940,475 (fluorimetry) and U.S. Pat. No. 3,645,090 (enzymes); Hunter et al. (1962) *Nature* 144: 945; David et al. (1974) *Biochemistry* 13: 1014-1021; Pain et al. (1981) *J. Immunol. Meth.* 40: 219-230; Nygren (1982) *J. Histochem. Cytochem.* 30: 407-412, and the like). In certain embodiments, labels herein are fluorescent to increase amplification and sensitivity, for example, biotin with streptavidin-β-galactosidase and MUG for amplifying the signal. In certain embodiments, a colorimetric label is used, e.g., where the detectable antibody is biotinylated and the detection means is avidin or streptavidin-peroxidase and 3,3',5,5'-tetramethyl benzidine.

The conjugation of such label, including the enzymes, to the antibody is a standard manipulative procedure for one of ordinary skill in immunoassay techniques (see, e.g., O'Sullivan et al. (1981) *Meth. Enzymol.* 73: 147-166).

Following the addition of the last labeled antibody, the amount of bound antibody is determined by removing excess unbound labeled antibody through washing and then measuring the amount of the attached label using a detection method appropriate to the label. For example, in the case of enzymes, the amount of color developed and measured will be a direct measurement of the amount of marker of interest present on the nsEV. Specifically, if HRP is the label, the color can be detected using the substrate 3,3',5,5'-tetramethyl benzidine at 450 nm absorbance.

Exosomes Triorthogonal-Linker Immuno-Photolytic Isolation Platform (Exo-TIP)

In certain embodiments improved methods of purifying (e.g., enriching) a population of nanoscale extracellular vesicles (nsEVs) such as exosomes or ectosomes are provided. In certain embodiments the method utilizes a triorthogonal linker comprising an antibody (e.g., an antibody that binds to an nsEV) that is attached by the linker to a magnetic bead where the linker comprises a photocleavable core disposed between the antibody and the magnetic bead and where the antibody is an antibody that binds a marker displayed on an nsEV (e.g., an exosome). In certain embodiments the linkers are designed to exploit click chemistry for coupling the antibody and the magnetic bead to the linker.

Click Chemistry is a term that was first coined by K. B. Sharpless (see, e.g.,. Kolb et al. (2001) *Angewandte Chemie Internat. Ed.* 40(11): 2004-2021; Evans (2007) *Australian J. Chem.* 60(6): 384-395) that describes pairs of functional groups (viz. alkyne and azide) that rapidly and selectively react ("click") with each other in mild, aqueous or organic conditions with nearly 100% completion (Kolb et al. (2001) supra.). The concept of Click chemistry has been transformed into convenient, versatile and reliable coupling procedures of two molecules that are of importance in biological and drug discovery research.

Typically, click reactions occur in one pot, are not disturbed by water, generate minimal and inoffensive byproducts, and are typically characterized by a high thermodynamic driving force that drives the reaction quickly and irreversibly to high yield of a single reaction product, with high reaction specificity (in some cases, with both regio- and stereo-specificity). These qualities make click reactions particularly suitable to the problem of isolating and targeting molecules in complex biological environments.

Carolyn Bertozzi more recently developed a copper-free click chemistry as an activated variant of an azide alkyne Huisgen cycloaddition based on the work by Fokin and Sharpless et al. (2002) Angew. Chem. Int. Ed., 41: 2596-2599. It has been modified to be bio-orthogonal by eliminating the use of cytotoxic copper catalyst, allowing reaction to proceed quickly and without cell toxicity (Baskin et al. (2007) Proc. Natl. Acad. Sci. USA, 104(43): 16793-16797) unlike the CuAAC, where cytotoxic Cu(I) is used as catalyst.

In various embodiments the Exo-Tip methods described herein utilize a linker that can undergo three independent reactions to capture nsEVs (e.g., exosomes) hence the linkers are described herein as triorthogonal linkers. In certain embodiments the linker comprise a first coupling group that can be an alkyne group (or an azide group) that can be clicked with an azide (or an alkyne, respectively) using Cu (I) as a catalyst to attach, e.g., a magnetic bead functionalized with the corresponding alkyne or azide. The linkers also have a second coupling group for attachment to a biomolecule (e.g., an antibody). In certain embodiments the second coupling group is an NHS-ester that readily reacts with free amines present in biomolecules (e.g., antibodies). In certain embodiments the second coupling group comprises a biotin which can react and bind an antibody functionalized with streptavidin. Thirdly, the linker has photocleavable core disposed between the first coupling group and the second coupling group that can that undergo cleavage and thereby separate the antibody (and bound moiety) from the magnetic bead when the linker is illuminated with light that stimulates the photocleavage. In certain embodiments the photocleavable core undergoes cargo release (cleavage) when exposed to UV light (1>360 nm) with the release of $CO_2$. In linker 1 illustrated herein (see, e.g., FIG. 16) in the rate limiting step photo-activated nitro group abstract benzylic proton from the o-nitrobenzyl moiety present in the linker (see, e.g., Holmes (2007) J. Org. Chem. 62: 2370-2380 and Piggott et al. (2005) Tetra. Letts. 46: 8241-8244).

Figure 13:
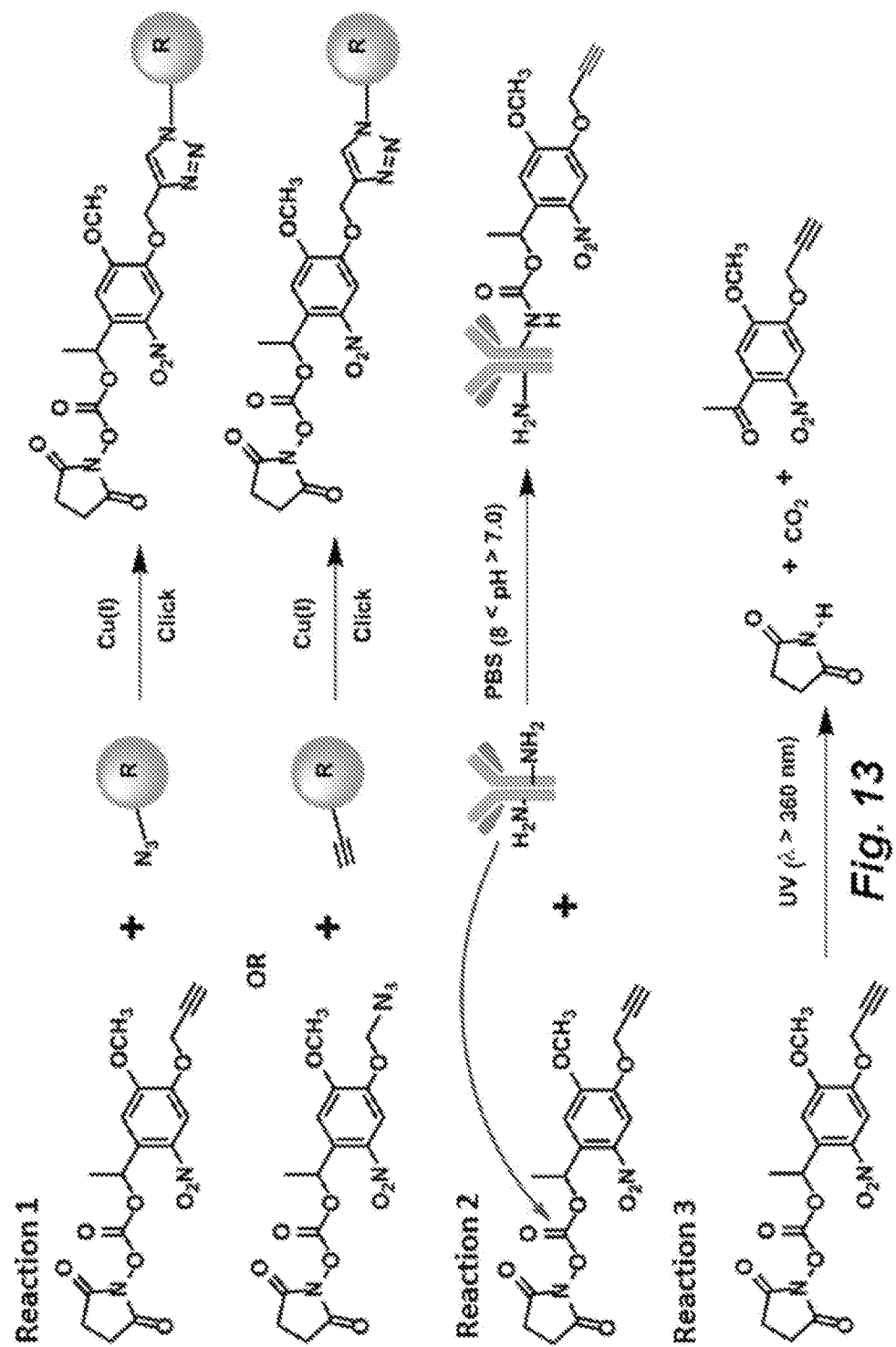
FIG. 13 illustrates three independent reactions that the triorthogonal linkers described herein can undergo.

The three independent reactions are illustrated in FIG. 13.

In certain embodiments the triorthogonal linkers described herein can be used to purify (enrich) a population of nanoscale extracellular vesicles (e.g., exosomes). In certain embodiments the methods involve:

i) providing a triorthogonal linker comprising an antibody that is attached by the linker to a magnetic bead where the linker comprises a photocleavable core disposed between the antibody and the magnetic bead and where the antibody is an antibody that binds a marker displayed on an nsEV (e.g., an exosome);

ii) contacting a biological sample comprising nsEVs with the triorthogonal linker under conditions where the antibody binds to an nsEV in the sample to form a complex comprising a magnetic bead attached by the linker to an nsEV;

iii) utilizing a magnet/magnetic field to isolate the complex from other components in said sample;

iv) exposing the complex to light (e.g., to UV light) to cleave the photocleavable core and separate the magnetic bead from the antibody-bound nsEV; and v) utilizing a magnet/magnetic field to separate the magnetic bead(s) from the antibody-bound nsEV(s) to provide a substantially purified population of antibody-bound nsEvs.

Figure 14:
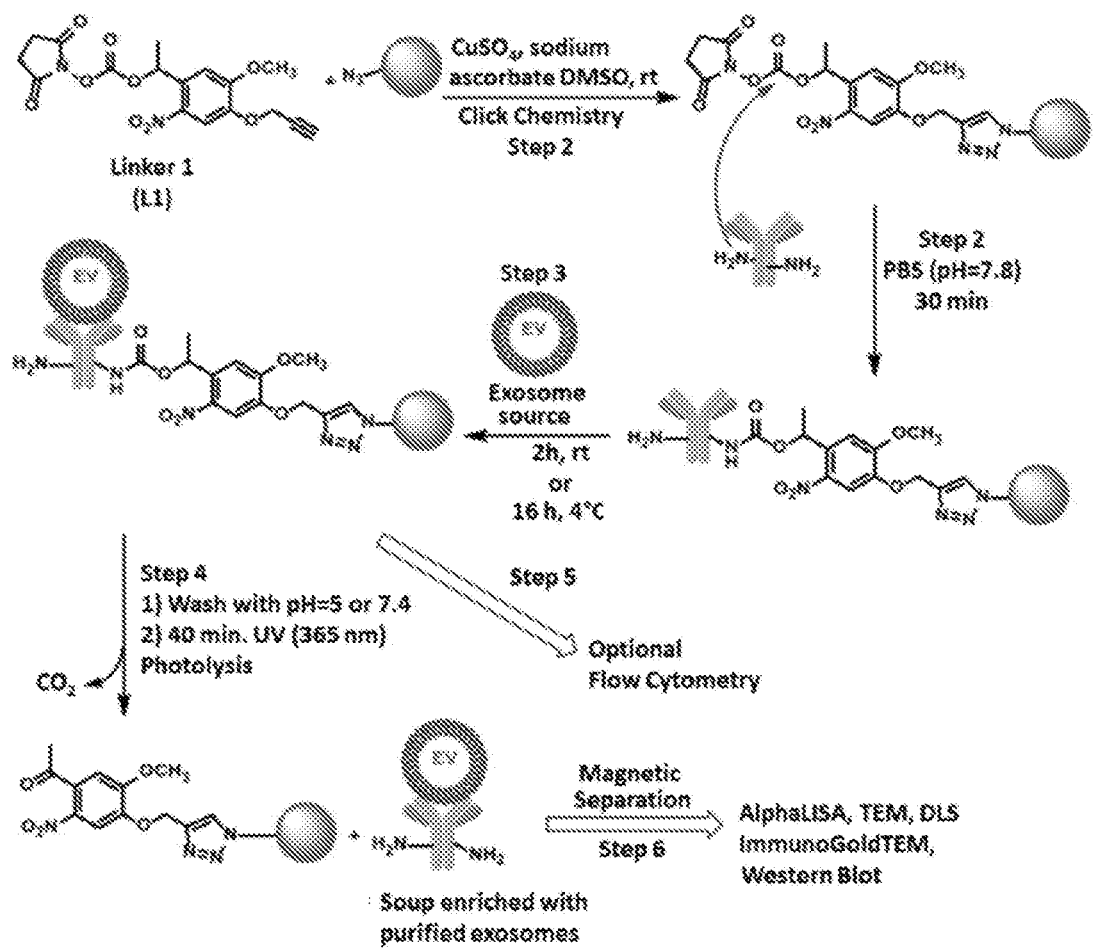
FIG. 14 schematically illustrates Scheme 1 showing one embodiment of an Exo-TIP purification of neuronal exosomes. Although in the illustrated scheme azide is shown on the beads and alkyne on the linker, the Cu(I)-catalyzed azide-alkyne cycloaddition (CuAAC) or a Cu(I)-free azide-DBCO click chemistry reaction can be attained even if the alkyne is switched from the linker to the beads and the azide from the beads to the linker. It is also noted that the activated ester can be replaced with an avidin or biotin to link an antibody using an avidin/biotin reaction.
Figure 15:
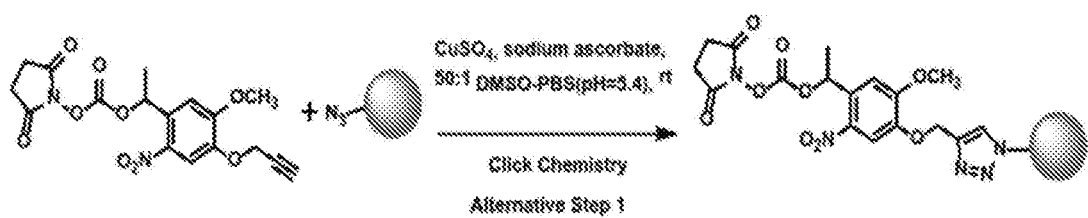
FIG. 15 illustrates Scheme 2 showing an alternative scheme for azide-alkyne click using copper in the first step. Here sodium ascorbate stock was made in PBS (pH=5.4) and added to the reaction mixture at 1:50 ratio of DMSO.

One illustrative but non-limiting embodiments of this method is shown in FIG. 14. The method shown FIG. 14 is illustrated with linker 1 (L1) (isee, e.g., FIG. 16). However, it will be recognized that in certain embodiments, the alkyne in linker L1 can be replaced with an azide (see, e.g., linker 1A, FIG. 16) and the azide on the antibody can be replaced with an alkyne and the method performed in the same manner.

Figure 16:
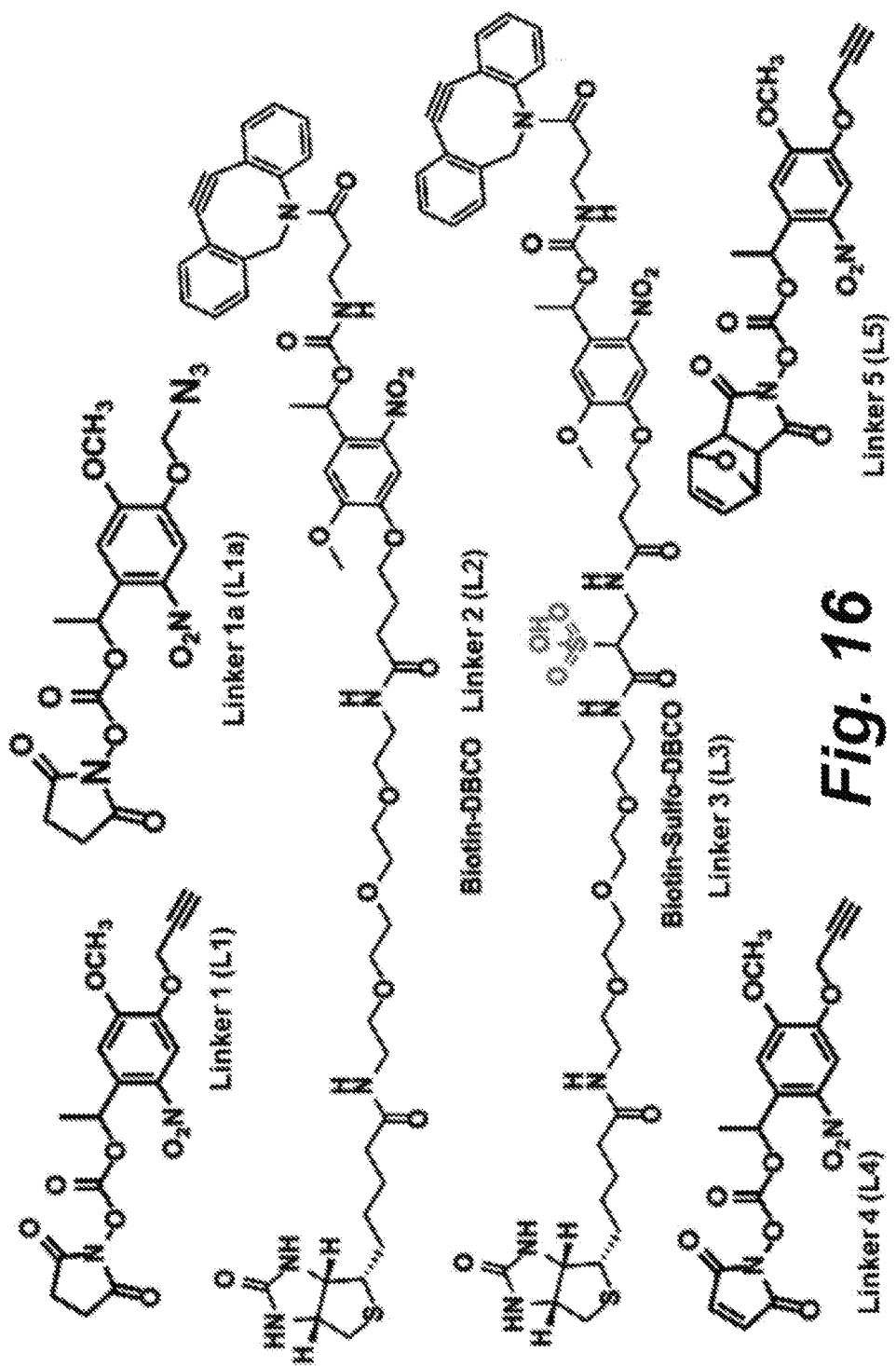
FIG. 16 illustrates various triorthogonal linkers that can be used in the Exo-TIP methods of exosome isolation/purification described herein.

In certain embodiments the NHS-ester is replaced with a biotin and the antibody, functionalized with streptavidin (or other avidin) can be coupled to the linker using a biotin/avidin interaction. Illustrative but non-limiting biotin linkers are also shown in FIG. 16.

In certain embodiments the linker is a maleimide linker. Illustrative, but non-limiting maleimide linkers include, but are not limited to linkers L4 and L6 shown in FIG. 16.

In various embodiments these "Exo-TIP" purification methods can be used to isolate and enrich nsEVs (e.g., exosomes) in the ExoQuant and ExoSense methods described above.

The various Exo-TIP purification (enrichment) methods described herein are illustrative and not limiting. Using the teachings provided herein other enrichment methods will be available to one of skill in the art.

Triorthogonal Linkers for use in Exo-TIP.

In various embodiments triorthogonal linkers suitable for use in the methods described herein comprise a linker comprising an antibody that is attached by the linker to a magnetic bead where the linker comprises a photocleavable core disposed between the antibody and the magnetic bead. In certain embodiments the antibody is an antibody that binds a marker displayed on an nsEV (e.g., an exosome).

In certain embodiments of the triorthogonal linker the linker comprises:

a first coupling group that (before reaction with a functionalized magnetic particle), comprises an alkyne or an azide;

a second coupling group that (before reaction with a biomolecule), comprises a biotin or an NHS-ester (N-hydroxysuccinimide ester) capable of reacting with a free amine in a biomolecule; and a photocleavable core disposed between the first group and said second group. In certain embodiments the first coupling group comprises an alkyne. In certain embodiments the first coupling group comprises an azide. In certain embodiments the second group comprises an NHS-ester. In certain embodiments the photocleavable core comprises a moiety selected from the group consisting of nitrobenzyl, nitrophenethyl compounds, and their dimethoxy derivatives (e.g., nitroveratryl) (see, e.g., Klan et al. (2013) Chem. Rev., 113: 119-191).

In certain embodiments the linker comprises the structure of Formula I:

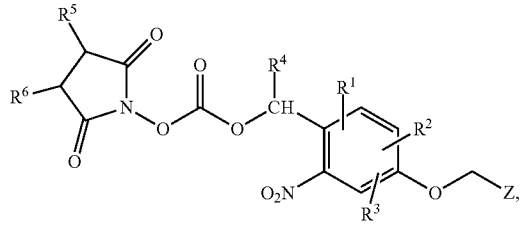

where $R^1$ is selected from the group consisting of H, —$OCH_3$, $CH_3$, a C1 to C5 alkyl, and a halogen; $R^2$ is selected from the group consisting of H, —$OCH_3$, $CH_3$, and a halogen; $R^3$ is selected from the group consisting of H, $CH_3$, a halogen, and a C1 to C5 alkyl; $R^4$ is selected from the group consisting of H, $CH_3$, a halogen, a phenyl, and a C1 to C5 alkyl; $R^5$ is H or sulfo; $R^6$ is H or sulfo; and Z is alkyne or azide. In certain embodiments, $R^4$ is selected from the group consisting of H, $CH_3$, a halogen, and a C1 to C5 alkyl. In certain embodiments $R^1$ is $OCH^3$, and/or R2 is $OCH_3$, and/or $R^4$ is $CH_3$ or Ph.

In certain embodiments the linker comprises the structure of Formula II:

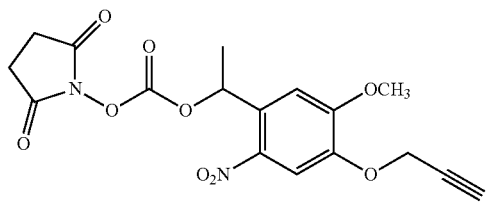

In certain embodiments the linker comprises the structure of Formula III:

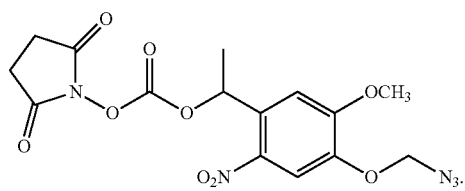

In certain embodiments the second coupling group of the linker comprises a biotin. In certain embodiments the linker comprises the structure of Formula IV:

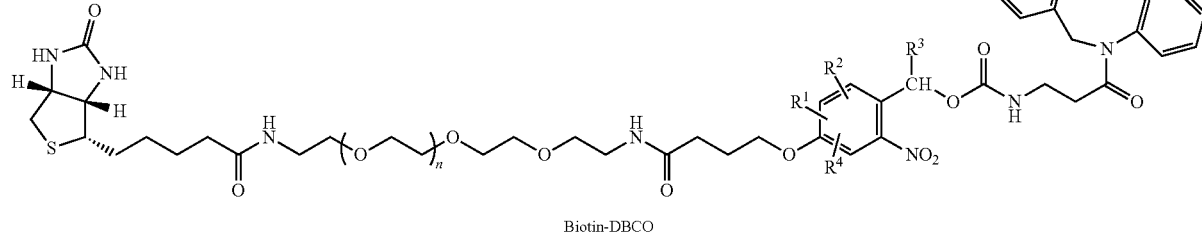

Biotin-DBCO or Formula V:

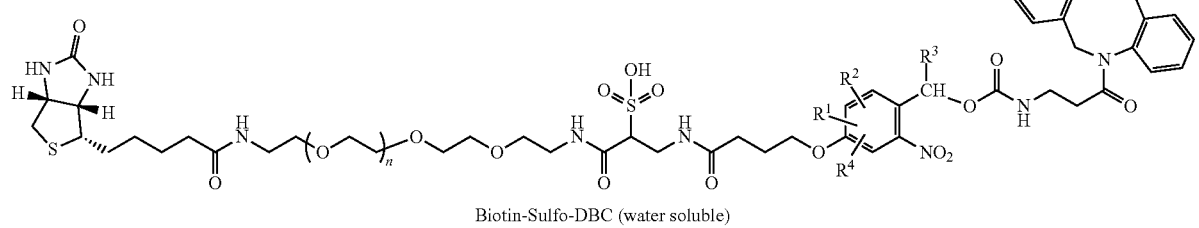

Biotin-Sulfo-DBC (water soluble)

where n is 1, 2, 3, 4, 5, 6, 7, 8, 9, or 10; $R^1$ is selected from the group consisting of H, —OCH$_3$, CH$_3$, a C1 to C5 alkyl, and a halogen; $R^2$ is selected from the group consisting of H, —OCH$_3$, CH$_3$, and a halogen; $R^3$ is selected from the group consisting of H, CH$_3$, a halogen, and a C1 to C5 alkyl; and $R^4$ is selected from the group consisting of H, CH$_3$, a halogen, and a C1 to C5 alkyl.

In certain embodiments the linker is bound via reaction of the first coupling group to a functionalized magnetic particle (e.g., a linker bearing an alkyne is reacted with a magnetic bead functionalized with an azide, a linker bearing an azide is reacted with a magnetic bead functionalized with an alkyne, etc.).

In certain embodiments the linker is bound via reaction of said second coupling group to an antibody. In certain embodiments the linker is bound to the antibody via reaction of said NHS-ester to an amine on the antibody. In certain embodiments the linker is bound to the antibody via reaction of said biotin to a streptavidin attached to the antibody.

In certain embodiments the antibody attached to the linker is an antibody that binds an nsEV (e.g., an exosome) specific antigen. In certain embodiments the antibody binds an exosome-specific antigen selected from the group consisting of CD63, CD9, CD81, hsp70, CD37, CD53, CD82, CD13, CD11, CD86, ICAM-1, Rab5, Annexin V, LAMP1, CD-31, HLA-G, and Rab5bT.

Methods of making triorthogonal linkers are described in Example 3 herein. Using the teachings provided herein, numerous other synthetic protocols and triorthogonal linkers will be available to one of skill in the art.

Example 1

Blood Test for Alzheimer's Disease (AD) Diagnosis and Treatment Monitoring

The 3D-detection ExoQuant method was used to assess the Aβ peptide levels on the surface of brain-specific exosomes.

Step 1. Frozen plasma samples from AD patients and normal (NL) control subjects were used for the experiment. Plasma samples were quickly defrosted at 37° C. and diluted 5 times with blocking buffer (0.5% BSA, 0.5% gelatin, 1 mg/ml dextran 500 in PBS, pH 7.4), supplemented with the Halt protease and phosphatase inhibitor cocktail (Thermo-Scientific). Neuronal Cell Adhesion Molecule (NCAM) was used as a brain-specific marker. All antibodies were either biotinylated or conjugated to AlphaLISA acceptor beads (Perkin Elmer) according to the manufacturer's protocol. Anti-NCAM antibodies (clone HCD56, BioLegend) conjugated to acceptor beads (5 mg/ml) were diluted 10 times with preblocking buffer (5% BSA, 0.5% gelatin in PBS, pH7.4) and incubated for 30 minutes at room temperature (RT). Pre-blocked beads (4 µl; 0.5 mg/ml) were added to the AD and NL plasma samples (600 µl of 1:5 diluted plasma), and incubated overnight at 4° C. with slow rotation. The acceptor beads with immobilized material were pulled out from the solution by centrifugation at 16,000×g for 15 minutes, washed 3 times with blocking buffer and diluted in 65 µl of blocking buffer to achieve a concentration of acceptor beads of 30 µg/ml.

Step 2. The acceptor beads with immobilized material from step 1 were added into a non-binding 384-well assay plate (5 µl per well; Corning), mixed with 5 µl either empty acceptor beads (120 µg/ml in blocking buffer) or 5 µl of acceptor beads conjugated to one of the anti-Aβ antibodies (120 µg/ml; 7N22, Invitrogen; 12F4 BioLegend; or 82E1, Demeditec Diag. GmbH) and incubated for 90 minutes at RT.

Step 3. Biotinylated anti-CD9 antibodies (Cosmo Bio Co., LTD) or biotinylated isotype control antibodies (BioLegend) (5 µl per well; 4 nM) were added to each well and incubated for 40 minutes at RT.

Step 4. Streptavidin-conjugated donor beads (5 µl per well; 160 µg/ml) were added to the reactions and incubated for 30 minutes at RT.

Figure 3:
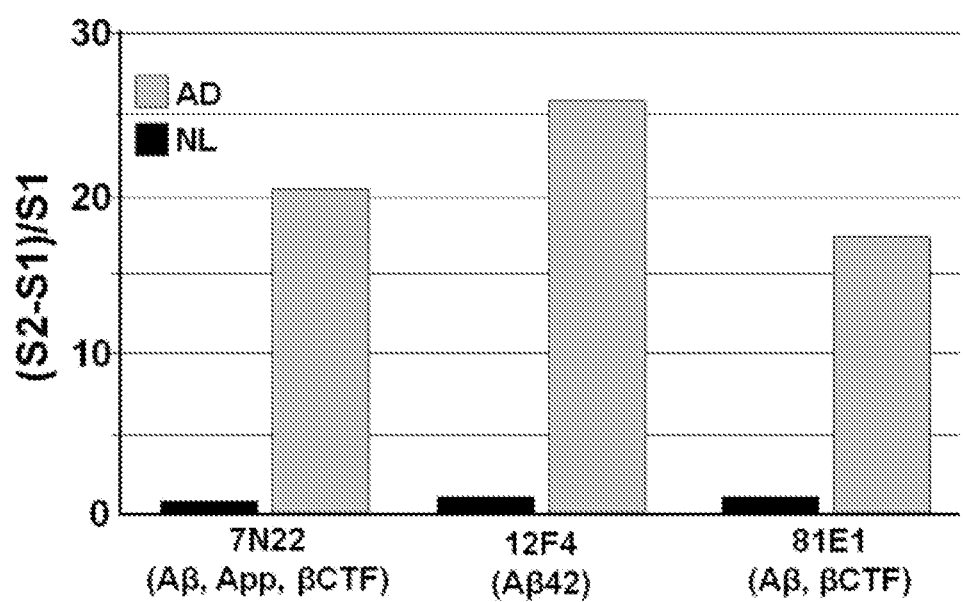
FIG. 3 shows the Aβ signal on brain-derived exosomes in plasma.

Step 5. AlphaLISA signal from each well was detected by Perkin Elmer's Enspire plate reader (total time: 400 ms; excitation time: 100 ms; distance: 0.2 mm). The relative intensity of Aβ signal on the surface of NCAM/CD9-positive exosomes was calculated by the formula: (S2-S1)/S1, where S1 is the intensity of AlphaLISA signal, coming from the NCAM/CD9 reaction, and S2 is the signal intensity from the NCAM/Aβ/CD9 reaction for the same plasma sample. We demonstrated elevated levels of Aβ on the surface of NCAM/CD9-positive exosomes from AD patient plasma compared to NL subject plasma using three different Aβ-specific antibodies (FIG. 3). Our method may be utilized for non-invasive early diagnosis of AD, monitoring of drug treatment effects, and identification of markers and targets for new therapeutic approaches in AD.

Example 2

Nanoscale Extracellular Vesicle (nsEV) Analysis in Alzheimer's Disease Diagnosis & Therapy Introduction Blood-borne neuron-derived (neuronal) nanoscale extracellular vesicles (nsEVs) have shown to have substantial potential as "Windows Into The Brain" that enlighten central nervous system (CNS) disorder-associated changes in brain biochemistry and intercellular communication (Fiandaca et al. (2015). *Alzheimers Dement.* 11: 600-607; Goetzl et al. (2015) *Neurology*, 85(1): 40-47; Goetzl et al. (2015) *Ann. Clin. Transl. Neurol.* 2: 769-773; Kapogiannis et al. (2015) *FASEB J.* 29(2): 589-596; Shi et al. (2014) *Acta Neuropathol.* 128: 639-650; Cheng et al. (2015) *Mol. Psychiatry*, 20: 1188-1196; Lugli et al. (2015) *PLoS One*, 10(10): e0139233). Neuronal nsEV analysis can be leveraged in the context of identifying novel approaches for treating AD. These opportunities may be realized by further developing existing protocols for nsEV isolation to achieve high-purity enrichment of bloodborne neuronal nsEVs that enables "omics" profiling of nsEV protein and RNA constituents; such omics profiles could increase our understanding of changes in brain biochemistry and intercellular signaling that both underlie and reflect AD pathology and provide a three-dimensional nsEV (3D) profile. It is believed this knowledge will have an important clinical impact by facilitating both identification of novel AD drug targets and development of new molecules and/or modalities for AD prophylaxis and treatment.

Defining Features of nsEVs

There are no universally accepted criteria for classifying nsEVs. This lack of standard taxonomy creates ambiguity in interpreting and communicating the results of nsEV-related experiments. Our simple classification system defines nsEVs as cell-derived vesicles with sub-micron diameters and groups them into two categories: exosomes and ectosomes.

Exosomes are manufactured within multivesicular bodies (MVBs), cytoplasmic vesicles that have diameters in the 250-1,000-nm range (Nagashima et al. (2014) *J. Gen. Virol.*

95: 2166-2175; Von Bartheld and Altick (2011) *Prog. Neurobiol.* 93: 313-340), and are formed by inward budding of late endosomes (Urbanelli et al. (2013) *Genes* (Basel). 4: 152-170). Exosome diameters range from 50-200 nm (Cocucci and Meldolesi (2015) *Trends Cell Biol.* 25: 364-372) and their surfaces are enriched in tetraspanin marker proteins CD9, CD63, and CD81, as well as heat shock proteins such as Hsp70 (Multhoff and Hightower (2011) *Cell Stress Chaperones,* 16: 251-255; Ghosh et al. (2014) *PLoS One,* 9(10): e110443). Exosomes carry high interior levels of Tsg101 and Alix, two proteins comprising the Endosomal Sorting Complexes Required for Transport (ESCRT) machinery involved in intracellular vesicle formation processes (Cocucci and Meldolesi (2015) *Trends Cell Biol.* 25: 364-372). Conversely, ectosomes are vesicles with diameters ranging from 100 nm to 1 micron that bud off from cell plasma membranes.

Others have categorized ectosomes into a number of somewhat ambiguous subclasses: shedding vesicles, microvesicles, exosome-like vesicles, nanoparticles, microparticles, and oncosomes (Cocucci and Meldolesi (2015) *Trends Cell Biol.* 25: 364-372). Although it had been believed that tetraspanin proteins were exosome-specific surface markers more recent analyses have revealed that tetraspanins appear on the surfaces of both exosomes and ectosomes; there are currently no surface marker proteins that distinguish between these two classes of nsEVs (Andreu and Yáñez-Mó (2014) *Front. Immunol.* 5: 442; Crescitelli et al. (2013) *J. Extracell. Vesicles,* 12;2. doi: 10.3402/jev.v2i0.20677; Hurley (2015) *EMBO J.* 34: 2398-2407).

nsEVs with diameters between 100 nm and 200 nm can be either exosomes or ectosomes; the vesicle category into which a given nsEV would be classified would be determined by whether the nsEV is formed within a MVB or budded off from the cell plasma membrane.

nsEVs encapsulate nucleic acids, primarily micro RNAs (miRNAs) and messenger RNAs (mRNAs). nsEVs also feature integral membrane proteins, proteins covalently bound to nsEV membranes, proteins noncovalently associated with nsEV membranes, and proteins that occupy nsEV interior volumes. nsEVs' principal function is transferring signals from sender to recipient cells. nsEVs originating from sender cells can fuse with membranes of and release their contents into the cytoplasm of recipient cells (van den Boorn et al. (2011) *Nat. Biotechnol.* 29: 325-326) or have their contents trafficked among different intracellular compartments after recipient cell phagocytosis (Feng et al. (2010) *Traffic,* 11(5): 675-687). nsEV-delivered signals are carried by membrane proteins, interior proteins, miRNAs that suppress transcription of targeted recipient cell genes, or mRNAs that elevate recipient cell translation of the mRNA-encoded proteins.

Given the desire to leverage bloodborne nsEV analysis in enlightening AD-associated changes and brain biochemistry and intercellular signaling processes, we note here that neuronal nsEVs have been observed to migrate from the CNS into the bloodstream in animal experiments (Shi et al. (2014) *Acta Neuropathol.* 128: 639-650). The existence of a similar neuronal nsEV migratory phenomenon in humans is supported by the results of blood sample AD diagnostic assays (Fiandaca et al. (2015). *Alzheimers Dement.* 11: 600-607; Goetzl et al. (2015) *Neurology,* 85(1): 40-47; Goetzl et al. (2015) *Ann. Clin. Transl. Neurol.* 2: 769-773; Kapogiannis et al. (2015) *FASEB J.* 29(2): 589-596; Shi et al. (2014) *Acta Neuropathol.* 128: 639-650).

nsEV Analysis

The predictive ability of bloodborne neuronal nsEV analysis illustrated by the biomarker validation studies of Goetzl and co-workers, which accurately forecasted AD onset up to ten years prior to clinical diagnosis (Fiandaca et al. (2015). *Alzheimers Dement.* 11: 600-607; Goetzl et al. (2015) *Neurology,* 85(1): 40-47; Goetzl et al. (2015) *Ann. Clin. Transl. Neurol.* 2: 769-773; Kapogiannis et al. (2015) *FASEB J.* 29(2): 589-596), has generated considerable interest in the AD research community. Here we define the state of the art in bloodborne nsEV analysis methods by describing the methods utilized in Goetzl's AD biomarker quantification process. In addition we discuss the potential of 3D nsEV analysis to further build on Goetzl's methods and fully realize the potential impact of nsEV characterization in AD clinical diagnostic platform and drug development.

The first step in Goetzl's nsEV AD biomarker quantification process was chemical precipitation (CP) to isolate nsEVs from plasma. After nsEV precipitation, neuronal nsEVs were enriched from the bulk nsEV population using streptavidin-coated agarose beads loaded with biotinylated anti-neuronal marker protein (CD171) Abs. Finally, nsEVs were exposed to lysing conditions and biomarker proteins in nsEV lysates were quantified by ELISA. The Cartesian coordinate system of FIG. 10 serves as a useful aid in defining the concept of 3D nsEV analysis; below we provide such a definition by further discussing the steps that comprise the Goetzl biomarker quantification process in the context of this schematic.

Figure 10:
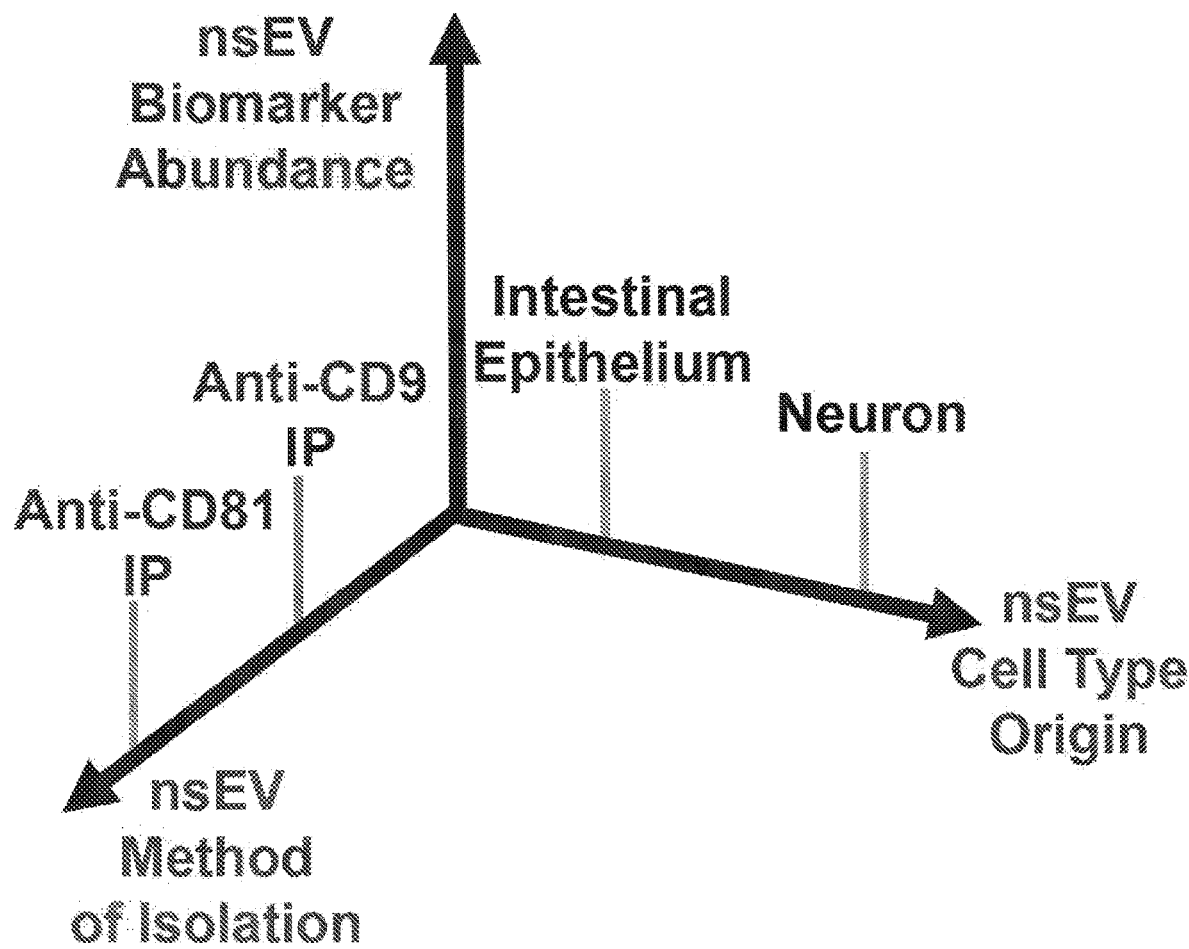
FIG. 10. Three-dimensional nsEV phenotyping Cartesian coordinate system. X-Axis defines method of nsEV isolation dimension; anti-CD9 IP and anti-CD81 IP are denoted as two representative X-axis points. Y-Axis defines nsEV cell type origin dimension; intestinal epithelium and neuron are denoted as two representative Y-axis points. Z-Axis defines biomarker abundance dimension. Z-Axis units will vary depending upon the method used to quantify biomarker abundance(s); no representative Z-axis points are denoted in this figure.

As illustrated in FIG. 10, each nsEV analysis dimension axis features multiple points that can define a given nsEV characterization experiment. The choice of nsEV enrichment method, i.e., CP, size exclusion chromatography (SEC), ultracentrifugation (UC), or immunoprecipitation (IP) (Kanninen et al. (2015) *Biochim. Biophys Acta.* S09: 292-296; Caradec et al. (2014) *Clin. Biochem.* 47: 1286-1292; Lobb et al. (2015) *J. Extracell. Vesicles.* 4: 27031; Théry et al. (2006) *Curr. Protoc. Cell Biol.* Chapter 3: Unit 3.22), determines the method of isolation axis coordinate. In the context of Goetzl's work, CP marks the point occupied on the method of isolation axis coordinate. The specificity of the Ab used in IP of nsEVs originating from a cell type of interest, e.g., neurons, defines the cell-type axis coordinate. In Goetzl's experiments, the use of agarose beads loaded with anti-CD171 Abs for nsEV IP defines the cell-type axis coordinate as neuronal.

The third nsEV analysis dimension, biomarker abundance, differs from the other two dimensions in that biomarker abundance, and thus position on the biomarker abundance axis, is dictated by nsEV composition. The researcher chooses which biomarker(s) to quantify and thus defines biomarker abundance axis label(s). As Goetzl and colleagues quantified a set of ten proteins posited to be associated with onset and/or progression of AD. Regardless of whether the researcher quantifies just a few biomarkers, as in Goetzl's validation studies, or quantifies hundreds of candidate biomarkers in omics analyses, the number of nsEV phenotype coordinate systems will match the number of quantified biomarker species.

Translational Potential of nsEV Analyses in AD Diagnosis & Drug Development

The underexplored opportunity in the area of leveraging bloodborne neuronal nsEV omics profiling in AD biomarker discovery for drug molecule and therapeutic modality development is well-framed by discussing existing neuronal nsEV AD biomarker validation and discovery-related literature; the latter is particularly relevant to utilizing neuronal nsEV analysis in identification of novel drug targets and establishment of new treatment paradigms. In this discussion we define nsEV biomarkers as protein or nucleic acid nsEV constituents with abundances that differ in diseased relative to normal subjects. This definition encompasses nsEV-associated molecules with relative abundances that change prior to clinical manifestation of disease symptoms and thus can be predictive of disease onset as well as molecules with abundances that change as functions of disease progression or reversion due to positive treatment responses.

We begin our discussion of the literature relevant to nsEV AD biomarker validation by revisiting the works of Goetzl (Fiandaca et al. (2015). *Alzheimers Dement.* 11: 600-607; Goetzl et al. (2015) *Neurology*, 85(1): 40-47; Goetzl et al. (2015) *Ann. Clin. Transl. Neurol.* 2: 769-773; Kapogiannis et al. (2015) *FASEB J.* 29(2): 589-596) and noting that in addition to accurately forecasting AD onset, Goetzl found that an impressively wide range of proteins, i.e., transcription factors (Goetzl et al. (2015) *Ann. Clin. Transl. Neurol.* 2: 769-773), molecular chaperones (Goetzl et al. (2015) *Neurology*, 85(1): 40-47), beta-amyloid 1-42 (Aβ42) (Fiandaca et al. (2015). *Alzheimers Dement.* 11: 600-607), phosphorylated Tau (Id.), and phosphorylated insulin receptor substrate-1 (Kapogiannis et al. (2015) *FASEB J.* 29(2): 589-596), can serve as predictive AD biomarkers. Also under the umbrella of noteworthy achievements in validating neuronal nsEV constituents as CNS disorder biomarkers, levels of alpha-Synuclein (α-Syn) carried by bloodborne neuronal nsEVs have been observed to correlate with PD severity (Shi et al. (2014) *Acta Neuropathol.* 128: 639-650). Taken together, the above body of results suggests that bloodborne neuronal nsEV analysis could serve as the basis for clinical diagnostic assays that can predict the onset of and/or monitor the progression or reversion of CNS disorders.

The bloodborne neuronal nsEV isolation and analysis methods used in Goetzl's works require more specimen processing steps than are typically associated with clinical diagnostic assays. It is however, likely that adapting these methods or using other nsEV biomarker measurement techniques could lead to clinically applicable AD diagnostic assays.

Although considerable progress has been made in validating neuronal nsEV biomarkers for AD diagnostic applications (Fiandaca et al. (2015). *Alzheimers Dement.* 11: 600-607; Goetzl et al. (2015) *Neurology*, 85(1): 40-47; Goetzl et al. (2015) *Ann. Clin. Transl. Neurol.* 2: 769-773; Kapogiannis et al. (2015) *FASEB J.* 29(2): 589-596), much of the script in the arena of discovering neuronal nsEV AD biomarkers for drug target identification and therapeutic development remains unwritten. Such discovery may be enabled by omics methods that characterize neuronal nsEV populations enriched from blood plasma or blood serum. Proteomic approaches, such as tandem mass spectrometry (MS/MS) (Tomlinson et al. (2015) *Ann. Clin. Transl. Neurol.* 2: 353-361), generate abundance-ranked lists of nsEV-associated proteins present in amounts exceeding proteomic analysis method detection limits, which are generally single-digit picomolar. Comparing rank order protein lists for normal and AD subject nsEVs enables identification of new nsEV protein AD biomarkers. Similarly, next-generation RNA sequencing techniques, such as Illumina (Cheng et al. (2015) *Mol. Psychiatry*, 20: 1188-1196), generate global, rank order abundance profiles for bloodborne neuronal nsEV miRNAs and/or mRNAs. Using these profiles to compare levels of RNAs across AD and normal neuronal nsEVs respectively could help elucidate novel AD biomarkers.

With respect to the avenues by which omics-based nsEV biomarker discovery can reveal new drug targets and therapeutic approaches for treating AD, we begin by noting that the proteins and nucleic acids contained within nsEVs, as well as proteins both covalently and noncovalently associated with nsEV membranes, reflect the contents of the cytoplasm and/or plasma membrane of nsEV parent cells (Cocucci and Meldolesi (2015) *Trends Cell Biol.* 25: 364-372). As such, AD-associated changes in neuronal molecular composition can be reflected by differences between AD neuronal nsEV composition and the composition of normal subject nsEVs. By extension, correlations between neuronal nsEV composition and the propensity for developing and/or clinically measured severity of AD can inform AD-associated changes in neuronal biochemistry.

These changes in neuronal biochemistry could either play a causative role in AD or be reflective of disease progression. Regardless of which of these cases applies, the knowledge of such AD-associated changes in cellular composition can heighten one's insight regarding how the intracellular molecular milieu is altered either before or after the onset of AD; such augmented insight may add to one's understanding of the mechanisms underlying AD and thus could enlighten novel drug targets or approaches to AD therapy.

An illustration of how the above-noted process of using knowledge, obtained via molecular-level analysis of blood-borne neuronal nsEVs, regarding AD-associated changes in neuronal molecular composition could be applied in developing new strategies for treating AD can be derived from Goetzl's studies of levels of ubiquitinylated proteins carried within bloodborne neuronal nsEVs (Goetzl et al. (2015) *Neurology*, 85(1): 40-47). Goetzl found that ubiquitinylated proteins, where ubiquitin often serves to mark proteins for degradation in lysosomes, were significantly more abundant in bloodborne neuronal nsEVs isolated from AD subjects than in nsEVs isolated from normal persons. This observation implies that ubiquitinylated proteins might be present at elevated levels within the CNS neurons of AD subjects and also suggests that dysfunction of neuronal lysosomes and/or lysosomal trafficking processes could contribute to AD pathology. This posited causative role of dysregulated protein degradation in AD brings modulation of lysosome function and ubiquitinylated protein trafficking within the CNS to light as potential strategies for treating AD.

Neuronal nsEV analysis can also illuminate the bases of AD pathology by virtue of nsEVs' roles as facilitators of intercellular communication. Changes in neuronal nsEV signaling molecule levels, particularly RNAs that correspond to AD, can reveal alterations in cell-to-cell communication that are caused by or contribute to AD onset and/or progression. As such, identifying molecules within or on nsEV surfaces with abundances that change in AD subjects facilitates formulation of hypotheses regarding connections between altered intercellular signaling and AD pathology. Knowledge of these differences can help elucidate the mechanisms underlying AD pathology onset and progression; such insights can enable identification of novel drug targets and foster the development of novel AD treatment regimens.

The work of Liu and colleagues (Liu et al. (2014) *Mol. Med. Rep.* 10: 2395-2400) provides context regarding how knowledge of AD-associated changes in nsEV signaling molecule levels can enlighten new treatment strategies. Liu observed that levels of miR-193b, which is believed to reduce amyloid precursor protein (APP) expression, are decreased in bloodborne nsEVs isolated from AD subjects relative to normal persons. This finding motivates consideration of drug carrier-encapsulated, CNS-targeted (Zhang et al. (2013) *J. Control Release,* 172(3): 962-974) miR-193b as a candidate agent for AD therapy.

The feasibility of proteomic and transcriptomic analyses in bloodborne nsEV CNS-disorder biomarker discovery has been established. Tomlinson and colleagues (van den Boorn et al. (2011) *Nat. Biotechnol.* 29: 325-326) performed MS/MS analysis on total nsEV populations from serum pools comprising multiple specimens obtained from respective normal, PD, and amyotrophic lateral sclerosis (ALS) subjects. Eighty-two of the more than 1,000 nsEV proteins in the PD subject pool were absent from the normal subject pool while fifty-four of the PD pool proteins were absent from the ALS pool. Although AD specimens were not included, this work provides precedent for the utility of bloodborne nsEV proteomic analysis in AD biomarker discovery.

Similarly, two independent bloodborne nsEV candidate AD miRNA biomarker discovery efforts have yielded encouraging results. Cheng et al. (2015) *Mol. Psychiatry,* 20: 1188-1196) isolated total nsEVs from sixteen individual AD and thirty-six normal subject serum specimens. Deep sequencing of miRNA extracted from individual specimens identified over 1,400 miRNAs; 16 were either significantly increased or decreased in AD relative to normal nsEVs. This miRNA panel predicted AD with a sensitivity of 77%. Lugli and co-workers (Lugli et al. (2015) *PLoS One,* 10(10): e0139233) performed miRNA deep sequencing of nsEVs isolated from thirty-five each normal and AD subject plasma samples. This analysis identified 465 unique miRNAs; the difference between this number and the more than 1,400 miRNAs reported above results from differences in miRNA abundance thresholds for dataset inclusion. A machine learning algorithm identified seven miRNAs that were differentially expressed in AD subject nsEVs; this panel predicted subject disease status with greater than 80% sensitivity.

Only one miRNA, miR-342-3p, was shared between the above miRNA panels. It is likely that using different nsEV isolation protocols contributed to the lack of overlap between the two predictive miRNA panels. Regardless of these differences, the results of these studies demonstrate the plausibility of using transcriptomics in neuronal nsEV AD biomarker discovery; both these nsEV miRNA studies and the above proteomics study establish foundations for developing 3D neuronal nsEV omics analyses methods that yield highly translatable bloodborne neuronal nsEV protein and RNA profiles.

Isolation of Bloodborne Neuronal nsEVs

Modifying the total bloodborne nsEV omics analysis protocols used above to enable bloodborne neuronal nsEV profiling for AD biomarker discovery will involve resolution of several technical challenges.

Figure 11:
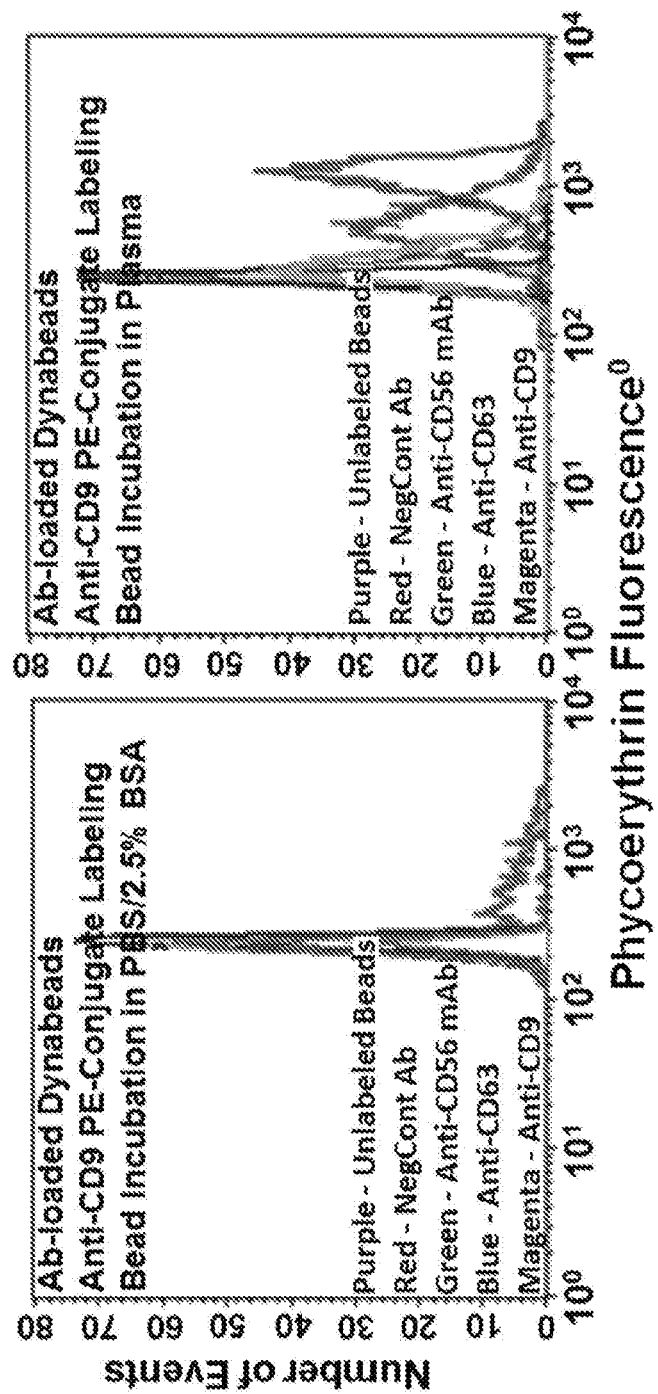
FIG. 11. Flow cytometry histograms showing ability to specifically enrich nsEVs from plasma using streptavidin-coated Dynabeads loaded with biotinylated Abs. After plasma incubation, magnetic particles were labeled with phycoerythrin (PE)-conjugated anti-CD9 Ab. Y-axis denotes number of magnetic particle events counted by flow cytometer and X-axis denotes PE fluorescence. Legends in lower left corner of histograms denote biotinylated Abs loaded onto magnetic particles. Left panel histogram corresponds to analysis of magnetic particles incubated with PBS/2.5% BSA rather than plasma; these histograms show that PE-conjugated anti-CD9 Ab has little or no propensity to nonspecifically bind Ab-loaded magnetic particles.

In seeking to improve upon the purity of nsEV populations isolated using various enrichment procedures we have found that nsEV IP methods employing three-micron diameter magnetic particles (Dynabeads—Life Technologies) loaded with antibodies (Abs) specific for proteins on nsEV surfaces yield high purity nsEV preparations (FIG. 11). These IP methods are extremely versatile; streptavidin-coated Dynabeads can be loaded with biotinylated Abs specific for any nsEV surface protein of interest. This versatility, combined with the high purity of enriched nsEV populations, place Dynabeads-based nsEV IP at the heart of our approach for 3D bloodborne neuronal nsEV analysis.

The high purity of Dynabeads-enriched nsEV populations is enabled by an avidity effect arising from respective nsEV and Dynabeads exteriors featuring multiple copies of surface proteins and nsEV surface protein-binding Abs. This avidity effect results in a near-covalent nsEV-Dynabeads interaction that allows one to perform multiple high stringency, e.g., pH below 3, wash steps after Dynabeads-plasma incubation without causing nsEV-Dynabead dissociation. High nsEV purity is obtained by virtue of the wash conditions abrogating the much weaker interactions between Dynabeads and contaminants that are nonspecifically adsorbed to Dynabead surfaces during incubation with plasma. Dynabeads IP is preceded by moderate centrifugation, e.g., 12,000 rcf for 20 minutes, and passage of plasma or serum through a centrifugal or syringe filter with a defined pore size, such as 0.5-micron polyethersulfone (PES). These upstream steps ensure that only plasma constituents presenting nsEV surface proteins of interest and possessing diameters below the filter pore size are enriched during IP. Such a Dynabead enrichment of nsEVs could be useful in the future for 3D nsEV analysis.

Two-Step Enrichment of Bloodborne nsEVs for Omics Analyses

Proteomic (Shi et al. (2014) *Acta Neuropathol.* 128: 639-650) and transcriptomic (Cheng et al. (2015) *Mol. Psychiatry,* 20: 1188-1196; Lugli et al. (2015) *PLoS One,* 10(10): e0139233) bloodborne nsEV CNS disorder biomarker discovery efforts reported to date have employed single-step procedures, e.g., UC or IP, to enrich nsEVs for subsequent protein or RNA extraction and omics analysis. Omics analyses that employ the serial Dynabeads IP procedures may increase one's ability to identify neuronal nsEV AD biomarkers relative to omics characterizations based on single-step nsEV enrichment. The low representation of neuronal nsEVs within the total bloodborne nsEV population (Fiandaca et al. (2015). *Alzheimers Dement.* 11: 600-607) could cause AD-associated differences in neuronal nsEV constituent abundances to be masked if non-neuronal bloodborne nsEV levels of these constituents are high and invariant across AD and normal subjects. Dynabeads enrichment of nsEVs based on neuronal surface marker proteins, such as CD56 and CD171, may prevent peripheral nsEV (note that CD56- or CD171-based IP enriches nsEVs derived from both peripheral and CNS neurons) and non-nsEV constituents from exerting this masking effect.

Enrichment of neuronal nsEVs for omics analysis is faciliateaed by isolation by IP with Abs recognizing different nsEV surface marker proteins such as Anti-CD9, anti-CD63 or anti-CD81. Ab-loaded Dynabeads or ExoCap nsEV IP kits (JSR Micro, Inc.) include an elution buffer that denatures the nsEV-binding Abs loaded onto the kit's magnetic particles, which are similar to Dynabeads, can be used for the IP. A three-minute incubation of magnetic particles in elution buffer followed by dilution with phosphate buffered saline solution to reduce protein denaturation rate dissociates nsEVs from magnetic particles without causing lysis.

Serial Dynabeads immunoprecipitation (IP) can also be facilitated by eluting anti-nsEV Abs from magnetic particles. CELLection Dynabead surfaces are covalently linked to anti-mouse or anti-biotin Abs by a DNA-based spacer arm. Murine-derived or biotinylated anti-nsEV surface marker protein Abs can be loaded onto CELLection Dynabeads by virtue of associating with the Abs coupled to the CELLection Dynabeads. After plasma incubation and washing, the addition of DNAse-containing reaction buffer releases the Ab-nsEV complexes from the Dynabeads. Ab-nsEV complex elution could also be achieved by using photocleavable linkers (Lim and Rothschild (2008) *Anal. Biochem.* 383: 103-115) to covalently couple Dynabeads to anti-nsEV surface marker protein Abs.

Quantifying Homogeneity of nsEV Preparations

Carrying out IP of neuronal nsEVs using Dynabeads loaded with anti-neuronal surface marker Abs does not pose elution-associated challenges (Shi et al. (2014) *Acta Neuropathol.* 128: 639-650); bound neuronal nsEVs can be lysed to allow isolation of protein and/or RNA for downstream omics analysis. The isolation of these protein and/or RNA pools should be complemented by estimating the fraction of enriched nsEVs that are neuron-derived; such estimation is needed to ensure that the protein and/or RNA pools being characterized in omics studies are in fact entirely or primarily derived from neuronal nsEVs.

Accurately estimating the fraction of enriched nsEVs that are neuron-derived is a somewhat complex pursuit. Ideal estimation methods would allow one to simultaneously confirm the presence of nsEV and cell type IP surface markers protein on individual nsEVs. Western blot quantification of intraexosomal marker proteins and neuronal surface marker proteins has been used to assess the homogeneity of "neuronal exosome" populations isolated by IP (Id.) but does not enlighten whether nsEV and neuronal marker proteins are colocalized to the same vesicle; verifying such colocalization requires nsEV imaging.

High nsEV homogeneity with respect to both nsEV and cell type marker proteins is expected for Dynabeads IP. As such, parallel electron microscopy [EM] experiments featuring nanogold-conjugated Ab-labeling (Id.) of respective nsEV and cell type surface markers allows accurate estimation of the percentage of double positive nsEVs. Consider the sample scenario in which 90% of the imaged nsEVs are CD9 (nsEV marker) positive and 75% are CD56 (neuronal marker) positive. In this case between 67.5% (0.9·0.75) and 75% of the isolated nsEVs are double positive. The relative range, i.e., upper limit divided by lower limit, of estimated double positive nsEV percentages increases considerably with decreasing nsEV homogeneity. As such, this estimation approach is uniquely enabled by the high enrichment techniques such as achieved by Dynabeads IP.

nsEV Omics Analysis Requirements & Technical Considerations

There are several technical considerations that are important for generating nsEV omics datasets that would enable 3D nsEV analysis. Specimen volume requirements are at the top of this list. Neuronal nsEVs are reported to account for approximately 15% of the total bloodborne nsEV population (Fiandaca et al. (2015). *Alzheimers Dement.* 11: 600-607). Based on this estimate and specimen volumes used in prior omics studies, ensuring adequate neuronal nsEVs for low-abundance candidate biomarker detection would require more than 30 mL of plasma for individual specimen proteomic profiling (Feng et al. (2010) *Traffic,* 11(5): 675-687) and at least 3 mL of plasma for transcriptomic profiling (Cheng et al. (2015) *Mol. Psychiatry,* 20: 1188-1196; Lugli et al. (2015) *PLoS One,* 10(10): e0139233). The difficulty in obtaining 30 mL of plasma from single subjects will likely necessitate that three-dimensional proteomic analyses be performed using pooled specimens. Given that plasma nsEV concentration varies across samples (Muller et al. (2014) *J. Immunol. Meth.* 411: 55-65), use of nsEV quantification methods, such as NanoSight counting or commercial nsEV surface marker ELISA, could help ensure equal representation of samples comprising specimen pools. We also note that Abs for neuronal nsEV enrichment must be covalently coupled to Dynabeads to avoid dissociation of biotinylated Abs from streptavidin-coated Dynabeads during protein extraction as dissociated Abs contaminate nsEV protein extracts and thus compromise the quality of data obtained during MS/MS omics analysis of nsEV protein constituents.

Next-Generation Tools for nsEV Analysis

Obtaining neuronal nsEV omics datasets using methods described above will provide omics analyses with even greater translational potential. Next-generation analyses could be enabled by advances in two emerging areas: microfluidic devices that sort blood-borne neuronal nsEV subpopulations directly from plasma based on abundances of multiple nsEV surface markers and engineered Abs or aptamers that bind epitopes exclusive to AD neuronal nsEV exteriors.

There are two primary obstacles, which arise from nsEV volumes being 106-fold lower than cell volumes, to flow cytometric sorting of individual nsEVs. First, nsEV flow rate must be controlled to prevent "swarming", a phenomenon causing groups of nsEVs to be detected as single fluorescence events and leading to encapsulation of multiple nsEVs within sorted fluid droplets (Kormelink et al. (2015) *Cytometry A.* doi: 10.1002/cyto.a.22644). Second, fluorescent Ab-labeled nsEV fluorescence is low relative to the autofluorescence of unlabeled nsEVs and plasma constituents such as cellular debris and protein aggregates. The resulting poor signal-to-noise ratio combines with the effects of swarming to preclude sorting of nsEVs directly from plasma using contemporary flow cytometers; the most advanced plasma-borne nsEV flow cytometry protocols reported to date enable only nsEV analysis (Danielson et al. (2016) *PLoS One.* 11(1): e0144678). The utility of these cytometry methods is further limited by the facts that they do not allow the detection of nsEVs having diameters less than 100 nm and that they are incompatible with fluorescent Ab labeling of plasma-borne nsEVs; analyzed nsEVs have been characterized based on only size and morphology.

Figure 12:
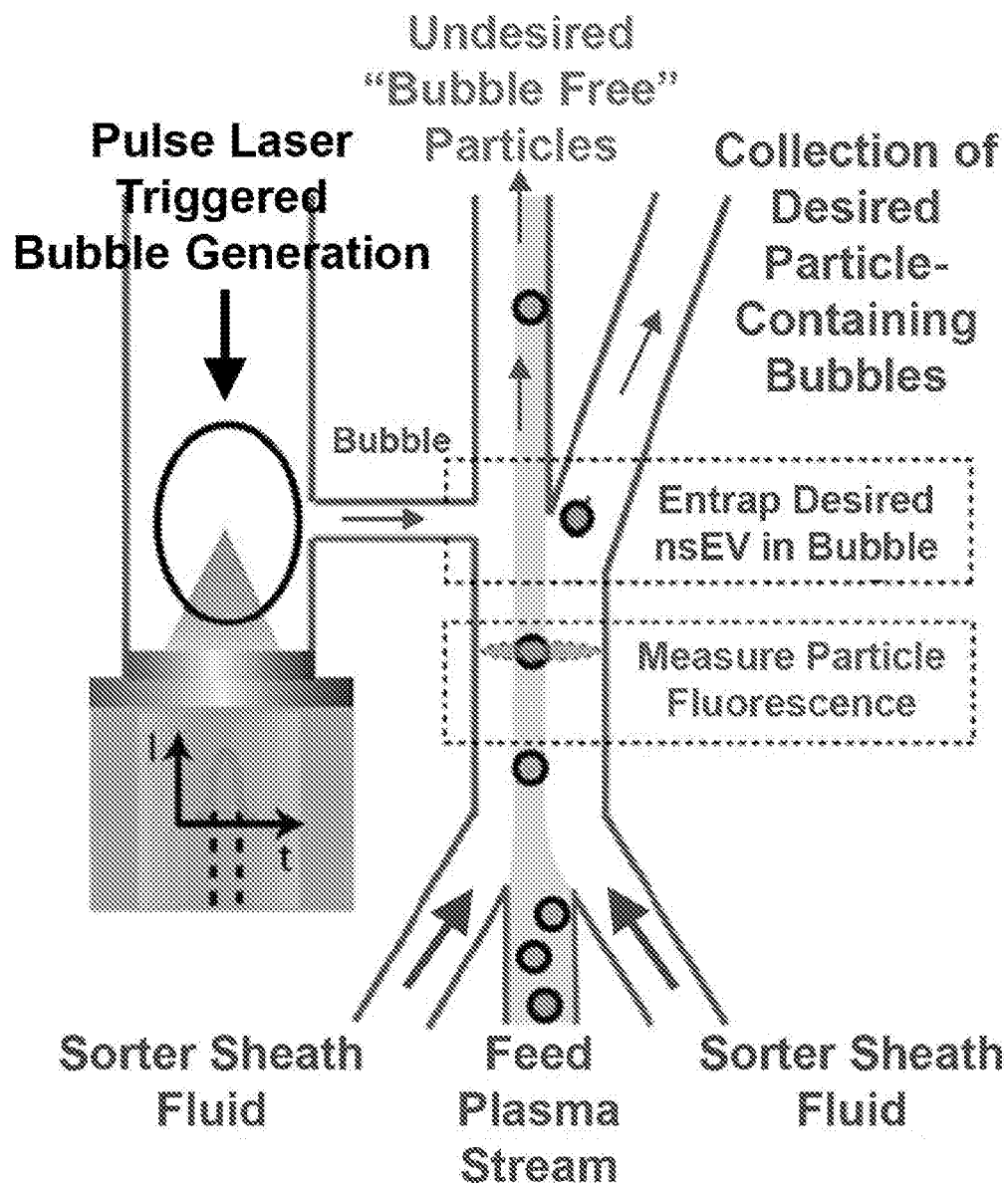
FIG. 12. PLACS nsEV sorter schematic. Single nsEVs with desired fluorescence properties, e.g., binding by nsEV surface marker- and cell type surface marker-specific fluorescent Abs, are isolated from the bulk plasma nanoscale particle population by high speed fluid jets. These fluid jets are generated by picoliter scale bubbles that are triggered by pulsed laser-induced cavitation. The PLACS sorting module sorts nanoparticles at rates (~30,000/sec) comparable to those for state-of-the-art flow cytometers while providing the advantage of being able to isolate individual nsEVs from the overall particle population. Conventional flow cytometers entrap sorted nsEVs in nanoliter scale liquid droplets; droplets of this size typically encase multiple nsEVs and prevent high purity enrichment of individual nsEVs from the bulk plasma nanoscale particle population.

Further development of existing nonstandard flow cytometers could allow swarming and autofluorescence issues to be overcome. Regarding swarming, Pulse Laser Activated Cell Sorter (PLACS) microfluidics devices (Chen et al. (2014) *Small.* 10: 1746-1751) achieve exquisite control over particle flow rate and can encapsulate sorted particles in liquid volumes less than 100 picoliters (FIG. 12). Time-gated flow cytometers (Jin et al. (2009) *J. Biomed. Opt.* 14(2): 024023; Jin et al. (2007) *Cytometry A.* 71(10): 783-796), which detect the long-lived photon emissions of lanthanide-conjugated Abs, can improve nsEV detection signal-to-noise ratios by quantifying long-lived lanthanide emissions while filtering out short-lived autofluorescence emissions. Hybrid instruments integrating PLACS fluidics and time-gated optics could be effective apparatuses for sorting individual nsEvs.

Proteins with post-translational modifications such as glycation, glycosylation, and nitration (Chick et al. (2015) *Nat. Biotechnol.* 33: 743-749; Gallart-Palau et al. (2015) *Int. Rev. Neurobiol.* 121: 87-116; Stevens et al. (2008) *Mol. Cell Proteomics.* 7: 2442-2451) can go undetected or be misidentified by MS/MS proteomic analysis. Additionally, MS/MS proteomics cannot distinguish among different protein conformational isoforms or oligomers. These limitations motivate augmenting panels of candidate AD biomarkers identified using MS/MS proteomics by carrying out nsEV probe (Abs and/or aptamers) library screens to isolate probes binding epitopes unique to or highly enriched on AD bloodborne neuronal nsEV surfaces. Such probes can be used to immunoprecipitate the proteins carrying AD-specific epitopes for sequence deconvolution (Sharma et al. (2007) *Clin. Cancer Res.* 13: 5889-5896; Van Simaeys et al. (2014) *Anal. Chem.* 86: 4521-4527).

Antigen-loaded Dynabeads are routinely used for probe library screening (Cho et al. (2013) *Proc. Natl. Acad. Sci. USA*, 110: 18460-18465). As such, performing multiple rounds of alternating negative and positive probe library screens (Van Simaeys et al. (2014) *Anal. Chem.* 86: 4521-4527; Jones et al. (2014) *Biotechnol J.* 9: 664-674) with respective normal and AD bloodborne neuronal nsEV-loaded Dynabeads should yield probes that immunoprecipitate nsEV surface proteins that present AD biomarker epitopes.

Multicolor nsEV cytometry with various combinations of AD nsEV-specific probes and/or commercial Abs against AD nsEV biomarker surface proteins identified by proteomic profiling can address the important question of whether the overall blood-borne neuronal nsEV population is comprised of distinct subpopulations featuring different combinations of AD-specific surface proteins and/or epitopes. Sorting nsEV subpopulations would facilitate downstream omics and/or individual AD biomarker analyses that may enlighten both cell-to-cell heterogeneity of AD-associated changes in neuronal molecular composition and the existence of neuronal nsEVs that carry distinct groups of signaling molecules. Knowledge of such heterogeneity and distinct modes of intercellular communication could enlighten the interplay among different mechanisms of AD pathology and thus be a valuable facilitator of AD drug target identification and therapeutic development.

With respect to forthcoming developments in the area of neuronal nsEV diagnostics hardware for clinical applications, recent progress in miniaturizing complex laboratory operations suggests that the future may prove to hold substantial advances in terms of constructing portable devices for point-of-care quantification of neuronal nsEV biomarkers. Regarding the specifics of this recent progress, protein microarray-based multiplex fluorescent ELISA assays (Ludwig et al. (2015) *PLoS One*, 10(8): e0134360) and accurate pinprick volume blood sample HIV diagnosis (Laksanasopin et al. (2015) *Sci. Transl. Med.* 7(273): 273re1) can both now be carried out using handheld peripheral devices that are compatible with smartphones. Given these impressive achievements, the above envisioned development of portable instruments for quantifying bloodborne neuronal nsEV biomarkers appears to be a realistic goal.

CONCLUSION

Advances in neuronal nsEV isolation and characterization methods and analysis protocols that leverage neuronal nsEVs could provide "windows into the brain" using non-invasive diagnostic assays, requiring only microliters of blood obtained during routine doctor's office visits, that quantify Alzheimer's Disease (AD) biomarker proteins in nsEVs. Such assays could enable rapid diagnosis for CNS disorders and facilitate the development of personalized treatment programs. Continued increases in public and private funding for nsEV-focused research should enable realization of this goal in a timely manner and hasten the development of the next generation nsEV analyses that provide a more accurate analysis of AD biomarkers in plasma. Although it will take time, as has been the case for the human genome sequence, to translate omics-derived AD biomarker discoveries from bench-to-bedside, it is clear that the ever-increasing convergence of biomedical research will augment the relative rate of translation. As such, it is anticipated that we are only years, rather than decades, away from seeing drugs and/or therapeutic modalities inspired by 3D bloodborne neuronal nsEV analyses that have a clinical impact in treating this devastating disease.

Example 3

Synthesis of Triorthogonal Linkers

Figure 17:
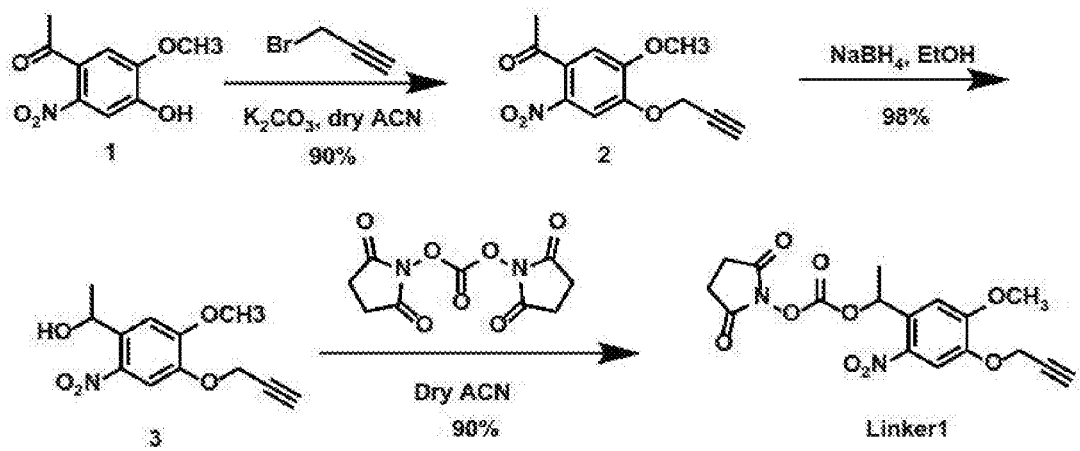
FIG. 17 illustrates synthesis Scheme 3 for the synthesis of linker 1 (see, e.g., Kaneko et al. (2011) *Phys. Chem. Chem. Phys*. 13: 4051-4059).

In certain embodiments the triorthogonal linkers can be synthesized using Scheme 3, shown in FIG. 17, or variants thereof.

5-Methoxy-2-nitro-4-prop-2-ynyloxyacetophenone (2)

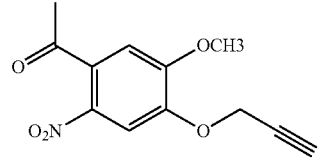

To a round-bottom flask containing anhydrous acetonitrile solution (5 mL) of 4-hydroxy-5-methoxy-2-nitroacetophenone (100 mg, 0.47 mmol) and anhydrous potassium carbonate (91 mg, 0.66 mmol) was added 3-bromoprop-1-yne (47 µL, 0.62 mmol). The solution was subsequently refluxed at 100° C. for 4 h under nitrogen atmosphere. After reducing the mixture on a rotary evaporator, water (20 mL) and 2 M HCl (2.5 mL) were added, and the solution was extracted with DCM (3×25 mL). The organic layer was dried over $MgSO_4$, and the solvent was removed under a reduced pressure to yield 105 mg (0.42 mmol, 90%) of 2 as a yellowish powder. The reaction was repeated twice.

1-(5-Methoxy-2-nitro-4-prop-2-ynyloxyphenyl)ethanol (3)

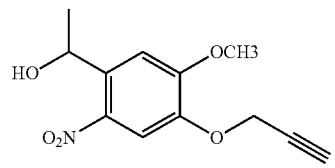

To a solution of 2 (120 mg, 0.49 mmol) in THF (10 mL) and methanol (20 mL) on an ice bath sodium tetrahydroborate (120 mg, 3.4 mmol) was added. The reaction mixture was left stirring on an ice bath for 6 h. After reducing the reaction mixture on a rotary evaporator, $H_2O$ (50 mL) and 2 M HCl (5 mL) were added, and the solution was extracted with dichloromethane (3×40 mL). The organic layer was dried over $MgSO_4$, and the solvent was removed under a reduced pressure to yield 119 mg (0.48 mmol, 98%) of 3 as a yellowish powder.

1-(5-Methoxy-2-nitro-4-prop-2-ynyloxyphenyl)ethyl N-succinimidyl carbonate (Linker 1, L1)

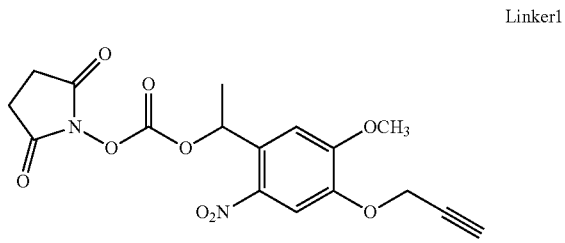 [SMILES: C#CCOc1cc([N+](=O)[O-])c(C(C)OC(=O)ON2C(=O)CCC2=O)cc1OC]

Linker1

N,N'-Disuccinimidyl carbonate (336 mg, 1.31 mmol) and triethylamine (183 µL, 1.31 mmol) were added to a solution of 3 (110 mg, 0.44 mmol) in 10 mL of dry acetonitrile. The reaction mixture was stirred at room temperature for 8 h under nitrogen atmosphere. After reducing the reaction mixture on a rotary evaporator, $H_2O$ (30 mL) and 2M HCl (5 mL) were added, and the solution was extracted with dichloromethane (3×40 mL). The organic layer was washed with saturated $NaHCO_3$ (3×80 mL) and dried over $MgSO_4$. The resulting organic layer was finally concentrated under reduced pressure to yield 155 mg (0.39 mmol, 90%) of linker 1 (L1) as a yellowish powder. The linker 1 obtained was stored in Drierite at −20° C.

Coupling of Photocleavable Linker with Azide Magnetic Beads.

Coupling of the photo cleavable linker (e.g., linker 1, see FIG. 16) with azide magnetic beads can readily be achieved by copper-free click chemistry (see, e.g., FIG. 13). Click reaction involving linker 2 (see FIG. 16) and azide magnetic beads can be realized in DMSO, $CHCl_3$, and acetonitrile. If the reaction demands use of only PBS, linker 3 (see FIG. 16) can be used as it has a sulfo group which makes it readily soluble in PBS or water.

Example 4

Preparation of Immuno-Photolytic Beads via Click Conjugation of the Azide Magnetic Beads with Linker Although it might be possible to use other magnetic microspheres for nsEV capture, we have obtained satisfactory results using the azide magnetic beads from Jena Bioscience (Jena, Germany). This product allows the user to covalently couple any desired linker to the surface of the azide magnetic microspheres using a Cu(I)-catalyzed azide-alkyne cycloaddition (CuAAC) or a Cu(I)-free azide-DBCO click chemistry reaction. For target-specific exosome enrichment and isolation capturing antibodies were conjugated onto linker-magnetic beads by employing NHS-ester chemical pathway possible with triorthogonal linker.

The first step in executing the ExoTIP technique is carrying out click conjugation of azide magnetic beads with linker of interest. We have generally prepared beads-linker-antibody conjugates in 50 µL batches whereas each click conjugation was initiated with 0.5 mg (50 µL, 10 mg/mL) azide magnetic beads (21.8 nmol of azide). Briefly, to an Eppendorf tube 0.5 mg (21.8 nmol) of the azide magnetic beads were taken and washed with degassed DMSO. Beads were resuspended in 100 µL of degassed DMSO and subsequently linker1 (0.86 mg, 2.2 µmol, pre-dissolved in 100 µL DMSO), $CuSO_4.5H_2O$ (0.54 mg, 2.2 µmol, pre-dissolved in 100 µL DMSO) and sodium ascorbate (1.74 mg, 8.8 µmol, pre-suspended in 200 µL DMSO) were added. In an alternative approach, owing to the low solubility of sodium ascorbate in DMSO, sodium ascorbate (1.74 mg, 8.8 µmol, pre-suspended in 10 µL PBS (pH=5.4)) was also used. The tubes were rotated on a lab rotor for 30 minutes. After rotation, tubes were washed promptly with 500 µL of DMSO and then with 500 µL PBS (pH=5.4). Between each wash step magnetic beads were drawn to the side of the 1.5 mL microcentrifuge tubes in which all incubations were carried out using a DYNAMAG™ and the wash supernatant was removed by pipetting. After the first wash step and resuspension in PBS (pH=5.4) magnetic beads were transferred to a new microfuge tube to minimize carryover of unbound linker or copper; such carryover can harshly affect the antibody and its coupling ability to the linker. After washing the beads with PBS (pH=5.4), 30 µL of ten times-diluted L1CAM-specific antibodies (1 mg/mL) with PBS (pH=7.8) was added in each tube. Conjugation of L1CAM antibodies proceeded on a lab rotator for 30 min at room temperature and was followed by five one-minute wash steps: PBS/0.1% TWEEN® 20 (Polyethylene glycol sorbitan monolaurate) and one wash with PBS. After the first wash step and resuspension in PBS/0.1% TWEEN® 20 magnetic beads were transferred to a new microfuge tube to minimize carryover of unbound antibody; such carryover can increase background signal upon quantifying nsEV surface marker proteins.

Example 5

ExoTIP Technique (Immuno-Photolytic Capture and Release of Neuronal Exosomes)

For carrying out ExoTIP with standard specimens, 492 µL of PBS/0.1% BSA/0.1% dextran500/1:500 PIC/1:500 EDTA was added to 8 µL of exosome standard (1 µg/µL) in a 2.0-mL low retention Eppendorf tube. Immunoprecipitation of nsEVs was allowed to proceed overnight at 4° C. with rotation on a lab mixer. Immunoprecipitation was followed by four washes: one minute in PBS with 0.1% bovine serum albumin (BSA), ten minutes with rotation on a lab mixer in the low-pH buffer (pH=5), a repeat of this low-pH wash step, and a final one-minute wash in PBS/0.1% BSA. Between each wash step magnetic beads were drawn to the side of the 1.5-mL microcentrifuge tubes in which all incubations were carried out using a DYNAMAG™ and the wash supernatant was removed by pipetting. After the first wash step and resuspension in low-pH buffer (pH=5) magnetic beads were transferred to a new microfuge tube to minimize carryover of unbound exosomes. Five-hundred microliter of wash buffer was used for each wash step After the wash step magnetic beads were subsequently resuspended in 150 µL of PBS (pH=7.4) in a 1% BSA pretreated Corning 12-well plate (plate was treated at RT for 2 h with 1% BSA and subsequently washed with 500 µL of PBS) and exposed to UV light (e.g., λ=365 nm) for e.g., about 5 minutes up to about 60 minutes and in certain embodiments about 40 minutes from the top (approximately one inch distance) on a shaker. After the UV exposure, supernatant enriched with exosomes along with magnetic beads were collected in microfuge tubes and subsequently enriched sups were pipetted after drawing the beads to the sides using Dynamag. Supernatants were further tested using AlphaLISA.

Biotinylation of Antibodies

Antibodies were labeled with NHS-biotin (Thermo Scientific) according to manufacture protocol. Briefly, all antibodies were purified from sodium azide and buffer was exchanged to PBS using Zeba spin desalting columns, 7K MWCO (Thermo Scientific) prior to biotinylation, and incubated with NHS-biotin (freshly made 10 mM solution in DMSO) at 30:1 molar ratio of biotin to antibody for 30 minutes at RT, followed by purification from free biotin using Zaba Spin columns.

Stability of Exosomes from UV Exposure

Since UV light ($\lambda$>360 nm) was used to achieve photolytic release of captured neuronal exosomes, we have tested standard exosomes stability under the similar condition i.e. UV exposure in the same environment as ExoTIP technique. Briefly, 2 µL of exosomes from a stock of standard exosomes at 1 µg/µL was diluted in PBS (pH=7.4) to 150 µL final volume in a 1% BSA pretreated Corning 12-well plate and exposed to UV light (1=365 nm) for 40 minutes from top (approximately one inch distance) on a shaker. After the UV exposure, exosomes were collected and subsequently tested using AlphaLISA. AlphaLISA screen reveals that there is no apparent change in signal due to UV exposure of exosomes when compared to the signal obtained from standard exosomes itself.

Stability of Exosomes from UV Exposure

Figure 18:
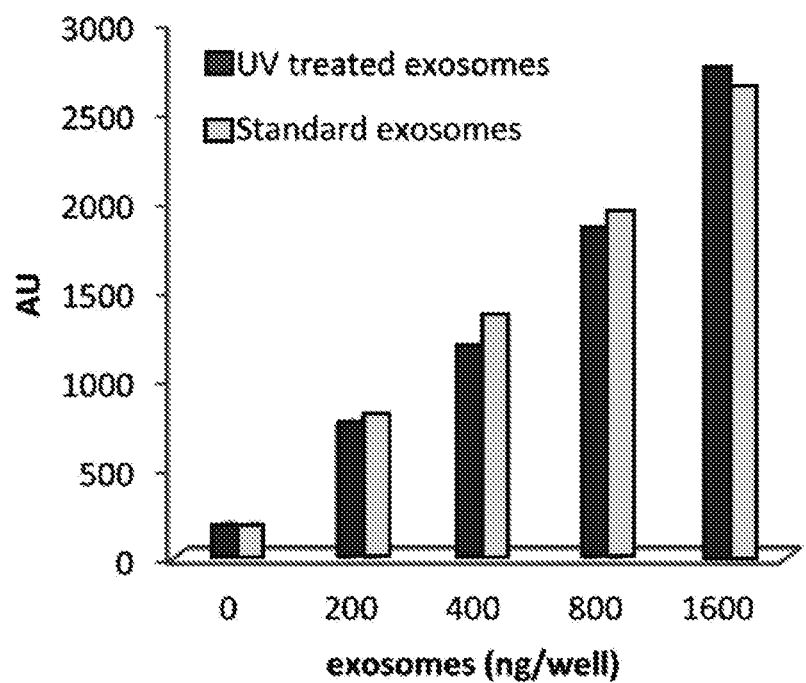
FIG. 18 shows a comparison of signals for standard and UV treated exosomes using AlphaLISA. No significant difference has been observed after UV exposure to exosomes.

Since UV light ($\lambda$>360 nm) was used to achieve photolytic release of captured neuronal exosomes, we have tested standard exosomes stability under the similar condition i.e. UV exposure in the same environment as ExoTIP technique. Briefly, 2 µL of exosomes from a stock of standard exosomes at 1 µg/µL was diluted in PBS (pH=7.4) to 150 µL final volume in a 1% BSA pretreated Corning 12-well plate and exposed to UV light (1=365 nm) for 40 minutes from top (approximately one inch distance) on a shaker. After the UV exposure, exosomes were collected and subsequently tested using AlphaLISA. AlphaLISA screen reveals that there is no apparent change in signal due to UV exposure of exosomes when compared to the signal obtained from standard exosomes itself (see, e.g., FIG. 18).

ExoQUANT—using Amplified Luminescent Proximity Homogeneous Assay—LISA (AlphaLISA)

Quantification of number of nsEVs released by photolytic cleavage from the beads would be done by AlphaLISA. We have also used Flow Cytometry, DLS and TEM to further analyze our samples. AlphaLISA technology is based on the detection of the signal coming from acceptor beads (A) if energy is transferred to them from donor beads (D) by singlet oxygen upon excitation of the donor beads with a certain wave length of light. This occurs when D and A come to close proximity, for example, by binding to the same analyte or by binding different analytes present on a common substrate (e.g., a common exosome). The signal produced by the reactions described herein can be read by methods known to those of skill in the art. In certain embodiments the assay reactions are performed in a multi-wall plate and the reaction signal(s) are read using a plater reader (e.g., Perkin Elmer's Enspire plate reader, or other suitable plate reader).

In one illustrative, but non-limiting embodiment the method was performed as follows:

Step 1. 20 µL of a sample containing immune-photolytically enriched exosomes, were added into 96 well assay plate, mixed with 5 µl either empty acceptor beads (100 µg/ml in AlphaLISA universal buffer, containing 0.1% Dextran 500) or 5 µl of 100 µg/ml acceptor beads conjugated to the anti-CD9 or anti-CD63 antibodies (Cosmo Bio Co., LTD).

Step 2. Biotinylated anti-CD9 or anti-CD63 antibodies (Cosmo Bio Co., LTD), biotinylated isotype control antibodies (BioLegend) or anti-Aβ antibodies MOAB-2 (abcam) or 12F4 (BioLegend) were added to each well (5 µl of 20 nM antibodies per well) and incubated for 60-120 minutes at RT.

Step 3. Streptavidin conjugated donor beads (20 µl of 100 µg/ml beads per well) were added to the reactions and incubated for 30 minutes at RT.

Step 4. AlphaLISA signal from each well was detected by Perkin Elmer's Enspire plate reader (total time: 400 ms; excitation time: 100 ms; distance: 0.2 mm).

Figure 19:
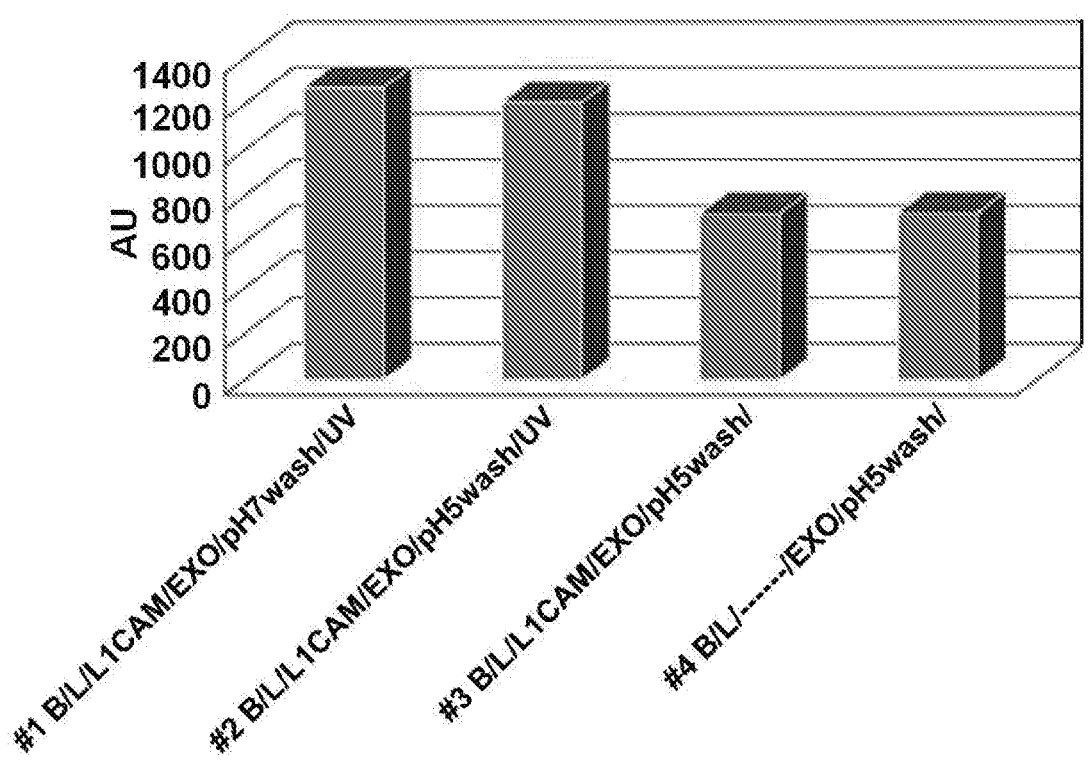
FIG. 19 shows AlphaLISA signal (CD9/CD9) for the supernatant enriched with exosomes after ExoTIP isolation. In the tube 1, unbound exosomes from ExoTIP-beads-exosomes were washed off using buffer (pH=7) while in all other tubes unbound exosomes were washed off using buffer (pH=5). Tubes 1 and 2 (sup used was obtained after UV exposure of ExoTIP-beads-exosomes) showed higher signals compared to tubes 3 and 4 (sup used was obtained without UV exposure of ExoTIP-beads-exosomes and hence fewer exosomes).

Results showing the AlphaLISA signal (CD9/CD9) for the supernatant enriched with exosomes after ExoTIP isolation are shown in FIG. 19.

Flow Cytometry Analysis

Figure 20:
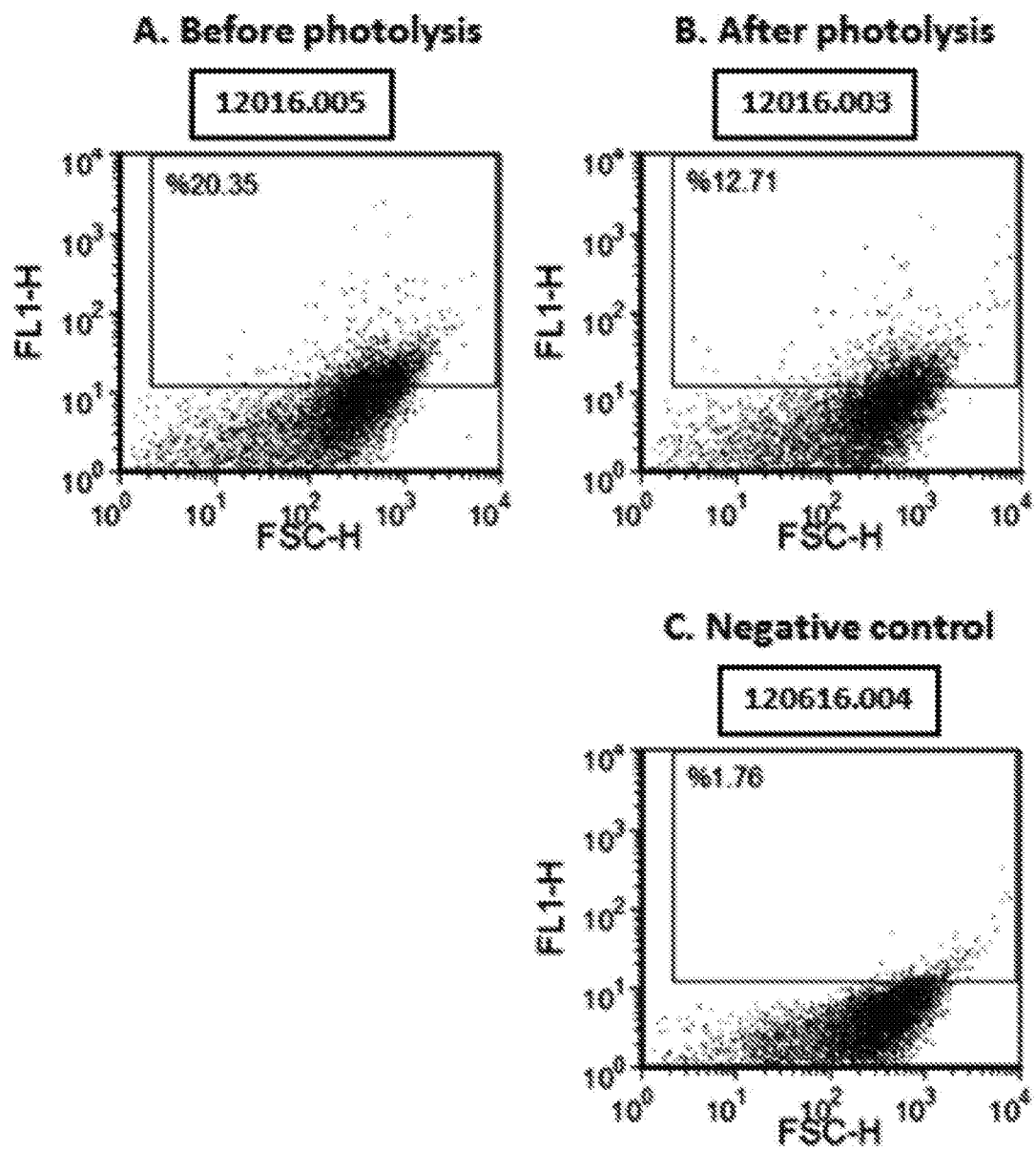
FIG. 20, panels A-C, shows the results of flow cytometry analysis of CD9-positive nsEVs on anti-L1CAM-coated magnetic beads during the course of Exo-TIP isolation. Representative dot plots show CD9 signal before photolytic release of neuronal exosomes (panel A), after the release (panel B) and background level of staining in the absence of CD9-specific antibodies (panel C).

We detected CD9-positive nsEVs, immobilized on the L1CAM-coated ExoTIP beads before and after photolytic reactions in order to monitor efficiency of immunoprecipitation and release of nsEVs in course of the isolation (see, e.g., FIG. 20). Equal amounts of ExoTIP L1CAM coated beads were used for nsEV immunoprecipitation, followed either by photolytic release of nsEVs, as described above, or by 40 minutes shaking at room temperature without exposure to UV light. The beads were collected on the magnet, washed 3 times with 0.1% BSA/PBS and incubated with biotinylated CD9-specific antibodies in 2.5% BSA/PBS either for 2 hrs at RT or ON at 4 C, followed by one wash with 1% BSA/PBS and 2 washes with 0.1% BSA/PBS. After the last wash beads were incubated with Streptavidin conjugated Alexa 488 in 2.5% BSA/PBS in dark for 30 minutes at RT, followed by wash in 1% BSA/PBS and two consecutive washes in 0.1% BSA/PBS. After the last wash beads were resuspended in PBS for flow cytometry analysis. Data were acquired with the use of a BD-FACS Calibur analytical flow cytometer. Alexa 488 were detected by FL-1 channel, 10,000 events were collected and analyzed using FCS Express software (see, e.g., FIG. 20).

Immunogold Labelling of Standard Exosomes

Figure 21:
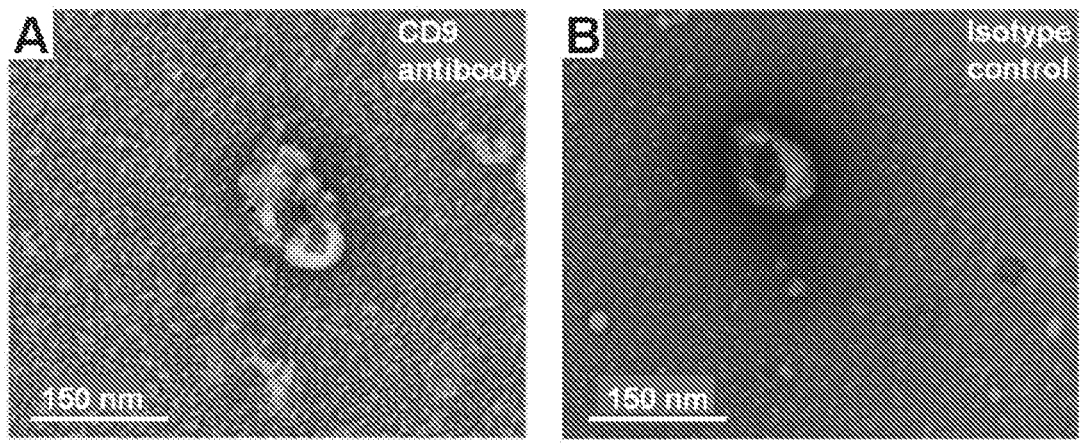
FIG. 21, panels A-B, shows immunogold characterization of standard exosomes. Gold-bound anti-CD9 antibodies were localized on the surface of the exosomes (panel A) whereas the localization was not seen with isotype control (panel B).

Ultrastructure studies of cellular antigens have been well studied using validated immune-electron microscopy technique (Harven (1984) *J. Cell Biol.* 99: 53-57). We have employed widely used "two step" method, which involves first treatment with primary antibodies and subsequent detection of antigen with immunogold conjugate reagent in the second step. Our EM analysis shows the localization of immunogold-nanoparticles (~15 nm), bound to the membrane of the exosomes which showed a characteristic cup-shaped nsEVs with size ranging from 30-130 nm diameter (see, e.g., FIG. 21).

Transmission Electron Microscopy (TEM)

Figure 22:
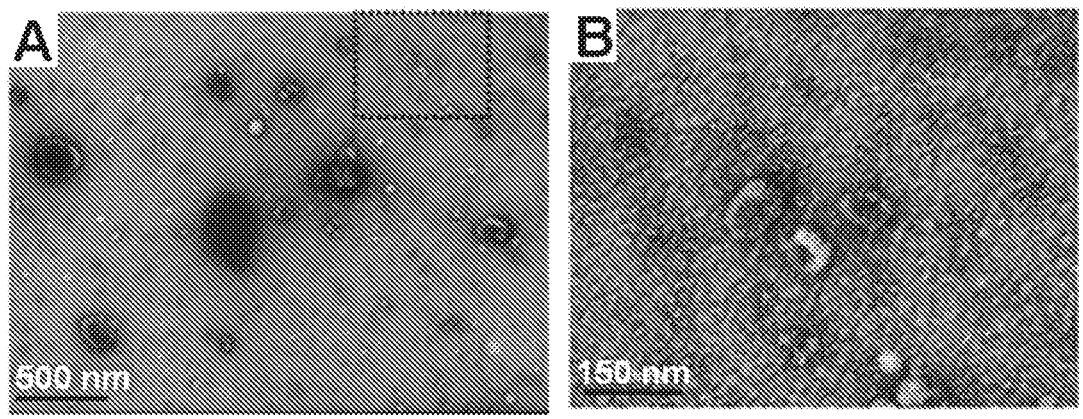
FIG. 22, panels A-B, shows transmission electron micrographs of standard exosomes. Two microliter of exosome stock at 1 µg/µL was diluted ten times for reverse drop staining of copper mesh. Inset in panel A is shown as panel B.
Figure 23:
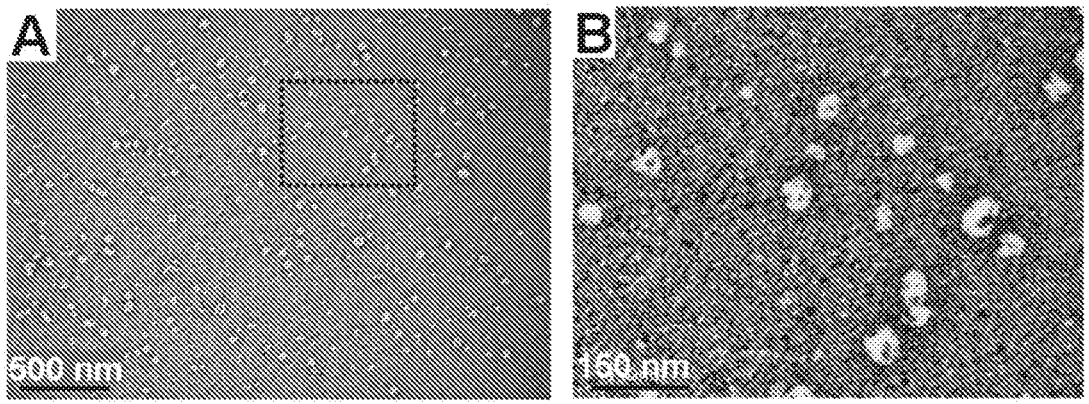
FIG. 23, panels A-B, shows transmission electron micrographs of purified exosomes using ExoTIP and utilizing linker 1. Twenty microliter of supernatant collected after photolytic release of exosomes was used for reverse drop staining of copper mesh. Inset in panel A is shown in panel B.
Figure 24:
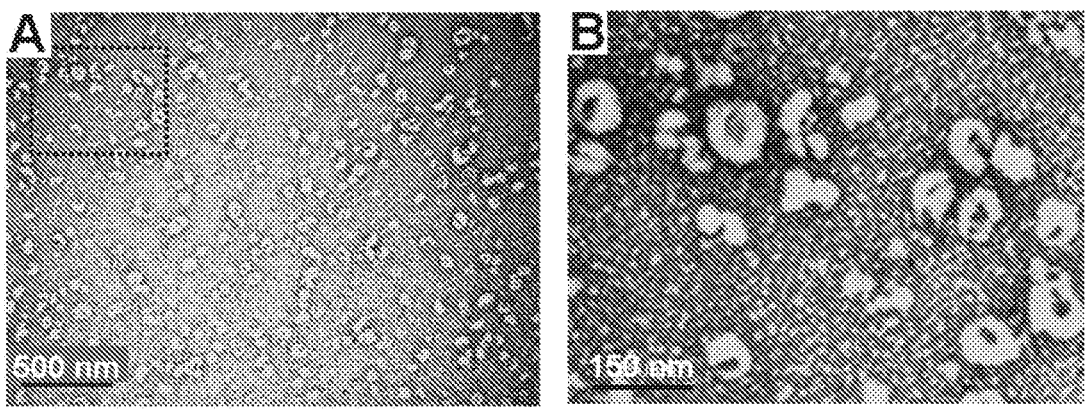
FIG. 24, panels A-B, shows transmission electron micrographs of purified exosomes using ExoTIP and utilizing linker 1 but using alternative click condition in step 1. Twenty microliter of supernatant collected after photolytic release of exosomes was used for reverse drop staining of copper mesh. Inset of panel A is shown in panel B.

Twenty microliter of the supernatant obtained by the UV photolytic release, enriched with exosomes, was absorbed onto a copper mesh (EMScience, Cat #FCF400-Cu) for 30 minutes (reverse drop technique), followed by wicking of excess fluid and subsequently fixation with 10 µL glutaraldehyde/PFA for two minutes. Excess glutaraldehyde/PFA was wicked off and copper meshes were further washed three times with ddH2O. Following the wash step, they were stained with 2% uranyl acetate solution for two minutes and excess stains were subsequently wicked off. They were then imaged on a JEOL 100CX electron microscope at 29,000 times magnification (see, e.g., FIGS. 22-24).

Dynamic Light Scattering (DLS)

Figure 25:
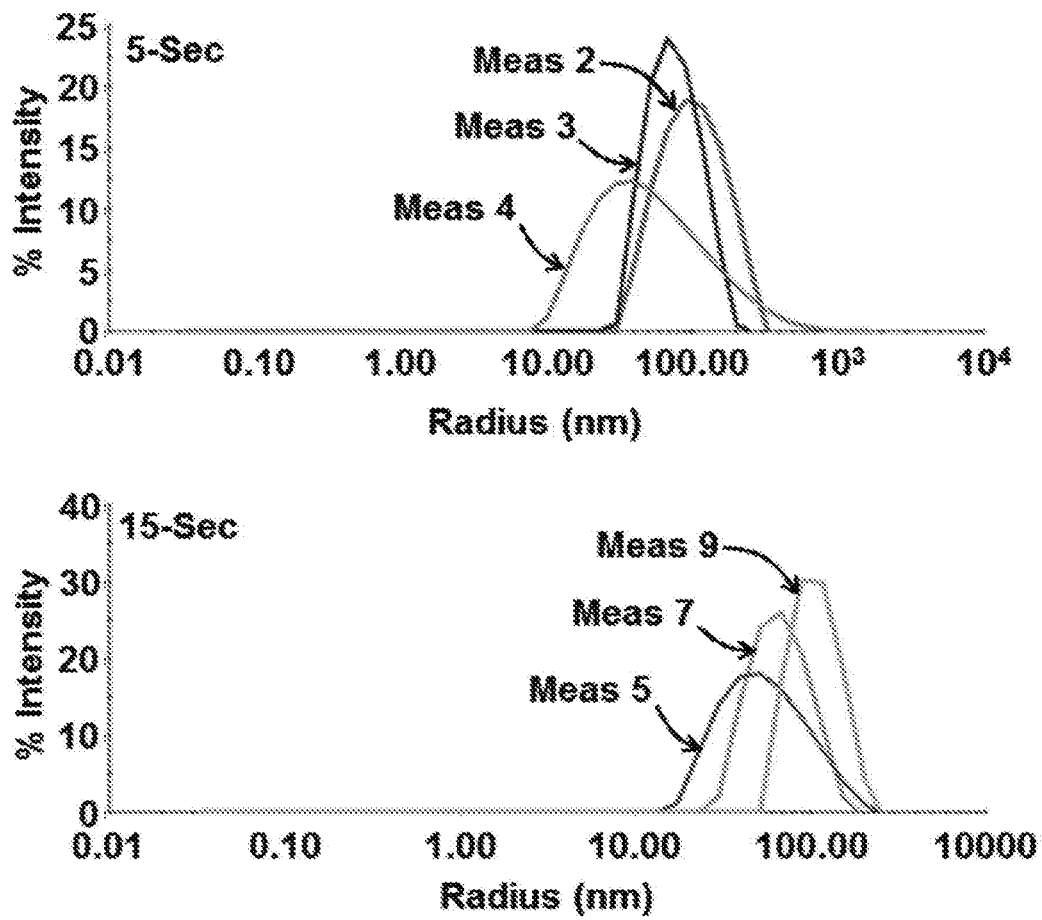
FIG. 25 shows the size distribution of nsEVs analyzed using Wyatt Technology DLS. *For sample 2 click reaction was performed only in DMSO, as compared to sample 1 where sodium ascorbate was dissolved in PBS (pH=5.4).

Twenty microliter of each samples were run on a Wyatt Technology DLS for 5-sec and 15-sec acquisition time. Size suggested by DLS was in good agreement with the size obtained by TEM analysis. In our experiment, we have observed exosomes size in the 30-130 nm range (see, e.g., FIG. 25).

Exosome Isolation from Synaptosomes (AD Patients and NL Subject Synaptosomes)

Figure 26:
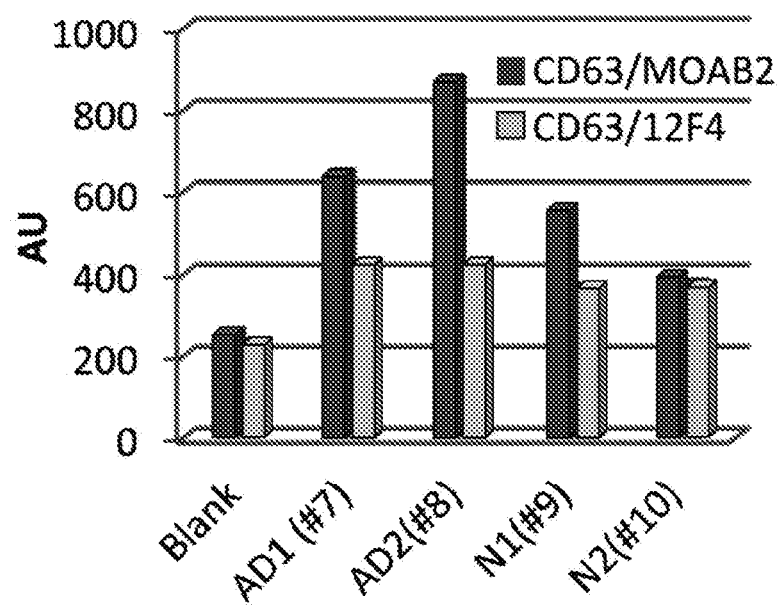
FIG. 26 shows a graphical depiction of elevated levels of Aβ on the surface of AL1CAM/CD63-positive exosomes from AD patient synaptosomes compared to NL subject synaptosomes using two different Aβ-specific antibodies.

ExoTIP technique was used to isolate exosomes from the synaptosome samples belonging to AD patients and NL subjects. The procedure was similar as was used for neuronal exosomes isolation from standard exosomes, only here ExoTIP beads were incubated with five times diluted synaptosomes. Dilution was done to make the sample less viscous which facilitate efficient conjugation with the ExoTIP beads and better isolation. We have demonstrated elevated levels of Aβ on the surface of L1CAM/CD63-positive exosomes from AD patient synaptosomes compared to NL subject synaptosomes using two different Aβ-specific antibodies (FIG. 26). The method may be utilized for non-invasive early diagnosis of AD, monitoring of drug treatment effects, and identification of markers and targets for new therapeutic approaches in AD.

Exosome Isolation from Plasma/Serum.

Our approach can further be extended where ExoTIP platform can be pre-installed on a 96-well plate/48-well plate/24-well plate. In that scenario, ExoTIP plates will ready to extract diseases specific markers (e.g. Aβ derived from neuron specific exosomes) directly from the plate.

ExoTIP capture can be pre-installed on PDMA glass microfluidic chips using soft lithography, where miniature pump (able to pump microliter quantity of fluid) will be used to push the exosomes source (viz. saliva, plasma, serum, CSF etc.). This approach will help in expediting and automating the exosomes capture, subsequent washing, release and collection and ExoQuant analysis by AlphaLISA. The data from these analysis can be captured using smart phone like device that eventually could lead to a point of care (such as a clinic) exosome analysis for neurological disorders.

Conclusion

Our maximum start concentration was ~$8\times10^8$ which is ten times diluted sample as compared to the recent report by Nakai et al. (2016) *Sci. Rep.* 6: 33935, presented detection of more concentrated preparation, in the range of $1\times10^{10}$.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of identifying and/or quantifying one or more antigens of interest (biomarkers) on the surface of cell- or tissue-specific exosomes, said method comprising:
   i) incubating a population of exosomes obtained from a biological fluid with a one or more tissue-specific antibodies that bind an antigen specific to a tissue or cell type of interest that produces exosomes, where said tissue specific antibodies are attached to acceptor beads and said incubating is under conditions where said tissue-specific antibodies bind exosomes displaying said antigen;
   ii) isolating exosomes bound by said tissue specific antibodies to produce isolated tissue-specific exosomes;
   iii) incubating a test subset of said isolated tissue-specific exosomes with acceptor beads attached to test antibodies that bind an antigen of interest under conditions where said antibodies that bind an antigen of interest bind to exosomes that display said antigen of interest;
   iv) incubating a control subset of said isolated tissue-specific exosomes with negative control acceptor beads under the same conditions as in step iii where the concentration of control acceptor beads is about the same as the concentration of the acceptor beads attached to an antibody that binds a marker of interest;
   v) incubating said test subset of isolated exosomes and said control subset of said exosomes with an antibody that binds an exosome specific antigen where said antibody is attached to a donor that produces singlet oxygen when illuminated;
   vi) detecting a signal produced upon illumination of said control subset and said test subset where said signal is produced by reaction of the negative control acceptor beads reaction of the acceptor beads attached to test antibodies with said donor; and
   vii) identifying the presence or quantifying said antigen(s) of interest, wherein said identifying or quantifying comprises determining the difference in signal produced upon illumination of said test subset and said control subset.

2. The method of claim 1, wherein said method further comprises normalizing said difference to the signal level produced by the control subset.

3. The method of claim 1, wherein said biological fluid comprises a biological fluid selected from the group consisting of blood or blood plasma, lymph, cerebrospinal fluid, vitreous humor, sweat, breast milk, semen, tears, saliva, and urine.

4. The method of claim 1, wherein said tissue specific antibodies comprise antibodies that bind an antigen specific to a cell type or tissue selected from the group consisting of neural tissue and/or brain tissue, heart, lung, liver, stomach, kidney, pancreas, prostate, large intestine, small intestine, eye, spleen, pituitary gland, colon, and bladder.

5. The method of claim 4, wherein said tissue specific antibodies comprise antibodies that bind to an antigen selected from the group consisting of Neuronal Cell Adhesion Molecule (NCAM), nestin, and musashi-1.

6. The method of claim 1, wherein said acceptor beads attached to test antibodies comprise acceptor beads attached to an antibody that binds a marker of Alzheimer's disease, or Parkinson's disease, or multiple sclerosis, or a sleep disorder, or a cancer marker.

7. The method of claim 6, wherein:
   said acceptor beads are attached to an antibody that binds a marker of Alzheimer's disease selected from the group consisting of P-S396-tau, P-T181-tau, Aβ,Aβ-42, and sAPPα; or
   said acceptor beads are attached to an antibody that binds a marker of Parkinson's disease comprising α-synuclein; or
   said acceptor beads are attached to an antibody that binds a marker for multiple sclerosis comprising myelin basic protein (MBP); or
   said acceptor beads are attached to an antibody that binds a marker for a sleep disorder comprising orexin; or
   said acceptor beads are attached to an antibody that binds to a cancer marker selected from the group consisting of Caveolin-1, EpCAM, FasL, TRAIL, Galectine3, CD151, Tetraspanin 8, EGFR, RPN2, CD44, CD47, CA15-3, CA27.29, CA19-9, CA-125, carcinoembryonic antigen (CEA), CD20, chromogranin A (CgA), cytokeratin fragments 21-1, HER4, HER2/neu, and TGF-13; or said acceptor beads are attached to an antibody that binds to a marker for glioma selected from the group consisting of epidermal growth factor receptor type III variant (EGFRvIII), and isocitrate dehydrogenase 1 (IDH1) Arg132 mutant.

8. The method of claim 1, wherein:

said negative control acceptor beads comprise acceptor beads without an antibody attached thereto; or said negative control acceptor beads comprise acceptor beads attached to a non-specific antibody or to an antibody specific for a target that is not present in the assay system.

9. The method of claim 1, wherein the antibody that binds an exosome specific antigen comprise an antibody that binds an exosome-specific antigen selected from the group consisting of CD63, CD9, CD81, hsp70, CD37, CD53, CD82, CD13, CD11, CD86, ICAM-1, Rab5, Annexin V, and LAMP1, CD-31, HLA-G, and Rab5bT.

10. The method of claim 1, wherein:

the donor is attached to antibody before contacting to the exosome; and/or the antibody that binds the exosome-specific antigen is biotinylated and antibody is first contacted to exosome and then avidin or streptavidin conjugated donor beads are added to the reaction.

11. The method of claim 1, wherein said isolating exosomes bound by said tissue specific antibodies to produce isolated tissue-specific exosomes comprises isolation by centrifugation.

12. The method of claim 1, wherein said exosomes are obtained from a biological fluid diluted with blocking buffer containing protease and phosphatase inhibitors and no detergent.

13. The method of claim 1, wherein said incubation in step (i) is performed for a period of time ranging from about 0.5 hours or from about 1 hour, or from about 2 hours up to about 48 hours, or up to about 36 hours, or up to about 24 hours, or up to about 12 hours, or up to about 8 hours.

14. The method of claim 4, wherein said tissue specific antibodies comprise antibodies that bind an antigen specific to brain and/or neural tissue.

15. The method of claim 1, wherein biotinylated isotype control antibodies are used to control for non-specific binding.

16. The method of claim 1, wherein said method is performed in a multiwell plate and said identifying the presence or quantifying said antigens of interest comprising reading a signal using a plate reader.

* * * * *